United States Patent
Skobieranda et al.

(10) Patent No.: US 12,138,233 B2
(45) Date of Patent: Nov. 12, 2024

(54) METHODS OF TREATING IDIOPATHIC HYPERSOMNIA

(71) Applicant: JAZZ PHARMACEUTICALS IRELAND LIMITED, Dublin (IE)

(72) Inventors: Franck Skobieranda, Palo Alto, CA (US); Dan Chen, Los Altos, CA (US); Amanda Leigh Sterkel, Santa Clara, CA (US); Cuiping Chen, Palo Alto, CA (US); Patricia Chandler, Palo Alto, CA (US)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 91 days.

(21) Appl. No.: 17/180,991

(22) Filed: Feb. 22, 2021

(65) Prior Publication Data

US 2022/0008367 A1 Jan. 13, 2022

Related U.S. Application Data

(60) Provisional application No. 63/142,738, filed on Jan. 28, 2021, provisional application No. 63/088,902, filed on Oct. 7, 2020, provisional application No. 63/069,811, filed on Aug. 25, 2020, provisional application No. 62/993,381, filed on Mar. 23, 2020, provisional application No. 62/979,667, filed on Feb. 21, 2020.

(51) Int. Cl.
| | | |
|---|---|---|
| A61K 31/19 | (2006.01) | |
| A61K 9/08 | (2006.01) | |
| A61P 25/00 | (2006.01) | |

(52) U.S. Cl.
CPC .............. *A61K 31/19* (2013.01); *A61K 9/08* (2013.01); *A61P 25/00* (2018.01)

(58) Field of Classification Search
CPC ........ A61K 31/19; A61K 9/0053; A61P 25/00
See application file for complete search history.

(56) References Cited

U.S. PATENT DOCUMENTS

| | | | |
|---|---|---|---|
| 3,051,619 A | 8/1962 | Marie et al. | |
| 3,419,588 A | 12/1968 | De Man et al. | |
| 4,221,778 A | 9/1980 | Raghunathan | |
| 4,374,441 A | 2/1983 | Carter et al. | |
| 4,393,236 A | 7/1983 | Klosa | |
| 4,510,128 A | 4/1985 | Khanna | |
| 4,524,217 A | 6/1985 | Davenport et al. | |
| 4,684,516 A | 8/1987 | Bhutani | |
| 4,687,662 A | 8/1987 | Schobel | |
| 4,738,985 A | 4/1988 | Kluger et al. | |
| 4,916,161 A | 4/1990 | Patell | |
| 4,939,949 A | 7/1990 | Langenberg | |
| 4,983,632 A | 1/1991 | Gessa et al. | |
| 5,294,430 A | 3/1994 | Borch et al. | |
| 5,380,937 A | 1/1995 | Koehler et al. | |
| 5,415,870 A | 5/1995 | Gergely et al. | |
| 5,594,030 A | 1/1997 | Conte et al. | |
| 5,753,708 A | 5/1998 | Koehler et al. | |
| 5,758,095 A | 5/1998 | Albaum et al. | |
| 5,833,599 A | 11/1998 | Schrier et al. | |
| 5,840,331 A | 11/1998 | Van Cauter et al. | |
| 5,845,255 A | 12/1998 | Mayaud | |
| 5,858,998 A | 1/1999 | Leuschner | |
| 5,955,106 A | 9/1999 | Moeckel et al. | |
| 5,990,162 A | 11/1999 | Scharf | |
| 6,014,631 A | 1/2000 | Teagarden et al. | |
| 6,022,562 A | 2/2000 | Autant et al. | |
| 6,067,524 A | 5/2000 | Byerly et al. | |
| 6,103,292 A | 8/2000 | Del Vecchio | |
| 6,112,182 A | 8/2000 | Akers et al. | |
| 6,317,719 B1 | 11/2001 | Schrier et al. | |
| 6,322,819 B1 | 11/2001 | Burnside et al. | |
| 6,356,873 B1 | 3/2002 | Teagarden et al. | |
| 6,384,020 B1 | 5/2002 | Flanner et al. | |
| 6,436,998 B1 | 8/2002 | Cacciaglia et al. | |
| 6,472,431 B2 | 10/2002 | Cook et al. | |
| 6,472,432 B1 | 10/2002 | Perricone | |
| 6,495,598 B1 | 12/2002 | Yoneda et al. | |
| 6,565,872 B2 | 5/2003 | Wu et al. | |
| 6,780,889 B2 | 8/2004 | Cook et al. | |
| 7,015,200 B2 | 3/2006 | Mamelak et al. | |
| 7,072,840 B1 | 7/2006 | Mayaud | |
| 7,262,219 B2 | 8/2007 | Cook et al. | |
| 7,568,822 B2 | 8/2009 | Ibrahim | |
| 7,668,730 B2 | 2/2010 | Reardan et al. | |
| 7,765,106 B2 | 7/2010 | Reardan et al. | |
| 7,765,107 B2 | 7/2010 | Reardan et al. | |
| 7,797,171 B2 | 9/2010 | Reardan et al. | |

(Continued)

FOREIGN PATENT DOCUMENTS

| | | |
|---|---|---|
| AU | 2011224350 A1 | 10/2012 |
| CA | 2112663 C | 4/2002 |

(Continued)

OTHER PUBLICATIONS

Trotti LM. "Idiopathic Hypersomnia", Sleep Med Clin., Sep;12(3):331-344. (Year: 2017).*

Montplaisir J, Barbezieux EM. Le gamma-hydroxybutyrate de sodium (GHB) dans le traitement de l'hypersomnie essentielle. The Canadian Journal of Psychiatry. 1981;26(3):162-166.*

21 C.F.R. 184, Food and Drug Administration, HHS, (1998), pp. 441-535.

Activase, Physicians Desk Reference (50th ed.), (1996), pp. 312, 1058-1061.

Ahmed et al., "Overview of Central Disorders of Hypersomnolence," Reference Module in Neuroscience and Biobehavioral Psychology, 2016, 7 pages.

Akifuddin et al. "Preparation, characterization and in-vitro evaluation of microcapsules for controlled release of Diltiazem hydrochloride by Ionotropic gelation technique." Journal of Applied Pharmaceutical Science (2013); 3.4: 35-42.

(Continued)

*Primary Examiner* — Sahar Javanmard
(74) *Attorney, Agent, or Firm* — COOLEY LLP

(57) ABSTRACT

The present disclosure relates to methods of treating idiopathic hypersomnia with oxybate, preferably a mixture of salts of oxybate (a mixed salt oxybate).

23 Claims, 5 Drawing Sheets

(56) References Cited

U.S. PATENT DOCUMENTS

| | | | |
|---|---|---|---|
| 7,851,506 B2 | 12/2010 | Cook et al. | |
| 7,895,059 B2 | 2/2011 | Reardan et al. | |
| 8,101,209 B2 | 1/2012 | Legrand et al. | |
| 8,193,211 B2 | 6/2012 | Liang et al. | |
| 8,202,537 B2 | 6/2012 | Mehta et al. | |
| 8,263,125 B2 | 9/2012 | Vaya et al. | |
| 8,263,650 B2 | 9/2012 | Cook et al. | |
| 8,324,275 B2 | 12/2012 | Cook et al. | |
| 8,457,988 B1 | 6/2013 | Reardan et al. | |
| 8,461,197 B2 | 6/2013 | Tung | |
| 8,461,203 B2 | 6/2013 | Cook et al. | |
| 8,529,954 B2 | 9/2013 | Lebon et al. | |
| 8,589,182 B1 | 11/2013 | Reardan et al. | |
| 8,591,922 B1 * | 11/2013 | Allphin | A61P 25/04 514/557 |
| 8,598,191 B2 | 12/2013 | Liang et al. | |
| 8,680,228 B2 | 3/2014 | Guo et al. | |
| 8,731,963 B1 | 5/2014 | Reardan et al. | |
| 8,759,394 B2 | 6/2014 | Tung et al. | |
| 8,771,735 B2 | 7/2014 | Rourke et al. | |
| 8,772,306 B1 | 7/2014 | Eller | |
| 8,778,301 B2 | 7/2014 | Mamelak et al. | |
| 8,778,398 B2 | 7/2014 | Rourke et al. | |
| 8,859,619 B2 | 10/2014 | Cook et al. | |
| 8,901,173 B2 | 12/2014 | Allphin et al. | |
| 8,952,029 B2 | 2/2015 | Eller | |
| 8,952,062 B2 | 2/2015 | Cook et al. | |
| 9,023,400 B2 | 5/2015 | Guimberteau et al. | |
| 9,050,302 B2 | 6/2015 | Eller | |
| 9,132,107 B2 | 9/2015 | Allphin et al. | |
| 9,486,426 B2 | 11/2016 | Eller | |
| 9,539,330 B2 | 1/2017 | Cook et al. | |
| 9,555,017 B2 | 1/2017 | Allphin et al. | |
| 9,770,514 B2 | 9/2017 | Ghebre-Sellassie et al. | |
| 9,795,567 B2 | 10/2017 | Rourke et al. | |
| 9,801,852 B2 | 10/2017 | Allphin | |
| 10,195,168 B2 | 2/2019 | Allphin et al. | |
| 10,213,400 B2 | 2/2019 | Eller | |
| 10,272,062 B2 | 4/2019 | Megret et al. | |
| 10,398,662 B1 | 9/2019 | Allphin et al. | |
| 10,675,258 B2 | 6/2020 | Allphin et al. | |
| 10,736,866 B2 | 8/2020 | Megret et al. | |
| 10,758,488 B2 | 9/2020 | Allphin et al. | |
| 10,813,885 B1 | 10/2020 | Allphin et al. | |
| 10,925,844 B2 | 2/2021 | Grassot et al. | |
| 10,952,986 B2 | 3/2021 | Megret et al. | |
| 10,959,956 B2 | 3/2021 | Allphin et al. | |
| 10,966,931 B2 | 4/2021 | Allphin et al. | |
| 10,973,795 B2 | 4/2021 | Megret et al. | |
| 10,987,310 B2 | 4/2021 | Allphin et al. | |
| 11,065,224 B2 | 7/2021 | Megret et al. | |
| 11,077,079 B1 | 8/2021 | Allphin et al. | |
| 11,090,269 B1 | 8/2021 | Allphin et al. | |
| 11,147,782 B1 | 10/2021 | Allphin et al. | |
| 11,207,270 B2 | 12/2021 | Allphin et al. | |
| 11,364,215 B1 | 6/2022 | Allphin et al. | |
| 11,400,052 B2 | 8/2022 | Walsh et al. | |
| 11,426,373 B2 | 8/2022 | Allphin et al. | |
| 2002/0077334 A1 | 6/2002 | Cook et al. | |
| 2003/0180249 A1 | 9/2003 | Khanna et al. | |
| 2004/0092455 A1 | 5/2004 | Mamelak et al. | |
| 2004/0132633 A1 | 7/2004 | Carter et al. | |
| 2005/0031688 A1 | 2/2005 | Ayala | |
| 2005/0037077 A1 | 2/2005 | Legrand et al. | |
| 2005/0113366 A1 | 5/2005 | Bourguignon et al. | |
| 2005/0142192 A1 | 6/2005 | Benjamin et al. | |
| 2006/0018933 A1 | 1/2006 | Vaya et al. | |
| 2006/0024365 A1 | 2/2006 | Vaya et al. | |
| 2006/0069040 A1 | 3/2006 | Mamelak | |
| 2006/0078614 A1 | 4/2006 | Venkatesh | |
| 2006/0210630 A1 | 9/2006 | Liang et al. | |
| 2006/0228410 A1 | 10/2006 | Dumont et al. | |
| 2007/0270491 A1 | 11/2007 | Cook et al. | |
| 2008/0003267 A1 | 1/2008 | Spencer et al. | |
| 2008/0069871 A1 | 3/2008 | Vaughn et al. | |
| 2008/0085304 A1 | 4/2008 | Baichwal et al. | |
| 2008/0118571 A1 | 5/2008 | Lee et al. | |
| 2008/0226564 A1 | 9/2008 | Weers et al. | |
| 2008/0292700 A1 | 11/2008 | Nghiem et al. | |
| 2008/0293698 A1 | 11/2008 | Johnson | |
| 2009/0137565 A1 | 5/2009 | Frucht | |
| 2009/0155357 A1 | 6/2009 | Muhuri | |
| 2009/0317355 A1 | 12/2009 | Roth et al. | |
| 2010/0055133 A1 | 3/2010 | Duffield et al. | |
| 2010/0112056 A1 | 5/2010 | Rourke et al. | |
| 2010/0266701 A1 | 10/2010 | Guimberteau et al. | |
| 2011/0034727 A1 | 2/2011 | Luchi et al. | |
| 2011/0039929 A1 | 2/2011 | Cook et al. | |
| 2011/0091537 A1 | 4/2011 | Castan et al. | |
| 2011/0111027 A1 | 5/2011 | Rourke et al. | |
| 2011/0213004 A1 | 9/2011 | Kim et al. | |
| 2012/0020833 A1 | 1/2012 | Cook et al. | |
| 2012/0076865 A1 | 3/2012 | Allphin et al. | |
| 2012/0148672 A1 | 6/2012 | Mehta et al. | |
| 2012/0202879 A1 | 8/2012 | Cook et al. | |
| 2012/0202880 A1 | 8/2012 | Cook et al. | |
| 2013/0230587 A1 | 9/2013 | Pilgaonkar et al. | |
| 2013/0273159 A1 | 10/2013 | Howard et al. | |
| 2014/0004202 A1 | 1/2014 | Suplie et al. | |
| 2014/0037745 A1 | 2/2014 | Liang et al. | |
| 2014/0072624 A1 | 3/2014 | Jung et al. | |
| 2014/0093578 A1 | 4/2014 | Mehta et al. | |
| 2014/0127306 A1 | 5/2014 | Mehta et al. | |
| 2014/0141090 A1 | 5/2014 | Wilson | |
| 2014/0171506 A1 | 6/2014 | Allphin et al. | |
| 2014/0271896 A1 | 9/2014 | Abu Shmeis et al. | |
| 2014/0275244 A1 | 9/2014 | Khayrallah et al. | |
| 2014/0348917 A1 | 11/2014 | Rourke et al. | |
| 2015/0005334 A1 | 1/2015 | Shah et al. | |
| 2015/0073052 A1 | 3/2015 | Cook et al. | |
| 2015/0328168 A1 | 11/2015 | Daviaud-Venet et al. | |
| 2016/0068463 A1 | 3/2016 | Peoples et al. | |
| 2016/0228379 A1 | 8/2016 | Kumar et al. | |
| 2016/0271070 A1 | 9/2016 | Singh et al. | |
| 2016/0338966 A1 | 11/2016 | Guimberteau et al. | |
| 2016/0346200 A1 | 12/2016 | Sommer et al. | |
| 2016/0346216 A1 | 12/2016 | Chen | |
| 2017/0119627 A1 | 5/2017 | Bhargava et al. | |
| 2017/0340519 A9 | 11/2017 | Bhargava et al. | |
| 2018/0008539 A1 | 1/2018 | Singh et al. | |
| 2018/0021284 A1 | 1/2018 | Megret et al. | |
| 2018/0042855 A1 | 2/2018 | Rourke et al. | |
| 2018/0263936 A1 | 9/2018 | Allphin et al. | |
| 2018/0318222 A1 | 11/2018 | Allphin et al. | |
| 2019/0183806 A1 | 6/2019 | Guillard | |
| 2019/0183836 A1 | 6/2019 | Mégret et al. | |
| 2019/0269640 A1 | 9/2019 | Megret et al. | |
| 2019/0269641 A1 | 9/2019 | Megret et al. | |
| 2019/0274990 A1 | 9/2019 | Megret et al. | |
| 2019/0282532 A1 | 9/2019 | Megret et al. | |
| 2020/0113840 A1 | 4/2020 | Allphin et al. | |
| 2020/0197347 A1 | 6/2020 | Megret et al. | |
| 2020/0276142 A1 | 9/2020 | Grassot et al. | |
| 2020/0330393 A1 | 10/2020 | Walsh et al. | |
| 2020/0360293 A1 | 11/2020 | Guillard | |
| 2020/0360319 A1 | 11/2020 | Grassot et al. | |
| 2020/0368187 A1 | 11/2020 | Grassot et al. | |
| 2021/0093575 A1 | 4/2021 | Rourke et al. | |
| 2021/0121423 A1 | 4/2021 | Allphin et al. | |
| 2022/0096384 A1 | 3/2022 | Allphin et al. | |
| 2022/0160640 A1 | 5/2022 | Walsh et al. | |
| 2023/0390228 A1 | 12/2023 | Skobieranda et al. | |
| 2023/0404950 A1 | 12/2023 | Skobieranda | |

FOREIGN PATENT DOCUMENTS

| | | |
|---|---|---|
| CA | 2510289 A1 | 7/2004 |
| CN | 102905688 A | 1/2013 |
| CN | 102958930 A | 3/2013 |
| CN | 103209966 A | 7/2013 |
| CN | 103209967 A | 7/2013 |
| EP | 0203768 A2 | 12/1986 |
| EP | 0235408 A1 | 9/1987 |
| EP | 0344704 A1 | 12/1989 |

(56) References Cited

FOREIGN PATENT DOCUMENTS

| | | |
|---|---|---|
| EP | 0616804 A1 | 9/1994 |
| EP | 0635265 A1 | 1/1995 |
| EP | 0709087 B1 | 12/1999 |
| EP | 0635265 B1 | 2/2000 |
| EP | 1140061 A2 | 10/2001 |
| EP | 1140061 B1 | 5/2003 |
| EP | 1316309 A1 | 6/2003 |
| EP | 2760911 B1 | 11/2017 |
| EP | 1434572 B1 | 12/2017 |
| GB | 922029 A | 3/1963 |
| GB | 2295390 A | 5/1996 |
| JP | S5742651 A | 3/1982 |
| JP | S6212715 A | 1/1987 |
| JP | 04049212 A | 2/1992 |
| JP | H05508422 A | 11/1993 |
| JP | H06508839 A | 10/1994 |
| JP | H0753365 A | 2/1995 |
| JP | H08511257 A | 11/1996 |
| JP | H09104620 A | 4/1997 |
| JP | H10505604 A | 6/1998 |
| JP | 2001513552 A | 9/2001 |
| JP | 2002533388 A | 10/2002 |
| JP | 2004514732 A | 5/2004 |
| JP | 2007521231 A | 8/2007 |
| JP | 2008512386 A | 4/2008 |
| JP | 2008519847 A | 6/2008 |
| JP | 2008528571 A | 7/2008 |
| JP | 2009532331 A | 9/2009 |
| JP | 2011500865 A | 1/2011 |
| JP | 2012507532 A | 3/2012 |
| RU | 2210360 C1 | 8/2003 |
| WO | WO-9428880 A1 | 12/1994 |
| WO | WO-9640105 A1 | 12/1996 |
| WO | WO-9909972 A1 | 3/1999 |
| WO | WO-0038672 A2 | 7/2000 |
| WO | WO-0245684 A2 | 6/2002 |
| WO | WO-2005016318 A1 | 2/2005 |
| WO | WO-2005030174 A1 | 4/2005 |
| WO | WO-2005092336 A1 | 10/2005 |
| WO | WO-2005099671 A2 | 10/2005 |
| WO | WO-2006029155 A2 | 3/2006 |
| WO | WO-2006053186 A2 | 5/2006 |
| WO | WO-2006080029 A1 | 8/2006 |
| WO | WO-2007053698 A2 | 5/2007 |
| WO | WO-2007103200 A2 | 9/2007 |
| WO | WO-2008086804 A2 | 7/2008 |
| WO | WO-2009056550 A2 | 5/2009 |
| WO | WO-2010053691 A1 | 5/2010 |
| WO | WO-2010055260 A1 | 5/2010 |
| WO | WO-2010105673 A1 | 9/2010 |
| WO | WO-2011119839 A1 | 9/2011 |
| WO | WO-2011127252 A2 | 10/2011 |
| WO | WO-2011135461 A2 | 11/2011 |
| WO | WO-2011139271 A1 | 11/2011 |
| WO | WO-2011140310 A2 | 11/2011 |
| WO | WO-2012028688 A1 | 3/2012 |
| WO | WO-2012107652 A1 | 8/2012 |
| WO | WO-2014078014 A2 | 5/2014 |
| WO | WO-2014144027 A1 | 9/2014 |
| WO | WO-2015120006 A1 | 8/2015 |
| WO | WO-2015120110 A2 | 8/2015 |
| WO | WO-2015166473 A1 | 11/2015 |
| WO | WO-2015181059 A1 | 12/2015 |
| WO | WO-2016065481 A1 | 5/2016 |
| WO | WO-2016087952 A1 | 6/2016 |
| WO | WO-2016178132 A1 | 11/2016 |
| WO | WO-2017147375 A1 | 8/2017 |
| WO | WO-2017182851 A1 | 10/2017 |
| WO | WO-2018015563 A1 | 1/2018 |
| WO | WO-2019123269 A1 | 6/2019 |
| WO | WO-2020106735 A1 | 5/2020 |
| WO | WO-2020178695 A1 | 9/2020 |
| WO | WO-2021133778 A1 | 7/2021 |
| WO | WO-2021168403 A1 | 8/2021 |
| WO | WO-2022076824 A1 | 4/2022 |
| WO | WO-2022082105 A2 | 4/2022 |
| WO | WO-2023062018 A1 | 4/2023 |
| WO | WO-2023135150 A1 | 7/2023 |

OTHER PUBLICATIONS

Ali et al., "Idiopathic Hypersomnia: Clinical Features and Response to Treatment," Journal of Clinical Sleep Medicine, 2009, 5(6), 562-568.

Alshaikh et al., "Sodium Oxybate for Narcolepsy with Cataplexy: Systematic Review and MetaAnalysis," Journal of Clinical Sleep Medicine, 2012, vol. 8, No. 4, 451-458.

American Heart Association, "Why Should I Limit Sodium?" 2017, 2 pages, retrieved from https://www.heart.org/-/media/files/health-topics/answers-by-heart/why-should-i-limit-sodium.pdf.

Anand et al. "Ion-exchange resins: carrying drug delivery forward." Drug Discovery Today (2001); 6.17: 905-914.

Andersen et al., "Idiopathic Hypersomnia: A Study of 77 Cases," Sleep, 2007; 30(10):1274-1281.

Arena et al. "Absorption of sodium γ-hydroxybutyrate and its Prodrug butyrolactone: Relationship between in vitro transport and in Vivo absorption." Journal of Pharmaceutical Sciences (1980); 69 (3): 356-358.

Baldrick P. Pharmaceutical excipient development: the need for preclinical guidance. Regul. Toxicol Pharmacol. 32(2):210-8 (2000).

Bassetti, C. and M.S. Aldrich (1997). Idiopathic hypersomnia. A series of 42 patients. Brain, 120:1423-1435.

Bedard, "Nocturnal γ-Hydroxybutyrate—Effect on Periodic Leg Movements and Sleep Organization of Narcoleptic Patients," Clin Neuropharmacol., 12(1), Feb. 1989, 29-36.

Berner, Jon E., "A Case of Sodium Oxybate Treatment of Tardive Dyskinesia and Bipolar Disorder," J. Clin. Psychiatry, 2008, 69:5, p. 862.

Berthier, et al., "Possible Involvement of a Gamma-Hydroxybutyric Acid Receptor in Startle Disease," Acta Paediatr, 83, 1994, 678-680.

Billiard and Sonka, "Idiopathic hypersomnia," Sleep Medicine Reviews, Oct. 2016, vol. 29, pp. 23-33.

Billiard, M., Epidemiology of central disorders of hypersomnolence, Reference Module in Neuroscience and Biobehavioral Psychology, 2017, 9 pages.

Bodmeier, R., "Tableting of coated pellets," European Journal of Pharmaceutics and Biopharmaceutics, (1997) 43(1), 1-8.

Borgen et al., "The influence of gender and food on the pharmacokinetics of sodium oxybate oral solution in healthy subjects." J Clin Pharmacol. (2003); 43(1): 59-65.

Borgen, L., et al. "Xyrem (sodium oxybate): A Study of Dose Proportionality in Healthy Human Subjects." J. Clin. Pharmacol. (2000); 40: 1053.

Broughton, et al. "Effects of Nocturnal Gamma-Hydroxybutyrate on Spell/Waking Patterns in Narcolepsy-Cataplexy." Can J. Neural Sci (1980); 7 (1): 23-31.

Broughton, et al. "Gamma-Hydroxy-Butyrate in the Treatment of Narcolepsy: a Preliminary Report." (1976) Narcolepsy, Ny, N.Y., Spectrum Publications, Inc. 659-668.

Broughton et al., "The Treatment of Narcolepsy-Cataplexy with Nocturnal Gamma-Hydroxybutyrate." Can J. Neural Sci (1979); 6(1): 1-6.

Caballero et al. "Characterization of alginate beads loaded with ibuprofen lysine salt and optimization of the preparation method." International Journal of Pharmaceutics (2014); 460.1: 181-188.

Chem Abstract ES302338, SciFinder, (1964), 1 pg.

Chemical Abstracts: Seventh Collective Index, vols. 56-65, (1962-1966), 4 pgs.

Chen et al, "Pharmacokinetics, relative bioavailability and food effect of JZP-258 and sodium oxybate: results of two phase 1, open-label, randomised crossover studies in healthy volunteers," Sleep Medicine, Abstracts, 2019, vol. 64, pp. S65-S66.

ClinicalTrials.gov Identifier: NCT02512588, A Study of Safety and Efficacy of BTD-001 in Treatment of Patients With Idiopathic Hypersomnia (IH) or Narcolepsy Type 2, First Posted—Jul. 31, 2015, Last Update Posted—Jan. 16, 2019, retrieved from https://clinicaltrials.gov/ct2/show/NCT02512588, 6 pages.

(56) References Cited

OTHER PUBLICATIONS

Davis et al. "Active chloride secretion in the normal human jejunum." J Clin Invest. (1980); 66(6): 1326-1333.
Delrosso et al. "Manual Characterization of Sleep Spindle Index in Patients with Narcolepsy and Idiopathic Hypersomnia," Sleep Disorders, 2014, vol. 2014, Article ID 271802, 4 pages.
Erowid, "Gamma-hydroxybutyrnte (GHB) Basic Synthesis Procedure," http://www.erowid.orq/chemicals/qhb/qhb svnthesis.shtml (as downloaded on Aug. 8, 2013), 6 pages.
European Search Report issued Apr. 11, 2003 in European Application No. 03075658.9, 5 pages.
Evangelista et al., "Update on treatment for idiopathic hypersomnia," Expert Opinion on Investigational Drugs, 2018, 27(2), 187-192.
Ferrara, S. D., et al., "Pharmacokinetics of γ-Hydroxybutyric Acid in Alcohol Dependent Patients After Single and Repeated Oral Doses." Br. J. Clin. Pharmacol. (1992); 34: 231-235.
Ferris, T.J., et al., "Synthesis, characterisation and detection of gamma-hydroxybutyrate salts," Forensic Science International, 2012, 216:158-162.
Fides, "Solutions of 4-hydroxybutyric acid salts for injection," Chem Abstract ES302338. Laboratorio M. Cuatecases, S.A., 2011, 2 pp.
Frucht, et al. "A pilot Tolerability and Efficacy Trial of Sodium Oxybate in Ethanol-Responsive Movement Disorders." Movement Disorders (2005); 20 (10): 1330-1337.
Frucht, S.J., et al., "A Single-Blind, Open-Label Trial of Sodium Oxybate for Myoclonus and Essential Tremor," Neurology (2005); 65 (12): 1967-1970.
Gallimberti et al., "Clinical efficacy of gamma-hydroxybutyric acid in treatment of opiate withdrawal," Eur Arch Psychiatry Clin Neurosci. 1994;244(3):113-114.
Gallimberti et al., "Gamma-Hydroxybutyric Acid for Treatment of Opiate Withdrawal Syndrome," Neuropsychopharmacology, 1993, vol. 9, No. 1, pp. 77-81.
Gallimberti, L., "Gamma-hydroxybutyric Acid for Treatment of Alcohol Withdrawal Syndrome," The Lancet, 2(8666), (1989), 787-789.
Gallimberti, L., "Gamma-Hydroxybutyric Acid in the Treatment of Alcohol Dependence: A Double-Blind Study," Alcohol Clin. Exp. Res. (1992), 16(4): 673-676.
Geek Wench et al., "Title: Does anyone know why Jazz choose to make sodium oxybate?", Sep. 14, 2010: downloaded from http://www.talkaboutsleep.com/message-boards/topic/docs-anybody- know-why-jazz-chose-to-make-sodium-oxybate/ on Nov. 13, 2017 (30 pages).
Geekwench et al., "Title: Does anyone know why Jazz choose to make sodium oxybate?", Sep. 14, 2010; downloaded from http://www.talkaboutsleep.com/message/boards/topic/does-anybodyknow-why-jazz-chose-to-make-sodium-oxybate/#sthash.no0PSCkL.dpuf on Jan. 21, 2015 (30 pages).
Gerra, G., et al., "Flumazenil effects on growth hormone response to gamma-hydroxybutyric acid," Int Clin Psychopharmacol. (1994); 9 (3): 211-215.
Gessa, G. L., et al., "Gamma-hydroxybutyric acid (GHB) for treatment of ethanol dependence," European Neuropsychopharmacology, 3(3), (1993), 224-225.
Gessa, G. L., "Gamma-hydroxybutyric Acid in the Treatment of Alcohol Dependence," Clin. Neuropharm., vol. 15 Suppl. 1, Pt A, (1992), 303a-304a.
Grove-White, I. G., "Critical Flicker Frequency after Small Doses of Methohexitone, Diazepam and Sodium 4-Hydroxybutyrate." Brit. J. Anaesth (1971); 43 (2): 110-112.
Grove-White, I. G., et al., "Effect of Methohexitone, Diazepam and Sodium 4-Hydroxybutyrate on Short-Term Memory." Brit. J. Anaesth (1971); 43 (2): 113-116.
Hasenbos, M.A., et al., "Anaesthesia for bullectomy. A technique with spontaneous ventilation and extradural blockade." Anaesthesia (1985); 40 (10): 977-980.
"HIB-IMUNE," Physicians Desk Reference (41st ed.), (1987), 1095-1096.
"HibVAX," Physicians Desk Reference (41st ed.), (1987), 870.
Hoes, M. J., "Gamma-hydroxybutyric acid (*) as hypnotic. Clinical and pharmacokinetic evaluation of gammahydroxybutyric acid as hypnotic in man," L'Encephale: Revue de psychiatrie clinique biologique et therapeutique (1980); 6 (1): 93-99.
International Search Report and Written Opinion of the International Searching Authority for International Application No. PCT/US2019/062237, dated Mar. 31, 2020, 11 pages.
International Search Report and Written Opinion of the International Searching Authority for International Application No. PCT/US2020/066561, dated Apr. 13, 2021, 12 pages.
International Search Report and Written Opinion of the International Searching Authority for International Application No. PCT/US2021/019024, dated Jun. 2, 2021, 10 pages.
International Searching Authority, International Search Report and Written Opinion, mailed Jun. 27, 2018 for International Patent Application No. PCT/EP2018/056745 (12 pages).
International Searching Authority, International Search Report for International Application Serial No. PCT/US99/30740, mailed Jul. 21, 2000, 1 pg.
International Searching Authority, "International Search Report, mailed Apr. 15, 2014, for International Patent Application No. PCT/US2013/074954" 3 pages.
International Searching Authority, "Written Opinion, mailed Apr. 15, 2014, for International Patent Application No. PCT/US2013/074954" 8 pages.
Jazz Pharmaceuticals, Inc., "Xyrem® (sodium oxybate) oral solution, CIII," Highlights of Prescribing Information, Revised, Sep. 2020, 35 pages.
Jazz Pharmaceuticals, Inc., "Xywav® (calcium, magnesium, potassium, and sodium oxybates) oral solution, CIII," Highlights of Prescribing Information, Aug. 2021, 40 pages.
Jazz Pharmaceuticals, Inc., "Xyrem® (sodium oxybate) oral solution Prescribing Information," Xyrem® US Package Insert available at http://pp.jazzpliamia.com/pi/xyem.en.USPI.pdf (downloaded Sep. 12, 2017, 32 pages).
Jazz Pharmaceuticals, "Jazz Pharmaceuticals Announces Positive Top-line Results from Phase 3 Study of JZP-258 in Adult Narcolepsy Patients with Cataplexy and Excessive Daytime Sleepiness," Mar. 26, 2019, 2 pages, retrieved from https://investor.jazzpharma.com/node/16206/pdf.
Jennum et al., "Comorbidity and Mortality of Narcolepsy: A Controlled Retro- and Prospective National Study," Sleep 2013;36(6):835-840.
Jha, M.K, "Modified release formulations to achieve the quality target product profile (QTPP)," IJPSR,2012; vol. 3(8): 2376-2386.
Keating, GM, "Sodium Oxybate: A Review of Its Use in Alcohol Withdrawal Syndrome and in the Maintenance of Abstinence in Alcohol Dependence," Clinical Drug Investigation (2014) 34, 63-80.
Khan and Trotti, "Central Disorders of Hypersomnolence: Focus on the Narcolepsies and Idiopathic Hypersomnia," Chest, Jul. 2015, 148(1): 262-273.
Khediri et al., "Efficacy of Diosmectite (Smecta) in the Treatment of Acute Watery Diarrhea in Adults: A Multicenter, Randomized, Double-Blind, Placebo-Controlled, Parallel Group Study," Hindawi Publishing Corporation, Gastroenterology Research and Practice, 2011, vol. 2011, Article ID 783196, 8 pages.
Kim et al., "Different fates of excessive daytime sleepiness: survival analysis for remission," Acta Neurologica Scandinavica, 2016, 134(1):35-41.
Laborit, H., "Gamma-Hydroxybutyrate, Succinic Semialdehyde and Sleep," Laboratoire d'Eutonologie, (1973), 257-274.
Ladinsky, H., et al., "Mode of Action of Gamma-Butyrolactone on the Central Cholinergic System, Naunyn-Schmiedeberg's," Arch. Pharmacol. (1983); 322 (1): 42-48.
Lammers, G. J., "Gammahydroxybutyrate and Narcolepsy: A Double-Blind Placebo-Controlled Study." Sleep (1993); 16 (3): 216-220.
Lapierre et al., "The Effect of Gamma-Hydroxybutyrate: A Double-Blind Study of Normal Subjects," Sleep Research (1988); 17:99, 1988, 6 pages. (Abstract Only).
Lapierre, O., "The Effect of Gamma-Hydroxybutyrate on Nocturnal and Diurnal Sleep of Normal Subjects: Further Considerations on REM Sleep-Triggering Mechanisms." Sleep (1990); 13 (1): 24-30.

(56) References Cited

OTHER PUBLICATIONS

Lavault et al., "Benefit and risk of modafinil in idiopathic hypersomnia vs. narcolepsy with cataplexy," Sleep Medicine, 2011, 12(6), 550-556.
Lee, C. R., "Evidence for the β-oxidation of orally administered 4-hydroxybutyrate in humans." Biochemical Medicine (1977); 17 (3): 284-291.
Lettieri and Fung, "Improved pharmacological activity via pro-drug modification: comparative pharmacokinetics of sodium gamma-hydroxybutyrate and gamma-butyrolactone." Research Communications in Chemical Pathology and Pharmacology (1978); 22 (1): 107-118.
Leu-Semenescu et al., "Benefits and risk of sodium oxybate in idiopathic hypersomnia versus narcolepsy type 1: a chart review," Sleep Medicine, Jan. 2016, vol. 17, pp. 38-44.
Leu-Semenescu et al., "Effects of pitolisant, a histamine H3 inverse agonist, in drug-resistant idiopathic and symptomatic hypersomnia: a chart review," Sleep Medicine, Jun. 2014, vol. 15, Issue 6, pp. 681-687.
Lopez et al., "French consensus. Management of patients with hypersomnia: Which strategy?" Revue Neurologique (Paris), 2017, 173(1-2): 8-18.
Lubrano, et al. "Fibromyalgia in Patients with Irritable Bowel Syndrome. An Association with the Severity of the Intestinal Disorder." Int J Colorectal Dis. (2001); 16 (4): 211-215.
Luhn, O., "Using Excipients In Powder Formulations," Pharmaceutical Technology Europe, Jan. 7, 2011, vol. 23, Issue 1, 6 pages, retrieved from https://www.pharmtech.com/view/using-excipients-powder-formulations.
Mahore et al. "Ion exchange resins: pharmaceutical applications and recent advancement." Int J Pharm Sci Rev Res (2010); 1.2: 8-13.
"Malic Acid," The Handbook of Pharmaceutical Excipients, 2nd Ed., (1994), pp. 285-286, 633.
Mamelak, et al. The Effects of γ-Hydroxybutyrate on Sleep. Biol Psych (1977); 12 (2): 273-288.
Mamelak, M., et al., "Treatment of Narcolepsy and Sleep Apnea with Gammahydroxybutyrate: A clinical and polysomnographic case study." Sleep (1981); 4 (1): 105-111.
Mamelak, M., et al., "Treatment of Narcolepsy with γ-hydroxybutyrate. A review of Clinical and Sleep Laboratory Findings." Sleep (1986); 9 (1): 285-290.
Mamelak, M., "Gammahydroxybutyrate: An endogenous regulator of energy metabolism." Neuroscience and Biobehavioral Reviews (1989); 13 (4): 187-198.
Mamelak, M., "Sleep-Inducing Effects of Gammahydroxybutyrate." The Lancet (1973); 302 (7824): 328-329.
Markman Opinion, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES), 21 pages.
Medicines for Children, "Oral Rehydration Salts," Leaflet information published Jul. 25, 2013, by Neonatal and Paediatric Pharmacists Group (NPPG), 6 pages, retrieved from https://www.medicinesforchildren.org.uk/oral-rehyd ration-salts.
Mignot, E.J.M., "A Practical Guide to the Therapy of Narcolepsy and Hypersomnia Syndromes," Neurotherapeutic, 2012, 9(4), 739-752.
Moldofsky et al. "A Chronobiologic Theory of Fibromyalgia." J. Muscoloskel. Pain, 1, 49 (1993).
Moldofsky, et al. "Musculoskeletal Symptoms and Non-REM Sleep Disturbance in Patients with 'Fibrositis Syndrome' and Healthy Subjects." Psychosom. Med. (1975); 37 (4): 341-351.
Morgenthaler et al., "Practice Parameters for the Treatment of Narcolepsy and other Hypersomnias of Central Origin," Sleep, 2007, 30(12): 1705-1711.
Morrison, Robert T., et al., "Organic Chemistry", Chapter 20: "Functional Derivatives of Carboxylic Acids," 3rd Edition, 1973, pp. 658-700.
Morrison, Robert Thornton, et al., Organic Chemistry, 3rd Edition, (1973), pp. 672-677.
Nema, S, et al., "Excipients and Their Use in Injectable Products." PDA J. Pharm. Sci. Technol. (1997); 51(4): 166-171.
Neuman, Ariel, "GHB's Path to Legitimacy: An Administrative and Legislative History of Xyrem." Apr. 2004, Harvard Law School, Class of 2005, Food and Drug Law, Winter Term 2004, Professor Peter Barton Hutt. (2004), 1-39.
Nittur et al., "Mazindol in narcolepsy and idiopathic and symptomatic hypersomnia refractory to stimulants: A long-term chart review," Sleep Medicine, 2013, 14(1), 30-36.
Ohayon, M.M., "Narcolepsy is complicated by high medical and psychiatric comorbidities: a comparison with the general population," Sleep Medicine, Jun. 2013, 14(6):488-492.
Ohta et al. "Development of a simple method for the preparation of a silica gel based controlled delivery system with a high drug content." European Journal of Pharmaceutical Sciences (2005); 26.1: 87-96.
Ondo, William G., et al., "Sodium Oxybate for Excessive Daytime Sleepiness in Parkinson's Disease: A Polysomnographic Study." Arch. Neural. (2008); 65 (10): 1337-1340.
Oosterloo et al., "Possible confusion between primary hypersomnia and adult attention-deficit/hyperactivity disorder," Psychiatry Res. (2006) 143(2-3): 293-297.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil1 0-6108 ES), (Sep. 14, 2012), 1 page.
Outlaw, et al. "Dyspepsia and its Overlap with Irritable Bowel Syndrome." Curr Gastroenterol Rep. (2006); 8 (4): 266-272.
Ozaki et al., "Health-Related Quality of Life Among Drug-Naïve Patients with Narcolepsy with Cataplexy, Narcolepsy Without Cataplexy, and Idiopathic Hypersomnia Without Long Sleep Time," Journal of Clinical Sleep Medicine, 2008, 4(6), 572-578.
Palatini, P., "Dose Dependent Absorption and Elimination of Gamma-Hydroxybutyric Acid in Healthy Volunteers." Eur. J. Clin. Pharmacol. (1993); 45 (4): 353-356.
Parmar et al., "Clinical Characteristics of Cataplectic Attacks in Type 1 Narcolepsy," Current Neurology and Neuroscience Reports (2020) 20:38, 9 pages.
Pascoe et al., "Effects of Pharmacotherapy Treatment on Patient-Reported Outcomes in a Narcolepsy and Idiopathic Hypersomnia Cohort," J Clin Sleep Med., Dec. 15, 2019; 15(12):1799-1806.
Patil et al. "A review on ionotropic gelation method: novel approach for controlled gastroretentive gelispheres." International Journal of Pharmacy and Pharmaceutical Sciences (2012); 4.4: 27-32.
Philip et al., "Is there a link between subjective daytime somnolence and sickness absenteeism? A study in a working population," J. Sleep Res. (2001) 10, 111-115.
"Phospholine Iodide," Physicians Desk Reference (50th ed.), (1996), 2784.
Pizza et al., "Car Crashes and Central Disorders of Hypersomnolence: A French Study," PLoS One, (2015) 10(6):e0129386, 14 pages.
Pizza et al., "Polysomnographic study of nocturnal sleep in idiopathic hypersomnia without long sleep time," J Sleep Res. (2013) 22, 185-196.
Puguan et al. "Diffusion characteristics of different molecular weight solutes in Ca-alginate gel beads." Colloids and Surfaces A: Physicochemical and Engineering Aspects (2015); 469: 158-165.
Remington. The Science and Practice of Pharmacy. 20th Edition, Gennaro, Ed,. Lippincott Williams & Wilkins (2000). (See e.g. p. 861).
Remington. The Science and Practice of Pharmacy. 20th Edition, Gennaro, Ed,. Lippincott Williams & Wilkins. Chapter 45 (Oral Solid Dosage Forms) (2000).
Response filed Feb. 16, 2001 to Written Opinion issued Oct. 18, 2000 in International Application No. PCT/US99/30740, 10 pages.
Rohm and Haas, "Amberlite® IRN78 Industrial Nuclear Grade Strong Base Anion Resin," 2000, PDS 0547—Jan. 1998, 2 pages.
Rohm and Haas. "Duolite AP143/1083 Pharmaceutical Grade Anion Exchange Resin." Feb. 2006, 4 pages.
Roth, et al., "γ-Butyrolactone and γ-Hydroxybutyric Acid-I, Distribution and Metabolism." Biochemical Pharmacology (1966); 15 (9):1333-1348.

(56) References Cited

OTHER PUBLICATIONS

Roth et al., "Hypersomnia With 'Sleep Drunkenness'," Archives of General Psychiatry, 1972, 26(5), 456-462.
Roth, R. H., et al., "-Butyrolactone and -Hydroxybutyric acid—II. The Pharmacologically active form." J. Neuropharmacol. (1966); 5 (6): 421-428.
Roxane Laboratories, Inc.'s Answer, Affirmative Defenses and Counterclaims to Plaintiff's Complaint, (Dec. 29, 2010), 21 pages.
Roxane Laboratories, Inc.'s Answer, Affirmative Defenses and Counterclaims to Plaintiff's Complaint, (Jun. 1, 2011), 12 pages.
Roxane Laboratories, Inc.'s Answer, Affirmative Defenses and Counterclaims to Plaintiff's Complaint, (Mar. 9, 2011), 13 pages.
Roxane Laboratories, Inc.'s Answer, Affirmative Defenses and Counterclaims to Plaintiff's Complaint, (Nov. 9, 2012), 18 pages.
Roxane Laboratories, Inc.'s Answer and Affirmative Defenses to Plaintiff's Complaint, (Jan. 4, 2013), 8 pages.
Roxane Laboratories, Inc.'s Initial Invalidity and Noninfringement Contentions Pursuant to Local Patent Rule 3.6, (Apr. 14, 2011), 317 pages.
Rubbens et al., "Gastric and Duodenal Ethanol Concentrations after intake of Alcoholic Beverages in Postprandial Conditions," Molecular Pharmaceutics, (2017) 14(12):4202-4208.
Rujivipat et al., Improved drug delivery to the lower intestinal tract with tablets compression-coated with enteric/nonenteric polymer powder blends, Sep. 22, 2010, European Journal of Pharmaceutics and Biopharmaceutics, vol. 76, pp. 486-492 (Year: 2010).
Russell, I. Jon, et al., "Sodium Oxybate Relieves Pain and Improves Function in Fibromyalgia Syndrome." Arthritis. Rheum. (2009); 60 (1): 299-309.
Saini and Rye, "Hypersomnia: Evaluation, Treatment, and Social and Economic Aspects," Sleep Medicine Clinics, (2017) 12(1), 47-60.
Scharf, et al., "Effect of Gamma-Hydroxybutyrate on Pain, Fatigue, and the Alpha Sleep Anomaly in Patients with Fibromyalgia," (1998) J. Rheumatol. (1998) 25:1986-1990.
Scharf, M. B et al "GHB—New Hope for Narcoleptics?" Biol Psychiatry (1989); 26 (4): 329-330.
Scharf, M. B "The Effects and Effectiveness of γ-Hydroxybutyrate in Patients with Narcolepsy." J. Clin. Psychiatry (1985); 46 (6): 222-225.
Scharf, Martin B et al., "The Effects of Sodium Oxybate on Clinical Symptoms and Sleep Patterns in Patients with Fibromyalgia." J. Rheumatol. (2003); 30 (5): 1070-1074.
Scrima, et al., "Effect of Gamma-Hydroxybutyrate on a Patient with Obstructive Sleep Apnea." Sleep Research (1987); 16: 137.
Scrima, et al., "Effect of High Altitude on a Patient with Obstructive Sleep Apnea." Sleep Research (1987); 16: 427.
Scrima, et al., "Effects of Gamma-Hydroxybutyrate (GHB) on Narcolepsy-Cataplexy Symptoms and MSLT Results in Male and Female Patients." Association of Professional Sleep Societies (1988); 251.
Scrima, et al., "Gamma-Hydroxybutyrate Effects on Cataplexy and Sleep Attacks in Narcoleptics." Sleep Research (1987); 16: 134.
Scrima, L., et al., "Efficacy of Gamma-Hydroxybutyrate Versus Placebo in Treating Narcolepsy-Cataplexy: Double-Blind Subjective Measures," Biol. Psychiatry (1989); 26 (4): 331-343.
Scrima, L., et al., "Narcolepsy." New England J. Med. (1991); 324 (4): 270-272.
Scrima, L., "The Effects of γ-Hydroxybutyrate on the Sleep of Narcolepsy Patients: A Double-Blind Study." Sleep (1990); 13 (6): 479-490.
Seno and Yamabe. "The Rheological Behavior of Suspensions of Ion-exchange Resin Particles." Bulletin of the Chemical Society of Japan (1966); 39.4: 776-778.
Series, F., "Effects of Enhancing Slow-Wave Sleep by Gamma-Hydroxybutyrate on Obstructive Sleep Apnea." Am. Rev. Respir. Dis. (1992); 145 (6): 1378-1383.
Shah et al., "In vitro Dissolution Profile Comparison—Statistics and Analysis of the Similarity Factor, f2," Pharm Research, (1998) 15(6):889-896.

Shinno et al., "Successful treatment with levothyroxine for idiopathic hypersomnia patients with subclinical hypothyroidism," General Hospital Psychiatry, 2009, 31(2), 190-193.
Singh et al. "Ion exchange resins: drug delivery and therapeutic applications." Fabad J. Pharm. Sci (2007); 32: 91-100.
Snead, et al., "Ontogeny of γ-Hydroxybutyric Acid. I. Regional Concentration in Developing Rat, Monkey and Human Brain." Brain Res. (1981); 227 (4): 579-589.
Snead, O. Carter, "γ-Hydroxybutyrate Model of Generalized Absence Seizures: Further Characterization and Comparison with Other Absence Models." Epilepsia (1988); 29 (4): 361-368.
Srikanth et al., "Ion-exchange resins as controlled drug delivery carriers." Journal of Scientific Research (2010); 2.3: 597-611.
Stock, G., "Increase in brain dopamine after axotomy or treatment with Gammahydroxybutyric acid due to elimination of the nerve impulse flow." Naunyn-Schmiedeberg's Arch. Pharmacol. (1973); 278 (4): 347-361.
Strong, A.J., "γ-Hydroxybutyric acid and intracranial pressure." The Lancet (1984); 1 (8389): 1304.
Suner, Selim, et al., "Pediatric Gamma Hydroxybutyrate Intoxication." Acad Emerg. Med. (1997); 4 (11): 1041-1045.
Takka and Grel. "Evaluation of chitosan/alginate beads using experimental design: formulation and in vitro characterization." AAPS PharmSciTech (2010); 11.1: 460-466.
"Taxotere," Physicians Desk Reference (51st ed.), (1997), 2204-2207.
The Dow Chemical Company, Product Data Sheet for Amberlite IRN78 Resin. Form No. 177-02230-0311, Rev. 0, 3 pages.
Thorpy, M.J., "Recently Approved and Upcoming Treatments for Narcolepsy," CNS Drugs (2020) 34:9-27.
Thorpy M.J., Update on Therapy for Narcolepsy, Apr. 9, 2015, Curr Treat Options Neurol, vol. 17, pp. 20-32 (Year: 2015).
Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012), 231 pages.
Trotti et al., "Flumazenil for the Treatment of Refractory Hypersomnolence: Clinical Experience with 153 Patients," J Clin Sleep Med 2016; 12(10): 1389-1394.
Trotti et al., "Improvement in daytime sleepiness with clarithromycin in patients with GABA-related hypersomnia: Clinical experience," J Psychopharmacol. 2014, 28(7): 697-702.
Tunnicliff, Godfrey, "Sites of Action of Gamma-Hydroxybutyrate (GHB)—A Neuroactive Drug with Abuse Potential." Clinical Toxicology (1997); 35 (6): 581-590.
Turnberg, L.A. "Abnormalities in intestinal electrolyte transport in congenital chloridorrhoea." Gut. (1971); 12(7): 544-551.
United States Pharmacopeial Convention, Inc.: The National Formulary, 23/NF18, (1995), p. 2205.
Unknown author, "How Much Protein is in Your Cup of Milk?" downloaded from https://milklife.com/articles/nutrition/how-much-protein-your-cup-milk, 8 ounces of whole milk on Aug. 20, 2021, 2 pages. (Year: 2021).
Unknown author, title: definition of biotransformation; Medical dictionary; downloaded Jun. 21, 2018 (Year: 2018), 3 pages.
U.S. Department of Health and Human Services et al., "Dissolution Testing of Immediate Release Solid Oral Dosage Forms," Food and Drug Administration, ODER, Aug. 1997,17 pages.
U.S. Department of Health and Human Services et al., "Extended Release Oral Dosage Forms: Development, Evaluation, and Application of In Vitro/In Vivo Correlations", Food and Drug Administration, CDER, Sep. 1997, 27 pages.
U.S. Department of Health and Human Services et al., "Guidance for Industry Food-Effect Bioavailability and Fed Bioequivalence Studies," Food and Drug Administration, COER, Dec. 2002, BP, 12 pages.
Van Den Bogert, A. G., et al., "Placentatransfer of 4-hydroxybutyric acid in man," Anaesthesiology and Intensive Care Medicine (1978); 110: 55-64.
Vernet et al., "Subjective symptoms in idiopathic hypersomnia: beyond excessive sleepiness," Sleep Res. (2010) 19, 525-534.
Vickers, M.D., "Gammahydroxybutyric Acid." Int. Anesth. Clinic (1969); 7 (1): 75-89.

(56) References Cited

OTHER PUBLICATIONS

Vogel et al., "Toxicologic/transport properties of NCS-382, a γ-hydroxybutyrate (GHB) receptor ligand, in neuronal and epithelial cells: Therapeutic implications for SSADH deficiency, a GABA metabolic disorder," Toxicol In Vitro, 2018, 46:203-212 (Epub 2017).
Walden et al., "The Effect of Ethanol on the Release of Opioids 30 from Oral Sustained-Release Preparations," Drug Development and Industrial Pharmacy, 2007, 33:10, 1101-1111.
Wermuth (Ed.), The Practice of Medicinal Chemistry, Academic Press, Third Edition, "Preparation of Water-Soluble Compounds Through Salt Formulation," Chapter 37, 2008, p. 758, 6 pages.
World Health Organization, "Annex 7: Multisource (generic) pharmaceutical products: guidelines on registration requirements to establish interchangeability," WHO Expert Committee on Specifications for Pharmaceutical Preparations Fortieth Report, pp. 347-390, 2006, retrieved from http://apps.who.int/prequal/info_general/documents/TRS937/WHO_TRS_937_eng.pdf #page=359.
Yamada, Y., "Effect of Butyrolactone and Gamma-Hydroxybutyrate on the EEG and Sleep Cycle in Man," Electroencephalography and Clinical Neurophysiology (1967); 22 (6): 558-562.
Zheng (Ed.), "Formulation and Analytical Development for Low-Dose Oral Drug Products," John Wiley & Sons, Inc., Hoboken, New Jersey, Table 4.1, p. 65, 2009, 3 pages.
Baumann et al., "Challenges in Diagnosing Narcolepsy without Cataplexy: A Consensus Statement," Sleep 2014;37(6):1035-1042.
Billiard and Sonka, "Idiopathic Hypersomnia: Historical Account, Critical Review of Current Tests and Criteria, Diagnostic Evaluation in the Absence of Biological Markers and Robust Electrophysiological Diagnostic Criteria," Nature and Science of Sleep 2022:14 311-322.
Ciccone, I., "Despite Missing Primary End Point, Pitolisant Shows Positive Outcomes in Phase 3 INTUNE Trial for Idiopathic Hypersomnia," NeurologyLive, Oct. 17, 2023, 5 pages, retrieved from https://www.neurologylive.com/view/despite-missing-primary-end-point-pitolisant-shows-positive-outcomes-phase-3-intune-trial-idiopathic-hypersomnia.
ClinicalTrials.gov Identifier NCT00087555, Trial Comparing the Effects of Xyrem (Sodium Oxybate) with Placebo for the Treatment of Fibromyalgia, Results First Posted Jan. 10, 2012, 9 pages, retrieved from https://www.clinicaltrials.gov/ct2/show/record/NCT00087555?term=oxybate&type=Intr&cond=Fibromyalgia&draw=2.
ClinicalTrials.gov Identifier: NCT0359755, Sodium Oxybate in Idiopathic Hypersomnia (SODHI), Latest Update—May 16, 2019, retrieved from: https://clinicaltrials.gov/ct2/history/NCT03597555?V_3=View#StudyPageTop, 9 pages.
Dauvilliers et al., "Clinical considerations for the diagnosis of idiopathic hypersomnia," Sleep Medicine Reviews 66 (2022) 101709, 10 pages.
D'Souza et al., "A review of in vivo and in vitro aspects of alcohol-induced dose dumping" AAPS Open (2017) 3:5, 20 pages.
Germain et al., "Sleep-specific mechanisms underlying post-traumatic stress disorder: integrative review and neurobiological hypotheses," Sleep Med Rev 2008;12(3): 185-195 (16 pages).
Guilleminault, et al., "Excessive daytime sleepiness: A challenge for the practicing neurologist" Brain (2001) 124: 1482-1491.

Harmony Biosciences, LLC, Wakix® (pitolisant) tablets, for oral use, Prescribing Information, Jun. 2024, 21 pages.
International Search Report and Written Opinion for International Application No. PCT/EP2022/078269 dated Jan. 31, 2023, 14 pages.
International Search Report and Written Opinion for International Application No. PCT/EP2023/050494 dated Apr. 17, 2023, 14 pages.
International Search Report and Written Opinion for International Application No. PCT/US2021/055426, dated Apr. 11, 2022, 19 pages.
International Search Report and Written Opinion of the International Searching Authority for International Application No. PCT/US2021/054179, dated Jan. 17, 2022, 15 pages.
Jazz Pharmaceuticals, Inc., "Xyrem® (sodium oxybate) oral solution, CIII," Highlights of Prescribing Information, Revised, Sep. 2016, 31 pages.
Jazz Pharmaceuticals, "Xyrem® Dosing & Titrating Information for Adults | Xyrem® for HCPs", May 9, 2021, 8 pages, retrieved from https://web.archive.org/web/20210509203007/https://www.xyremhcp.com/xyrem-dosing-and-titrating-adults.
Maski et al., "Treatment of central disorders of hypersomnolence: an American Academy of Sleep Medicine clinical practice guideline," Journal of Clinical Sleep Medicine, Sep. 1, 2021, vol. 17, No. 9, pp. 1881-1893.
Moldofsky et al., "Effects of Sodium Oxybate on Sleep Physiology and Sleep/Wake-related Symptoms in Patients with Fibromyalgia Syndrome: A Double-blind, Randomized, Placebo-controlled Study," Journal of Rheumatology, Aug. 3, 2010, vol. 37(10), pp. 2156-2166.
Rosiaux, Y., et al., "Ethanol-resistant polymeric film coatings for controlled drug delivery", Journal of Controlled Release, Jul. 2013, vol. 169, pp. 1-9.
Ross et al., "Sleep Disturbance as the Hallmark of Posttraumatic Stress Disorder," Am J Psychiatry, Jun. 1989, 146(6):697-707.
Rotem et al., "Polysomnographic and Actigraphic Evidence of Sleep Fragmentation in Patients with Irritable Bowel Syndrome," Sleep, 2003, vol. 26, No. 6, pp. 747-752.
Taft et al., "Initial Assessment of Post-traumatic Stress in a US Cohort of Inflammatory Bowel Disease Patients," Inflamm. Bowel Dis., Sep. 2019, vol. 25, No. 9, pp. 1577-1585.
Thorpy et al., "Clinical considerations in the treatment of idiopathic hypersomnia," Sleep Medicine (2024) 119: 488-498.
U.S. Department of Health and Human Services et al., "Guidance for Industry SUPAC-MR: Modified Release Solid Oral Dosage Forms", Food and Drug Administration, CDER, Sep. 1997, CMC 8, 52 pages.
Wang, B. et al., Diagnosis and Treatment of Sleep and Respiratory Disorders, Military Medical Science Press, Sep. 30, 2002, pp. 193-194, and English translation, 6 pages.
Xyrem Product information, Sep. 8, 2015, retrieved from the Internet: https://www.ema.europa.eu/en/documents/product-information/yrem-epar-product-information_en.pdf [retrieved on Jan. 6, 2022], pp. 1-36.
Zhang et al., "Sleep in posttraumatic stress disorder: A systematic review and meta-analysis of polysomnographic findings," Sleep Medicine Reviews (2019) 48: 101210, 18 pages.

\* cited by examiner

METHODS OF TREATING IDIOPATHIC HYPERSOMNIA

CROSS-REFERENCE TO RELATED APPLICATIONS

This application claims the benefit of priority to U.S. Application Ser. No. 63/142,738, filed Jan. 28, 2021; U.S. Application Ser. No. 63/088,902, filed Oct. 7, 2020; U.S. Application Ser. No. 63/069,811, filed Aug. 25, 2020; U.S. Application Ser. No. 62/993,381, filed Mar. 23, 2020; and U.S. Application Ser. No. 62/979,667, filed Feb. 21, 2020 the contents of each of which are hereby incorporated by reference in their entireties for all purposes.

BACKGROUND

Gamma-hydroxybutyrate (GHB), also known as "oxybate," is an endogenous compound that is found in many human body tissues. GHB is present, for example, in the mammalian brain and other tissues. In the brain, the highest GHB concentration is found in the hypothalamus and basal ganglia and GHB is postulated to function as an inhibitory neurotransmitter (Snead and Morley, 1981, Brain Res. 227 (4): 579-89). The neuropharmacologic effects of GHB include increases in brain acetylcholine, increases in brain dopamine, inhibition of GABA-ketoglutarate transaminase and depression of glucose utilization, but not oxygen consumption in the brain. GHB treatment substantially reduces the signs and symptoms of narcolepsy, i.e., daytime sleepiness, cataplexy, sleep paralysis, and hypnagogic hallucinations. In addition, GHB increases total sleep time and REM sleep, and it decreases REM latency, reduces sleep apnea, and improves general anesthesia (see U.S. Pat. Nos. 6,472,431; 6,780,889; 7,262,219; 7,851,506; 8,263,650; and 8,324,275, the disclosure of each of which is incorporated by reference in its entirety for all purposes).

Idiopathic hypersomnia (IH) is a rare disorder of central hypersomnolence characterized by severe excessive daytime sleepiness (EDS) occurring almost daily for at least 3 months, and timing of nocturnal sleep. Patients with IH face many disorder-associated challenges such as difficulty securing and sustaining employment, altered cognition, attention deficit, symptoms of autonomic dysfunction (faintness, difficulties in regulating body temperature, headaches and palpitations) and significant safety risks when operating a motor vehicle.

There are currently no approved medications for the treatment of IH. Thus, there is a need in the art for methods of treating IH.

SUMMARY

In one aspect, the present disclosure provides methods of treating idiopathic hypersomnia using oxybate, preferably a mixture of salts of oxybate (a mixed salt oxybate). In some embodiments, the mixed salt oxybate comprises one or more of the following: calcium, sodium, potassium, and magnesium salts.

In some embodiments, the mixed salt oxybate comprises about 8% sodium oxybate, about 23% potassium oxybate, about 21% magnesium oxybate and about 48% calcium oxybate (mol. equiv. %).

In some embodiments, about 0.5 g-9 g of the mixed salt oxybate is administered per day. In some embodiments, about 0.5 g of the mixed salt oxybate is administered per day. In some embodiments, about 0.25 g of the mixed salt oxybate is administered twice per day. In some embodiments, about 0.17 g of the mixed salt oxybate is administered three times per day. In some embodiments, about 1.0 g of the mixed salt oxybate is administered per day. In some embodiments, about 0.5 g of the mixed salt oxybate is administered twice per day. In some embodiments, about 0.33 g of the mixed salt oxybate is administered three times per day. In some embodiments, about 1.5 g of the mixed salt oxybate is administered per day. In some embodiments, about 0.75 g of the mixed salt oxybate is administered twice per day. In some embodiments, about 0.50 g of the mixed salt oxybate is administered three times per day. In some embodiments, about 2.0 g of the mixed salt oxybate is administered per day. In some embodiments, about 1.0 g of the mixed salt oxybate is administered twice per day. In some embodiments, about 0.66 g of the mixed salt oxybate is administered three times per day. In some embodiments, about 2.5 g of the mixed salt oxybate is administered per day. In some embodiments, about 2.5 g of the mixed salt oxybate is administered once per day. In some embodiments, about 1.25 g of the mixed salt oxybate is administered twice per day. In some embodiments, about 0.83 g of the mixed salt oxybate is administered three times per day. In some embodiments, about 3.0 g of the mixed salt oxybate is administered per day. In some embodiments, about 3.0 g of the mixed salt oxybate is administered once per day. In some embodiments, about 1.5 g of the mixed salt oxybate is administered twice per day. In some embodiments, about 1.0 g of the mixed salt oxybate is administered three times per day. In some embodiments, about 3.5 g of the mixed salt oxybate is administered per day. In some embodiments, about 3.5 g of the mixed salt oxybate is administered once per day. In some embodiments, about 1.75 g of the mixed salt oxybate is administered twice per day. In some embodiments, about 1.16 g of the mixed salt oxybate is administered three times per day. In some embodiments, about 4.0 g of the mixed salt oxybate is administered per day. In some embodiments, about 4.0 g of the mixed salt oxybate is administered once per day. In some embodiments, about 2.0 g of the mixed salt oxybate is administered twice per day. In some embodiments, about 1.32 g of the mixed salt oxybate is administered three times per day. In some embodiments, about 4.5 g of the mixed salt oxybate is administered per day. In some embodiments, about 4.5 g of the mixed salt oxybate is administered once per day. In some embodiments, about 2.25 g of the mixed salt oxybate is administered twice per day. In some embodiments, about 1.5 g of the mixed salt oxybate is administered three times per day. In some embodiments, about 5 g of the mixed salt oxybate is administered per day. In some embodiments, about 5 g of the mixed salt oxybate is administered once per day. In some embodiments, about 2.5 g of the mixed salt oxybate is administered twice per day. In some embodiments, about 5.5 g of the mixed salt oxybate is administered per day. In some embodiments, about 5.5 g of the mixed salt oxybate is administered once per day. In some embodiments, about 2.75 g of the mixed salt oxybate is administered twice per day. In some embodiments, about 6 g of the mixed salt oxybate is administered per day. In some embodiments, about 6 g of the mixed salt oxybate is administered once per day. In some embodiments, about 3.0 g of the mixed salt oxybate is administered twice per day. In some embodiments, about 2.0 g of the mixed salt oxybate is administered three times per day. In some embodiments, about 7.5 g of the mixed salt oxybate is administered per day. In some embodiments, about 3.75 g of the mixed salt oxybate is administered twice per day. In some embodiments, about 2.5 g of the mixed salt oxybate is administered three times per day. In some embodiments, about 9.0 g of the mixed salt oxybate is administered per day. In some embodiments, about 4.5 g of the mixed salt oxybate is administered twice per day. In some embodiments, about 3.0 g of the mixed salt oxybate is administered three times per day.

In some embodiments, the mixed salt oxybate is administered when the patient wants to go to sleep. In some embodiments, the mixed salt oxybate is administered at bedtime and about 2.5 h-4 h after the bedtime administration. In some embodiments, the mixed salt oxybate is administered after a period of sleep.

In some embodiments, mixed salt oxybate is in a liquid. In some embodiments, the concentration of the mixed salt in the liquid is about 0.5 g/mL. In other embodiments, mixed salt oxybate is a solid.

DEFINITIONS

Figure 1:
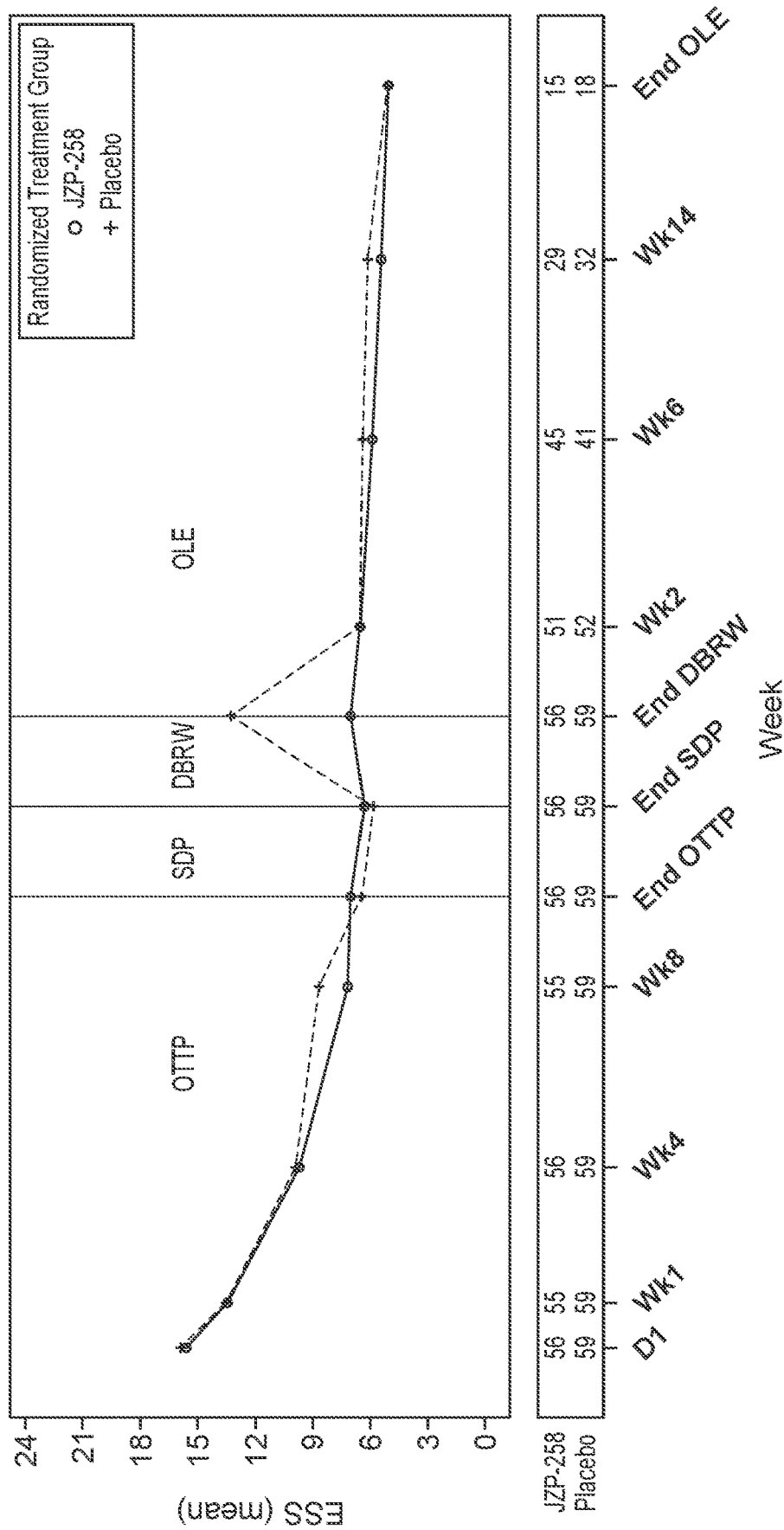
FIG. 1 shows the change in mean Epworth Sleepiness Scale (ESS) score during the study described in Example 1 for patients treated with JZP-258 and patients treated with placebo.

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms "administer," "administering" or "administration" as used herein refer to administering a compound or pharmaceutically acceptable salt of the compound or a composition or formulation comprising the compound or pharmaceutically acceptable salt of the compound to a patient.

As used herein, the term "gamma-hydroxybutyrate" (GHB) or "oxybate" refers to the negatively charged or anionic form (conjugate base) of gamma-hydroxybutyric acid. GHB has the following structural formula:

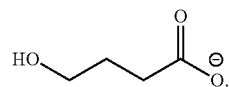

As used herein, the term "gamma-hydroxybutyric acid" (GBA) refers to the protonated form (conjugate acid) of gamma-hydroxybutyrate. GBA has the following structural formula:

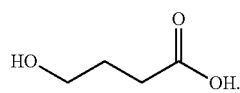

Salt forms of GHB are disclosed in U.S. Pat. Nos. 8,591,922; 8,901,173; 9,132,107; 9,555,017; and 10,195,168, which are hereby incorporated by reference in their entireties for all purposes.

The terms "effective amount" and "therapeutically effective amount" are used interchangeably in this disclosure and refer to an amount of a compound, or a salt thereof, that, when administered to a patient, is capable of performing the intended result. For example, an effective amount of a mixed salt oxybate is that amount which is required to reduce cataplexy in a patient. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The term "equivalent" when comparing Na.GHB and mixed salts forms contains the same amount of GHB within about 5% (by weight %). In preferred embodiments, a liquid formulation of a mixed salt is equivalent to the Na.GHB-containing liquid formulation Xyrem (which contains 0.409 g/mL of GHB).

In preferred embodiments, a liquid formulation of a mixed salt contains 0.234 g/mL of calcium oxybate, 0.130 g/mL of potassium oxybate, 0.096 g/mL of magnesium oxybate, and 0.040 g/mL of sodium oxybate.

As used herein, the term "patient" refers to a mammal, particularly a human.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "carrier" encompasses solvents, dispersion media, coatings, antibacterial and antifungal agents, isotonic and absorption delaying agents and the like. The use of carriers for active pharmaceutical ingredients is well known in the art. Insofar as any conventional media or agent is incompatible with the active ingredient, its use in the therapeutic compositions is not appropriate.

The term "therapeutic effect" as used herein refers to a desired or beneficial effect provided by the method and/or the composition. For example, the method for treating IH provides a therapeutic effect when the method reduces at least one symptom of IH, such as excessive daytime sleepiness, difficulty waking after sleep or cognitive dysfunction.

The term "treating" as used herein with regard to a patient, refers to improving at least one symptom of the patient's disorder. Treating can be curing, improving, or at least partially ameliorating a disorder.

The terms "substitute", "switch", "change", "transition" and "exchange" are used interchangeably in the context of the present disclosure.

The term "salt" or "salts," as used herein, refers to a compound formed by the interaction of an acid and a base, the hydrogen atoms of the acid being replaced by the positive ion or cation of the base. Pharmaceutically acceptable salts include inorganic acids such as, for example, hydrochloric or phosphoric acids, or such organic acids as malic, acetic, oxalic, tartaric, mandelic, and the like. Salts formed can also be derived from inorganic bases such as, for example, sodium, potassium, silicates, ammonium, calcium, or ferric hydroxides, and such organic bases as isopropylamine, trimethylamine, histidine, procaine and the like. In certain preferred embodiments, the salt is formed from an inorganic base that is a metal, for example, an alkali metal, such as lithium, potassium, sodium, or the like, an alkaline earth metal, such as magnesium, calcium, barium, or the like, or aluminum or zinc. Other salts may comprise ammonium. Alkali metals, such as lithium, potassium, sodium, and the like, may be used, preferably with an acid to form a pH adjusting agent. Examples of pharmaceutically acceptable base addition salts include those derived from inorganic bases like sodium hydroxide, potassium hydroxide, magnesium hydroxide, calcium hydroxide, or ammonium hydroxide, and the like (See, e.g., Berge et al., 1977, J. Pharm. Sci. 66: 1, U.S. Pat. Nos. 6,472,431 and 8,591,922).

As used herein, the terms "salt of GHB" or "salts of GHB," as used herein, refer to a compound formed by the interaction of gamma-hydroxybutyric acid (the conjugate acid of GHB) with a base, for example, NaOH, KOH, $Mg(OH)_2$, and $Ca(OH)_2$, and the like, the hydrogen atoms of the acid being replaced by the positive ion or cation of the base. Such salts may include, for example, sodium oxybate ("Na.GHB"), potassium oxybate ("K.GHB"), magnesium oxybate ("Mg.$(GHB)_2$"), and calcium oxybate ("Ca.$(GHB)_2$"), and the like. It will be understood by those skilled in the art that such salts may be in solid form, or such salts may be in partially or fully solvated form, for example, as when dissolved in an aqueous medium. It will be further understood by those skilled in the art, that, depending on the solubility of the salt in the aqueous medium, that the salt may be present in the aqueous medium as solvated cation(s) and anion(s), or as a precipitated solid.

The term "oxybate dosing strength" refers to the amount of GHB in a particular dose (e.g., each mL of Xyrem contains 0.5 g of sodium oxybate, which is equivalent to a 0.409 g/mL oxybate dosing strength). Although throughout the present disclosure, the oxybate dosing strength in a composition is generally expressed in terms of the amount of oxybate present in a composition, the present disclosure contemplates embodiments where the oxybate dosing strength is expressed in the Equivalent Concentration of GBA that is contained in the dose.

The Equivalent Concentration of GBA in a compositions may be calculated by the following formula:

$$\text{Equivalent Concentration of } GBA = \frac{\text{Concentration of } GHB \text{ in (g/mL)} \times 104.1 \left(\text{Formula Weight of } GBA, \frac{g}{mol}\right)}{103.1 \left(\text{Formula Weight of } GHB \left(\frac{g}{mol}\right)\right)}$$

Thus, each mL of Xyrem contains 0.5 g of sodium oxybate, which is equivalent to an Equivalent Concentration of GBA of 0.413 g/mL.

The term "JZP-258" as used herein refers to a solution containing the mixed salt oxybate comprising about 8% sodium oxybate, about 23% potassium oxybate, about 21% magnesium oxybate and about 48% calcium oxybate (% mol. equiv. of GHB) and having a GHB concentration of 0.409 g/mL (or, expressed another way, an Equivalent Concentration of GBA of 0.413 g/mL). The following table describes the % mol. equiv., wt/vol %, and absolute amount of sodium oxybate, potassium oxybate, magnesium oxybate and calcium oxybate in representative doses of JZP-258.

|  | % mol equivalent | wt/wt % | Amount in 1 g JZP-258 | Amount in 9 g JZP-258 |
| --- | --- | --- | --- | --- |
| Na•GHB | 8 | 8 | 80 mg | 720 mg |
| K•GHB | 23 | 25.5 | 255 mg | 2,295 mg |
| Mg•$(GHB)_2$ | 21 | 19.5 | 195 mg | 1,755 mg |
| Ca•$(GHB)_2$ | 48 | 47 | 470 mg | 4,230 mg |

The term "mixed salts" or "mixed salt oxybate," as used herein, refers to salts of GHB where two, three, four or more different cations are present in combination with each other in a composition. Such mixtures of salts may include, for example, salts selected from the group consisting of Na.GHB, K.GHB, Mg.$(GHB)_2$, and Ca.$(GHB)_2$. Mixed salt oxybates are described in U.S. Pat. Nos. 8,591,922; 8,901,173; 9,132,107; 9,555,017; and 10,195,168, the contents of which is hereby incorporated by reference it entirety for all purposes.

The term "wt/wt %," are used herein, refers to the normalized weight percent of a particular salt in a salt mixture.

The term "wt/wt % ratio," as used herein, refers to the ratio of wt/wt % values in a mixture of salt. For example, where the salts Na.GHB, K.GHB, Mg.$(GHB)_2$, and Ca.$(GHB)_2$ are present in a wt/wt %'s of 8%, 25.5%, 19.5% and 47%, respectively, the wt/wt % ratio of Na.GHB, K.GHB, Mg.$(GHB)_2$, and Ca.$(GHB)_2$ in the mixture is 8%:25.5%:19.5%:47%.

The term, "formulation," as used herein, refers to a stable and pharmaceutically acceptable preparation of a pharmaceutical composition disclosed herein.

The term, "liquid formulation," as used herein, refers to a water-based formulation, in particular, a formulation that is an aqueous solution.

DETAILED DESCRIPTION

Idiopathic Hypersomnia

Idiopathic hypersomnia (IH) is a rare disorder of central hypersomnolence characterized by severe excessive daytime sleepiness (EDS) occurring almost daily for at least 3 months, despite normal quality, quantity, and timing of nocturnal sleep (American Academy of Sleep Medicine International Classification of Sleep Disorders, Third Edition [AASM 2014]). The pathophysiology of idiopathic hypersomnia remains to be elucidated. The clinical phenotype of IH is heterogeneous based on presence or absence of ancillary symptoms, most notably of which include prolonged sleep time and sleep inertia (Basetti and Aldrich (1997), Idiopathic hypersomnia. A series of 42 patients, *Brain: A Journal of Neurology,* 120(8), 1423-35 [Basetti and Aldrich 1997]; Anderson et al. (2007), Idiopathic hypersomnia: a study of 77 cases, *Sleep,* 30(10), 1274-81 [Anderson 2007]; Ali et al. (2009), Idiopathic hypersomnia: clinical features and response to treatment, *Journal of Clinical Sleep Medicine,* 5(6), 562-68 [Ali 2009]; Ahmed et al. (2016), Overview of Central Disorders of Hypersomnolence, *Reference Module in Neuroscience and Biobehavioral Psychology*; Evangelista et al. (2018), Update on treatment for idiopathic hypersomnia, *Expert Opinion on Investigational Drugs,* 27(2), 187-92 [Evangelista 2018]; Leu-Semenescu et al. (2016), Benefits and risk of sodium oxybate in idiopathic hypersomnia versus narcolepsy type 1: a chart review, *Sleep Medicine,* 17, 38-44 [Leu-Semenescu 2016]). Nocturnal sleep time and 24-hour sleep time are often prolonged (e.g., ≥11 hours) in patients with IH, and can be used to confirm the diagnosis (AASM 2014). Sleep inertia or "sleep drunkenness" defined as "prolonged difficulty waking up with repeated returns to sleep, irritability, automatic behavior, and confusion" is reported in 36 to 66% of patients (AASM 2014; Vernet et al. (2010), Subjective symptoms in idiopathic hypersomnia: beyond excessive sleepiness, *Journal of Sleep Research,* 19(4), 525-34; Roth et al. (1972), Hypersomnia with sleep drunkenness, *Archives of General Psychiatry,* 26(5), 456-62). The sleep inertia experienced by patients with IH represents a clinical challenge because it is difficult for some patients to awaken enough to take their stimulant medication (Trotti L M (2017), Idiopathic Hypersomnia, *Sleep Medicine Clinics* 12(3), 331-44 [Trotti 2017]). Other less specific features of IH include sleep paralysis and sleep hallucinations (hypnagogic or hypnopompic hallucinations occurring at the transition from wake to sleep or sleep to wake), which are present in approximately 20 and 25% of patients, respectively (Khan and Trotti (2015), Central disorders of hypersomnolence, *Chest,* 148(1), 262-73 [Khan and Trotti 2015]). The majority of patients with IH have symptoms that remain stable over many years and require long term treatment, but spontaneous remission is seen in a minority of patients with IH (11-33%) within up to 5.5 years after diagnosis (Anderson 2007; Basetti and Aldrich 1997; Kim et al. (2016), Different fates of excessive daytime sleepiness: survival analysis for remission, *Acta Neurologica Scandinavica,* 134(1), 35-41).

Idiopathic hypersomnia is one of three central disorders of persistent hypersomnolence not associated with another illness or substance; narcolepsy type 1 and narcolepsy type 2 comprise the other two (AASM 2014). Features that distinguish IH from narcolepsy type 1 include the absence of cataplexy and normal levels of hypocretin according to the ICSD-3 and a review by Billiard M (2017), Epidemiology of central disorders of hypersomnolence, *Reference Module in Neuroscience and Biobehavioral Psychology* [Billiard 2017]. Distinguishing IH from narcolepsy type 2 is more challenging, as clinical features can be very similar. The diagnostic criteria for IH and narcolepsy type 2 overlap with respect to irrepressible need to sleep or daytime lapses into sleep and the absence of cataplexy. The diagnostic criteria for narcolepsy type 2 and IH differ with respect to findings on sleep diagnostic testing. The diagnostic criteria for narcolepsy type 2 require either a sleep onset rapid eye movement period (SOREMP) on Polysomnography (PSG) or ≥2 SOREMPs on multiple sleep latency test (MSLT), and a mean sleep latency ≤8 minutes on MSLT; the diagnostic criteria for IH require the absence of a SOREMP on PSG and ≤1 SOREMP on MSLT, and either a mean sleep latency ≤8 minutes on MSLT or total 24-hour sleep time ≥660 minutes (Billiard 2017, AASM 2014). Idiopathic hypersomnia is a diagnosis of exclusion, and it is important that physicians rule out other conditions that can cause hypersomnolence (e.g. sleep apnea, narcolepsy, circadian rhythm disorders, sleep deprivation, medical and psychiatric disorders) (Khan and Trotti 2015).

For more information about IH, see the following references which are hereby incorporated by reference in their entireties: Lopez et al. (2017), French consensus. Management of patients with hypersomnia: Which strategy?, *Revue Neurologique,* 173(1), 8-18; Pizza et al. (2013), Polysomnographic study of nocturnal sleep in idiopathic hypersomnia without long sleep time, *Journal of Sleep Research,* 22(2), 185-96.; Billiard and Sonka (2016), Idiopathic hypersomnia, *Sleep Medicine Reviews,* 29, 23-33; Delrosso et al. (2014), Manual Characterization of Sleep Spindle Index in Patients with Narcolepsy and Idiopathic Hypersomnia, *Sleep Disorders,* 2014; Evangelista et al. (2018) Update on treatment for idiopathic hypersomnia, *Expert Opin Investig Drugs,* 27(2):187-192; Leu-Semenescu et al. (2016), Benefits and risk of sodium oxybate in idiopathic hypersomnia versus narcolepsy type 1: a chart review, *Sleep Med.,* 17:38-44; Mignot E J (2012), A practical guide to the therapy of narcolepsy and hypersomnia syndromes, *Neurotherapeutic,* 9(4), 739-52; Ali et al. (2009), Idiopathic hypersomnia: clinical features and response to treatment, *Journal of Clinical Sleep Medicine,* 5(6), 562-68.

The EDS and other symptoms experienced by patients with IH can negatively impact quality of life, ability to sustain employment, and create a safety risk when operating a motor vehicle. Compared with controls, patients with IH report increased activity limitations due to both physical capabilities and emotional problems, decreased energy, decreased social functioning, increased perception of general health problems, and increased feelings of depression and anxiety (Ozaki et al. (2008), Health-related quality of life among drug-naïve patients with narcolepsy with cataplexy, narcolepsy without cataplexy, and idiopathic hypersomnia without long sleep time, *Journal of Clinical Sleep Medicine,* 4(6), 572 [Ozaki 2008]). Patients with IH face many disorder-associated challenges that interfere with their ability to secure and sustain employment, including tardiness and absenteeism due to debilitating EDS and sleep inertia that cannot be effectively mitigated through napping, increasing sleep time, or typical strategies to awaken in the morning such as use of alarm clocks, light exposure, or routines (Philip (2001), Is there a link between subjective daytime somnolence and sickness absenteeism? A study in a working population, *J Sleep Res.* 10(2):111-5; Vernet et al. (2010), Subjective symptoms in idiopathic hypersomnia: beyond excessive sleepiness, *Journal of Sleep Research,* 19(4), 525-34 [Vernet 2010]). In addition to the potential for absenteeism at work, performance at work may be compromised in patients with IH due to EDS and other aspects of the disorder process including altered cognition, attention deficit, and symptoms of autonomic dysfunction (faintness, difficulties in regulating body temperature, headaches and palpitations) (Oosterloo et al. (2006) Possible confusion between primary hypersomnia and adult attention-deficit/hyperactivity disorder, *Psychiatry Res.* 143(2-3):293-7; Vernet 2010). Lastly, the symptoms associated with IH can pose significant risks when operating a motor vehicle. In a large cross-sectional study of 282 patients with central disorders of hypersomnolence and 470 healthy controls, patients with central disorders of hypersomnolence reported a 2-fold increase in the prevalence of vehicular accidents in the preceding 5 years compared with controls (Pizza et al. (2015), Car Crashes and Central Disorders of Hypersomnolence: A French Study, *PLoS One.* 2015; 10(6):e0129386. Published 2015 Jun. 8.). In the same study, the risk of recent vehicular accidents among patients with IH was 2.04 times that of the healthy control population. In a separate Japanese study, 50% of drug naïve patients with IH without long sleep time reported accidents or near misses within the previous 5 years (Ozaki 2008).

There are currently no approved medications for the treatment of IH. The pathophysiology is unknown, and the disorder is treated symptomatically. Few large randomized controlled trials have evaluated therapies for EDS in IH, and treatment is guided by expert opinion (Khan and Trotti 2015; Saini and Rye (2017), Hypersomnia: evaluation, treatment, and social and economic aspects, *Sleep Medicine Clinics,* 12(1), 47-60; Trotti 2017; Evangelista 2018). Thus, despite somewhat different clinical features in patients with IH and narcolepsy, the same medications and treatment approaches that are used to treat narcolepsy are recommended off-label for the management of EDS in IH (Evangelista 2018, Morgenthaler et al. (2007), Practice Parameters for the Treatment of Narcolepsy and other Hypersomnias of Central Origin An American Academy of Sleep Medicine Report, *Sleep,* 30(12), 1705-1711. These include wake-promoting agents and traditional stimulants such as modafinil and armodafinil (Lavault et al. (2011), Benefit and risk of modafinil in idiopathic hypersomnia vs. narcolepsy with cataplexy, *Sleep Medicine,* 12(6), 550-56; Anderson 2007), amphetamine, and methylphenidate (Anderson 2007). Other agents that have been used or tested in clinical trials in patients with IH include sodium oxybate (Leu-Semenescu 2016), pitolisant (Leu-Semenescu et al., (2014), Effects of pitolisant, a histamine H3 inverse agonist, in drug-resistant idiopathic and symptomatic hypersomnia: a chart review, *Sleep Med.* 15(6):681-7), clarithromycin (Trotti et al. (2014), Improvement in daytime sleepiness with clarithromycin in patients with GABA-related hypersomnia: Clinical experience, *J Psychopharmacol.* 28(7): 697-702.), flumazenil (Trotti et al. (2016), Flumazenil for the Treatment of Refractory Hypersomnolence: Clinical Experience with 153 Patients, *Journal of clinical sleep medicine,* 12(10) 1389-1394.), levothyroxine (Shinno et al. (2009), Successful treatment with levothyroxine for idiopathic hypersomnia patients with subclinical hypothyroidism, *General Hospital Psychiatry,* 31(2), 190-93), mazindol (Nittur et al. (2013), Mazindol in narcolepsy and idiopathic and symptomatic hypersomnia refractory to stimulants: a long-term chart review, Sleep Medicine, 14(1), 30-36), and pentetrazol (Clinicaltrials.gov NCT02512588).

Oxybate

Sodium oxybate (Na.GHB), commercially sold as Xyrem®, is approved for the treatment of cataplexy or excessive daytime sleepiness in patients 7 years of age or older with narcolepsy. Administration of the approved daily dose of Xyrem® (6-9 grams per night administered orally) results in the patient ingesting from 1100-1638 mg of sodium daily. The American Heart Association has recommended a daily sodium intake of less than 2300 mg and an "ideal" daily intake of <1500 mg (AHA 2017 (https://www.heart.org/-/media/data-import/downloadables/8/2/0/pe-abh-why-should-i-limit-sodium-ucm_300625.pdf); Whelton et al. (2012), Sodium, blood pressure, and cardiovascular disorder: further evidence supporting the American Heart Association sodium reduction recommendations, *Circulation,* 126(24):2880-9) and a recent report from The National Academies of Science, Engineering, and Medicine (2019) advises adults to "reduce intake if above 2300 mg/day" based on strong causal evidence of cardiovascular disorder risk above this level. Thus, Xyrem® administration provides a sodium intake that makes up a substantial amount of the recommended daily intake goals, which renders adherence to daily sodium intake goals challenging since—even without the consideration of Xyrem—the average daily sodium intake for Americans ≥2 years of age is >3400 mg (US Department of Agriculture, Agricultural Research Service. Nutrient intakes from food: mean amounts consumed per individual, by gender and age, in the United States, 2009-2010. In: What We Eat in America, NHANES 2009-2010. Washington, DC: US Department of Agriculture, Agricultural Research Service; 2012.).

Mixed Salt Oxybate

JZP-258 (a preferred embodiment of the present disclosure) was developed to provide the same treatment benefits as Xyrem with substantially less sodium.

JZP-258 is a mixed salt oxybate that contains calcium oxybate, magnesium oxybate, potassium oxybate, and sodium oxybate, and it provides 87-131 mg of sodium when administered in the dose range of 6-9 grams nightly. This amount is 92% less sodium than that provided by Xyrem® administration at an equivalent dose. Though important for every person, daily sodium intake goals are a vital consideration for all patients with the lifelong disorder of narcolepsy, given the increased presence of multiple cardiovascular comorbidities, including hypertension, congestive heart failure, and myocardial infarction (Jennum et al. (2013), Comorbidity and mortality of narcolepsy: a controlled retro- and prospective national study. *Sleep,* 36(6), 835-40; Ohayon M M (2013), Narcolepsy is complicated by high medical and psychiatric comorbidities: a comparison with the general population, *Sleep Medicine,* 14(6), 488-92; and Black et al. (2017), Medical comorbidity in narcolepsy: findings from the Burden of Narcolepsy Disease (BOND) study, *Sleep Medicine,* 33, 13-18).

The following patents, publications and application are related to the present disclosure and are hereby incorporated by reference in their entireties for all purposes: U.S. Pat. Nos. 6,472,431; 6,780,889; 7,262,219; 8,263,650; 8,461, 203; 8,859,619; 9,539,330; 7,851,506; 8,324,275; 8,952, 062; 8,731,963; 8,772,306; 8,952,029; 9,050,302; 9,486, 426; 10,213,400; 8,591,922; 8,901,173; 9,132,107; 9,555, 017; 10,195,168; 8,778,301; 9,801,852; 8,771,735; 8,778, 398; 9,795,567; U.S. Patent Publication Nos. US 2018/0042855, and U.S. application Ser. Nos. 16/688,797, 62/769,380 and 62/769,382.

In some embodiments, the methods of the present disclosure comprise administering sodium oxybate or a mixed salt oxybate to a patient in need thereof (such as a patient with IH). In some embodiments, the mixed salt oxybate comprises gamma-hydroxybutyrate (GHB) and three or four or more pharmaceutically acceptable cations of an alkali metal or an alkaline earth metal. In some embodiments, the mixed salt oxybate comprises GHB and more than one pharmaceutically acceptable cations of an alkali metal or an alkaline earth metal.

In some embodiments, the mixed salt oxybate comprises GHB and two, three, or four cations selected from the group consisting of $Na^+$, $K^+$, $Mg^{+2}$, and $Ca^{+2}$. In some embodiments, mixed salt oxybate comprises GHB and all three cations selected from the group consisting of $K^+$, $Mg^{+2}$, and $Ca^{+2}$. In some embodiments, the mixed salt oxybate does not contain $Na^+$, or comprises less than 100% of $Na^+$.

In some embodiments, the mixed salt oxybate comprises two, three, or four salts selected from the group consisting of a sodium salt of hydroxybutyrate (Na.GHB), a potassium salt of gamma-hydroxybutyrate (K.GHB), a magnesium salt of gamma-hydroxybutyrate (Mg.(GHB)$_2$), and a calcium salt of gamma-hydroxybutyrate (Ca.(GHB)$_2$). In some embodiments, the mixed salt oxybate comprises varying weight/weight percentages (wt/wt %) of Na.GHB, K.GHB, Mg.(GHB)$_2$, and Ca.(GHB)$_2$.

In some embodiments, any of the salts, such as the Na.GHB salt, the K.GHB salt, the Mg.(GHB)$_2$ salt or the Ca.(GHB)$_2$, is present in about 1%-5%, about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, about 90%-95%, or about 95%-100% (wt/wt %). In some embodiments, the Na.GHB salt is present in a wt/wt % of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (wt/wt %). In some embodiments, the Na.GHB salt is absent.

In some embodiments, where the mixed salt oxybate comprises a mixture of Na.GHB, K.GHB, Mg.(GHB)$_2$, and Ca.(GHB)$_2$, the Na.GHB salt is present in a wt/wt % of about 1%-15%, 5%-10%, or about 8%; the K.GHB salt is present in a wt/wt % of about 10%-30%, 15%-25%, or about 25.5%; the Mg.(GHB)$_2$ salt is present in a wt/wt % of about 10%-30%, 15%-25%, or about 19.5%; and the Ca.(GHB)$_2$ salt is present in a wt/wt % of about 30%-60%, 40%-50, or about 47% (wt/wt %).

In some embodiments, the mixed salt oxybate comprises about 8% of sodium oxybate (wt/wt %), about 25.5% of potassium oxybate (wt/wt %), about 19.5% of magnesium oxybate (wt/wt %) and about 47% of calcium oxybate (wt/wt %). In some embodiments, where the mixed salt oxybate comprises a mixture of Na.GHB, K.GHB, Mg.(GHB)$_2$, and Ca.(GHB)$_2$, the Na.GHB, K.GHB, Mg.(GHB)$_2$, and Ca.(GHB)$_2$ salts are present in a wt/wt % ratio of about 8:25.5:19.5:47, respectively.

In some embodiments, a mixed salt oxybate of the present disclosure is dissolved in a liquid (such as water) to provide a pharmaceutical composition and the concentration of the mixed salt oxybate is expressed in terms of the wt/vol %. In some embodiments, where the mixed salt oxybate comprises a mixture of Na.GHB, K.GHB, Mg.(GHB)$_2$, and Ca.(GHB)$_2$, the Na.GHB salt is present in a wt/vol % of about 1%-15%, 5%-10%, or about 8%; the K.GHB salt is present in a wt/vol % of about 10%-30%, 15%-25%, or about 26%; the Mg.(GHB)$_2$ salt is present in a wt/vol % of about 10%-30%, 15%-25%, or about 19.2%; and the Ca.(GHB)$_2$ salt is present in a wt/vol % of about 30%-60%, 40%-50, or about 46.8% (wt/vol %).

In some embodiments, the liquid pharmaceutical composition containing the mixed salt oxybate comprises about 8% of sodium oxybate (wt/vol %), about 26.0% of potassium oxybate (wt/vol %), about 19.2% of magnesium oxybate (wt/vol %) and about 46.8% of calcium oxybate (wt/vol %).

In some embodiments, the mixed salt oxybate comprises varying percentages of oxybate, expressed as % molar equivalents (% mol. equiv.) of Na.GHB, K.GHB, Mg.(GHB)$_2$, and Ca.(GHB)$_2$. The terms "% molar equivalents" and "% mol. equiv.," as used herein, refer to molar composition of salts expressed as a percent of GHB equivalents. Those skilled in the art will understand that as each GHB unit is considered to be one molar equivalent, the monovalent cations, $Na^+$ and $K^+$, have one molar equivalent per salt, and the divalent cations, $Mg^{+2}$ and $Ca^{+2}$, have two molar equivalents per salt. See U.S. Pat. Nos. 8,591,922; 8,901,173; 9,132,107; 9,555,017; 10,195,168 for amounts of % mol. equiv. useful in the present disclosure.

In some embodiments, any of the salts, such as the Na.GHB salt, the K.GHB salt, the Mg.(GHB)$_2$ salt or the Ca.(GHB)$_2$, is present in about 1%-5%, about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, about 90%-95%, or about 95%-100% (% mol. equiv.). In some embodiments, the Na.GHB salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (% mol. equiv.). In some embodiments, the Na.GHB salt is absent.

In some embodiments, where the mixed salt oxybate comprises a mixture of Na.GHB, K.GHB, Mg.(GHB)$_2$, and Ca.(GHB)$_2$, the Na.GHB salt is present in a % mol. equiv. of about 1%-15%, 5%-10%, or about 8%; the K.GHB salt is present in a % mol. equiv. of about 10%-30%, 15%-25%, or about 23%; the Mg.(GHB)$_2$ salt is present in a % mol. equiv. of about 10%-30%, 15%-25%, or about 21%; and the Ca.(GHB)$_2$ salt is present in a % mol. equiv. of about 30%-60%, 40%-50, or about 48% (% mol. equiv.).

In some embodiments, the mixed salt oxybate comprises about 8% mol. equiv. of sodium oxybate, about 23% mol. equiv. of potassium oxybate, about 21% mol. equiv. of magnesium oxybate and about 48% mol. equiv. of calcium oxybate. In some embodiments, where the mixed salt oxybate comprises a mixture of Na.GHB, K.GHB, Mg.(GHB)$_2$, and Ca.(GHB)$_2$, wherein the mixture comprises Na.GHB, K.GHB, Mg.(GHB)$_2$, and Ca.(GHB)$_2$ salts are present in a % mol. equiv. ratio of about 8:23:21:48, respectively.

In some embodiments, where the pharmaceutical composition comprises a mixture of Na.GHB, K.GHB, and Ca.(GHB)$_2$, the Na.GHB salt is present in a % mol. equiv. of about 5%-40%, the K.GHB salt is present in a % mol. equiv. of about 10%-40%, and the Ca.(GHB)$_2$ salt is present in a % mol. equiv. of about 20%-80%.

Pharmaceutical Compositions:

In some embodiments, the mixed salt oxybate is in the form of a pharmaceutical composition that is suitable for administration in the methods of the present disclosure. In some embodiments, the pharmaceutical composition comprises an aqueous solution. Other formulations can be solid formulations.

In some embodiments, the concentration of the mixture of salts of GHB in the liquid solution is about 50 mg/mL-950 mg/mL, about 250 mg/mL-750 mg/mL, about 350 mg/mL-650 mg/mL, or about 450 mg/mL-550 mg/mL. In some embodiments, the concentration of the mixture of salts of GHB in the solution is about 500 mg/mL. In some embodiments, the pH of the pharmaceutical composition is about 7.0-9.0, about 7.0-8.5, or about 7.3-8.5.

In some embodiments, the pharmaceutical composition is chemically stable and resistant to microbial growth. In some embodiments, the pharmaceutical composition does not need, and is free of preservatives. See U.S. Pat. Nos. 6,472,431; 6,780,889; 7,262,219; 8,263,650; 8,461,203 and others for a relationship between pH and GHB concentration and their effect on microbial growth.

In some embodiments, a pH adjusting or buffering agent may be added to the pharmaceutical composition. The choice of a pH adjusting or buffering agent may affect the resistance to microbial challenge and/or the stability of GHB, as measured by the reduction in assayable GHB. Pharmaceutical compositions of GHB, pH adjusted or buffered with malic acid are resistant to both microbial growth and chemical degradation of GHB, and are preferred. Other pH adjusting or buffering agents may be selected. Agents that adjust pH that are selected on this basis will undergo a taste testing study. However, any pH adjusting or buffering agent disclosed herein or as would be known to those skilled in the art is contemplated as being useful from the compositions or formulations disclosed herein. Of course, any salt, flavoring agent, excipient, or other pharmaceutically acceptable addition described herein or as would be known to those skilled in the art is contemplated as being useful for the compositions or formulations disclosed herein.

In some embodiments, the pH adjusting or buffering agent is an acid. In some embodiments, the pH adjusting or buffering agent is an inorganic acid or an organic acid. In some embodiments, the pH adjusting or buffering agent is selected from the group consisting of malic acid, citric acid, acetic acid, boric acid, lactic acid, hydrochloric acid, phosphoric acid, sulfuric acid, sulfonic acid, and nitric acid. In some embodiments, the pH adjusting or buffering agent is malic acid. See U.S. Pat. No. 6,472,431.

The aqueous solutions disclosed herein typically comprise an effective amount of GHB, which may be dissolved or dispersed in a pharmaceutically acceptable carrier and/or an aqueous medium.

Formulations

In some embodiments, the pharmaceutical compositions disclosed herein are provided in a formulation that is suitable for administration in the methods of the present disclosure.

In some embodiments, the formulation is a liquid formulation. In some embodiments, the formulation is a solid formulation. In some embodiments, the formulation is suitable for oral administration. See incorporated by reference U.S. Pat. Nos. 6,472,431; 6,780,889; 7,262,219; 8,263,650; 8,461,203, 8,591,922, 8,901,173, 9,132,107, 9,555,017, 9,795,567, 10,195,168, U.S. Ser. Nos. 16/688,797, 62/769,380 and 62/769,382 and U.S. Patent Publication No. 2018/0263936 for example. These patents present examples of flavoring agents, sweeteners, coloring agents, surfactants, carriers, excipients, binders, buffering compounds or agents and other formulation ingredients.

In some embodiments, the formulation is chemically stable and resistant to microbial growth. In some embodiments, the formulation is free of preservatives. In some embodiments, the level of gamma-butyrolactone (GBL) is 0.1% or less of the formulation.

In preferred embodiments, the formulation is a liquid formulation, wherein the formulation comprises 0.234 g/mL of calcium oxybate, 0.130 g/mL of potassium oxybate, 0.096 g/mL of magnesium oxybate, and 0.040 g/mL of sodium oxybate (which contains 0.413 g/mL of GHB).

In some embodiments, the formulation is suitable for administration in a single or multiple dosage regimen per day. See U.S. Ser. Nos. 16/688,797, 62/769,380 and 62/769,382.

Any of the above formulations may be prepared and/or packaged as a powdered or dry form for mixing with an aqueous medium before oral administration, or they may be prepared in an aqueous medium and packaged. After mixing with an aqueous medium, preferably to prepare a solution, these formulations are resistant to both microbial growth and chemical conversion of GHB to GBL, thereby increasing the shelf-life of therapeutic formulations of GHB in an aqueous medium. These formulations then provide an easily titratable liquid medium for measuring the dosage of GHB to be administered to a patient.

The GHB may be lyophilized for more ready formulation into a desired vehicle or medium where appropriate. The active compounds may be formulated for parenteral administration, e.g., formulated for injection via intravenous, intraarterial, intramuscular, sub-cutaneous, intralesional, intraperitoneal or other parenteral routes. The preparation of a composition that comprises an aqueous solution that contains a GHB agent as an active component or ingredient will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared; and the preparations can also be emulsified. See U.S. Pat. Nos. 6,472,431; 6,780,889; 7,262,219; 8,263,650; 8,461,203, 8,591,922, 8,901,173, 9,132,107, 9,555,017, 9,795,567, 10,195,168, U.S. Ser. Nos. 16/688,797, 62/769,380 and 62/769,382, and U.S. Patent Publication No. 2018/0263936 for example for more information about parenteral administration.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For oral therapeutic administration, the active compounds may be incorporated with excipients and used in the form of tablets, buccal tablets or tabs, troches, capsules, elixirs, suspensions, syrups, wafers, and the like, to be admixed with an aqueous medium. Such compositions and preparations should contain at least 0.1% of active compound. The percentage of the compositions and preparations may, of course, be varied and may conveniently be between about 2-75% of the weight of the unit, or preferably between 25-60%. The amount of active compounds in such therapeutically useful compositions is such that a suitable dosage will be obtained. See U.S. Pat. Nos. 6,472,431; 6,780,889; 7,262,219; 8,263,650; 8,461,203, 8,591,922, 8,901,173, 9,132,107, 9,555,017, 9,795,567, 10,195,168, U.S. Ser. Nos. 16/688,797, 62/769,380 and 62/769,382, and U.S. Patent Publication No. 2018/0263936 for example.

Methods of the Present Disclosure

In one aspect, the present disclosure provides methods for treating idiopathic hypersomnia (IH) in a patient in need thereof by administering a therapeutically effective amount of a mixed salt oxybate to the patient. In some embodiments, the mixed salt oxybate (such as JZP-258) is used to treat a patient with IH, to treat IH, to treat the symptoms of IH, to treat excessive daytime sleepiness in a patient with IH, to treat sleep inertia in a patient with IH and to achieve adequate sleep duration in a patient with IH. In some embodiments, the patient is an adult patient.

The present disclosure provides methods of treating a patient with IH. Methods of diagnosing a patient with IH are known to those skilled in the art. In some embodiments, a patient is diagnosed with IH using the criteria set forth in International Classification of Sleep Disorders third edition (ICSD-3). In some embodiments, a patient is diagnosed with IH using the criteria set forth in a prior version of the International Classification of Sleep Disorders (e.g., International Classification of Sleep Disorders: Diagnostic and Coding Manual, second edition (ICSD-2)). In some embodiments, a patient is diagnosed with IH using the criteria set forth in the Diagnostic and Statistical Manual of Mental Disorders—fifth edition (DSM-5). In some embodiments, a patient is diagnosed with IH using the criteria set forth in a prior version of the Diagnostic and Statistical Manual of Mental Disorders.

According to the methods of the present disclosure, the mixed salt oxybate that is administered may be any of the mixed salt oxybate compositions described herein. In some embodiments, the relative amount of each salt in the mixed salt oxybate that is administered is expressed in terms of wt/wt %. In some embodiments, the mixed salt oxybate comprises sodium oxybate, potassium oxybate, magnesium oxybate and calcium oxybate, and wherein the mixed salt oxybate comprises about 5%-40% of sodium oxybate (wt/wt %). In some embodiments, the mixed salt oxybate comprises about 5%-40% of sodium oxybate (wt/wt %), about 10%-40% of potassium oxybate (wt/wt %), about 5%-30% of magnesium oxybate (wt/wt %), and about 20%-80% of calcium oxybate (wt/wt %). In some embodiments, the mixed salt oxybate comprises about 8% of sodium oxybate (wt/wt %), about 25.5% of potassium oxybate (wt/wt %), about 19.5% of magnesium oxybate (wt/wt %) and about 47% of calcium oxybate (wt/wt %).

In some embodiments, the relative amount of each salt in the mixed salt oxybate that is administered in a liquid pharmaceutical composition is expressed in terms of wt/vol %. In some embodiments, the liquid pharmaceutical composition comprises a mixed salt oxybate comprising sodium oxybate, potassium oxybate, magnesium oxybate and calcium oxybate, and wherein the mixed salt oxybate comprises about 5%-40% of sodium oxybate (wt/vol %). In some embodiments, the liquid pharmaceutical composition comprises a mixed salt oxybate comprising about 5%-40% of sodium oxybate (wt/vol %), about 10%-40% of potassium oxybate (wt/vol %), about 5%-30% of magnesium oxybate (wt/vol %), and about 20%-80% of calcium oxybate (wt/vol %). In some embodiments, the liquid pharmaceutical composition comprises the mixed salt oxybate comprising about 8% of sodium oxybate (wt/vol %), about 26% of potassium oxybate (wt/vol %), about 19.2% of magnesium oxybate (wt/vol %) and about 46.8% of calcium oxybate (wt/vol %).

In some embodiments, the relative amount of each salt in the mixed salt oxybate that is administered is expressed in terms of % mol. equiv. In some embodiments, the mixed salt oxybate comprises sodium oxybate, potassium oxybate, magnesium oxybate and calcium oxybate, and wherein the mixed salt oxybate comprises about 5%-40% mol. equiv. of sodium oxybate. In some embodiments, the mixed salt oxybate comprises about 5%-40% mol. equiv. of sodium oxybate, about 10%-40% mol. equiv. of potassium oxybate, about 5%-30% mol. equiv. of magnesium oxybate, and about 20%-80% mol. equiv. of calcium oxybate. In some embodiments, the mixed salt oxybate comprises about 8% mol. equiv. of sodium oxybate, about 23% mol. equiv. of potassium oxybate, about 21% mol. equiv. of magnesium oxybate and about 48% mol. equiv. of calcium oxybate.

In some embodiments, a therapeutically effective dose is achieved by starting the patient on an initial daily dose and titrating to an efficacious and tolerated dose by gradually increasing or decreasing the daily administered amount of mixed salt oxybate until a dose that is effective (i.e., the patient with IH is treated) and tolerated is achieved. In some embodiments, the efficacious dose is a dose that improves the patient's excessive daytime sleepiness (EDS) as measured by a decrease in the patient's Epworth Sleepiness Scale (ESS) Score compared to baseline prior to the treatment. In some embodiments, the efficacious dose improves the EDS as measured by a decrease in the patient's ESS of at least 1, 2, 3, 4, 5, or 6 compared to baseline prior to the treatment. In some embodiments, the efficacious dose is a dose that provides an ESS of less than 11 in the treated patient.

In some embodiments, the efficacious dose is a dose that improves at least one symptom of the patient's IH as measured by an improvement in the patient's Idiopathic Hypersomnia Severity Scale (IHSS) Score compared to baseline prior to the treatment. In some embodiments, the efficacious dose is a dose that provides an IHSS score of less than 22 in the treated patient.

In some embodiments, the efficacious dose is a dose that improves at least one symptom of the patient's IH as measured by an improvement in the patient's Patient Global Impression of change (PGIc), Clinical Global Impression of change (CGIc), Functional Outcomes of Sleep Questionnaire, short version (FOSQ-10), Visual analog scale (VAS) for sleep inertia, Total sleep time (TST) from daily sleep diary, or Work Productivity and Activity Impairment Questionnaire: Specific Health Problem (WPAI:SHP) compared to baseline prior to the treatment.

In some embodiments, the present disclosure provides methods for switching a patient with IH who is currently being administered sodium oxybate to a therapeutically effective dose of a mixed salt oxybate. In some embodiments, the switching comprises administering a mixed salt oxybate to a patient with IH and is being treated with sodium oxybate, wherein the dose amount and schedule of the sodium oxybate and the mixed salt oxybate are the same. For example, a patient who is treated once a day with 0.5 g of sodium oxybate is switched to a once a day dose of 0.5 g of a mixed salt oxybate. In some further embodiments, after switching the patient from sodium oxybate to a mixed salt oxybate, the method comprises titrating to an efficacious and tolerated dose by gradually increasing or decreasing the daily administered amount of mixed salt oxybate until a dose that is effective and tolerated is achieved. In some embodiments, after switching a patient from sodium oxybate to a mixed salt oxybate composition, the mixed salt oxybate composition is administered with food. In some embodiments, after switching a patient from sodium oxybate to a mixed salt oxybate composition, the mixed salt oxybate composition is administered without food.

In some embodiments, after switching a patient from sodium oxybate to a mixed salt oxybate composition, the mixed salt oxybate composition is administered with or without regard to food. In some embodiments, the patient is administered the mixed salt oxybate composition at least 2 h after the patient's last meal. In some embodiments, the patient is administered their first dose of the mixed salt oxybate composition (i.e., the dose where the patient transitions from sodium oxybate to the mixed salt oxybate composition) at least 2 h after the patient's last meal. In some embodiments, the patient is administered their first dose of the mixed salt oxybate composition at least 2 h, at least 1.5 h, about 1.0 h, about 0.5 h or about 15 min after the patient's last meal. In some embodiments, the mixed salt oxybate is administered with or without regard to food after the titration period as described herein (i.e., when a stable dose of the mixed salt oxybate composition is achieved).

In some embodiments, the present disclosure provides methods for switching an IH patient who is being administered sodium oxybate and an additional stimulant or alerting agent to a therapeutically effective dose of a mixed salt oxybate. In some embodiments, the additional therapeutic agent is a stimulant. In some embodiments, the stimulant is a CNS stimulant.

In some embodiments, the method of treating IH further comprises administering at least one additional therapeutic agent. In some embodiments, the therapeutic agent(s) is/are selected from the groups consisting of sodium oxybate, an additional stimulant or alerting agent, and sodium oxybate and a stimulant or alerting agent. In some embodiments, the additional therapeutic agent is a stimulant. In some embodiments, the stimulant is a CNS stimulant.

In some embodiments, the present disclosure provides methods for treating idiopathic hypersomnia in a patient in need thereof, the method comprising administering a therapeutically effective amount of a mixed salt oxybate to a patient who is not being administered sodium oxybate for the treatment of idiopathic hypersomnia (i.e. sodium oxybate naïve). In some embodiments, the patient is not being treated with sodium oxybate when treatment with the mixed salt oxybate is initiated. In some embodiments, the patient has not been administered sodium oxybate for at least about 2 weeks prior to treatment with the mixed salt oxybate. In some embodiments, the patient has not been administered sodium oxybate for at least about 14 to 30 days prior to treatment with the mixed salt oxybate. In some embodiments, the patient has never been previously administered with sodium oxybate prior to treatment with the mixed salt oxybate.

In some embodiments, the sodium oxybate naïve patient is administered an initial dose of the mixed oxybate (e.g., once or twice daily). In some further embodiments, after administering an initial daily dose of the mixed salt oxybate to the patient, the method comprises titrating to an efficacious and tolerated dose by gradually increasing the daily administered amount of mixed salt oxybate until a dose that is effective and tolerated is achieved.

In some embodiments, the methods of the present disclosure comprise:
(a) administering an initial daily dose of the mixed salt oxybate to the patient and
(b) titrating the dose to provide a therapeutically effective amount of the mixed salt oxybate.

In some embodiments, the methods of the present disclosure comprise:
(a) administering an initial daily dose of the mixed salt oxybate to a sodium oxybate naïve patient, and
(b) titrating the dose to provide a therapeutically effective amount of the mixed salt oxybate.

In some embodiments, the initial daily dose is from about 0.5 g to about 4.5 g of the mixed salt oxybate. In some embodiments, the initial daily dose is less than about 4.5 g of the mixed salt oxybate. In some embodiments, the initial daily dose is less than about 3.0 g of the mixed salt oxybate. In some embodiments, the initial daily dose is about 0.25 g of the mixed salt oxybate. In some embodiments, the initial daily dose is about 0.50 g of the mixed salt oxybate. In some embodiments, the initial daily dose is about 1.0 g of the mixed salt oxybate. In some embodiments, the initial daily dose is about 1.5 g of the mixed salt oxybate. In some embodiments, the initial daily dose is about 2.0 g of the mixed salt oxybate. In some embodiments, the initial daily dose is about 3.0 g of the mixed salt oxybate. In some embodiments, the initial daily dose is about 4.5 g of the mixed salt oxybate.

In some embodiments, the titration comprises switching a patient from a once a day dose to a twice a day dose of the mixed salt oxybate. In some embodiments, the titration comprises switching a patient from a twice a day dose to a three times a day dose of the mixed salt oxybate. In some embodiments, the titration comprises switching a patient from a twice a day dose to a once a day dose of the mixed salt oxybate. In some embodiments, the titration comprises switching a patient from a three times a day dose to a twice a day dose of the mixed salt oxybate.

In some embodiments, the titration comprises administering ascending doses of the mixed salt oxybate. In some embodiments, the daily dose is increased every week until a dose that is effective and tolerated is achieved. In some embodiments, the daily dose is increased every other week until a dose that is effective and tolerated is achieved. In some embodiments, the daily dose is increased every third week until a dose that is effective and tolerated is achieved.

In some embodiments, the daily dose is increased on a weekly basis until a dose that is effective and tolerated is achieved. In some embodiments, the daily dose is increased once every week until a dose that is effective and tolerated is achieved. In some embodiments, the daily dose is increased twice every week until a dose that is effective and tolerated is achieved. In some embodiments, the daily dose is increased three times every week until a dose that is effective and tolerated is achieved. In some embodiments, the daily dose is increased four times every week until a dose that is effective and tolerated is achieved. In some embodiments, the daily dose is increased five times every week until a dose that is effective and tolerated is achieved. In some embodiments, the daily dose is increased six times every week until a dose that is effective and tolerated is achieved. In some embodiments, the total weekly dose is increased by less than about 1.5 g of the mixed salt oxybate.

In some embodiments, the daily dose is increased every day until a dose that is effective and tolerated is achieved. In some embodiments, the daily dose is increased every other day until a dose that is effective and tolerated is achieved. In some embodiments, the daily dose is increased every second or third day until a dose that is effective and tolerated is achieved. In some embodiments, the daily dose is increased every third day until a dose that is effective and tolerated is achieved. In some embodiments, the daily dose is increased every second, third, or fourth day until a dose that is effective and tolerated is achieved. In some embodiments, the daily dose is increased every fourth day until a dose that is effective and tolerated is achieved. In some embodiments, the daily dose is increased every second, third, fourth, or fifth day until a dose that is effective and tolerated is achieved. In some embodiments, the daily dose is increased every fifth day until a dose that is effective and tolerated is achieved. In some embodiments, the daily dose is increased every second, third, fourth, fifth, or sixth day until a dose that is effective and tolerated is achieved. In some embodiments, the daily dose is increased every sixth day until a dose that is effective and tolerated is achieved. In some embodiments, the daily dose is increased every second, third, fourth, fifth, sixth, or seventh day until a dose that is effective and tolerated is achieved. In some embodiments, the daily dose is increased every seventh day until a dose that is effective and tolerated is achieved.

In some embodiments, the titration comprises increasing the daily dose by less than about 1.5 g of the mixed salt oxybate. In some embodiments, the titration comprises increasing the daily dose by about 0.25 g, about 0.5 g, about 0.75 g, about 1.0 g, about 1.25 g, about 1.5 g, about 1.75 g, or about 2.0 g of the mixed salt oxybate. In some embodiments, the titration comprises increasing the daily dose by about 1.0 g-1.5 g of the mixed salt oxybate.

In some embodiments, the daily dose is increased by about 0.5 g to 1.5 g per week. In some embodiments, the daily dose is increased by about 0.25 g to 1.5 g per week. In some embodiments, the daily dose is increased by less than about 1.5 g per week.

In some embodiments, the mixed salt oxybate is administered to a subpopulation of patients that have difficulty awakening, for example, as a result of significant sleep inertia or long sleep time (e.g., sleep time of greater that about 9 hours, greater than about 11 hours, or from about 11 hours to about 24 hours, including all values and ranges therebetween). In some embodiments, the mixed salt oxybate is administered as a once nightly dosing regimen to a patient that has difficulty awakening.

In some embodiments, the initial daily dose of the mixed salt oxybate administered to a sodium oxybate naïve patient is about 3 grams, and is increased about 1.5 grams/night per week until a dose that is effective and tolerated is achieved. In some embodiments, the initial daily dose of the mixed salt oxybate administered to a sodium oxybate naïve patient is less than or equal to about 3 grams, and is increased no more than about 1.5 grams/night per week until a dose that is effective and tolerated is achieved. In some embodiments, the initial daily dose of the mixed salt oxybate administered to a sodium oxybate naïve patient is less than or equal to about 3 grams, and is increased less than or equal to about 1.5 grams/night per week until a dose that is effective and tolerated is achieved. In some embodiments, the initial daily dose of the mixed salt oxybate administered to a sodium oxybate naïve patient is about 3 grams, and is increased about 1.5 grams at weekly intervals until a dose that is effective and tolerated is achieved. In some embodiments, after a dose of the mixed salt oxybate that is effective and tolerated is achieved in a sodium oxybate naïve patient the administered dose is further adjusted to optimize the patient's treatment. The dose may be optimized by the methods described herein (for example, up-titrating or down-titrating the dose, change the number of daily administrations, the patient's dose up or changing the division of the total nightly dosing). In some embodiments, the dose is optimized by changing from once nightly administration to twice nightly administration, wherein the total nightly dose of the mixed salt oxybate does not initially exceed the previous total nightly dose by more than about 1.5 g/night per week. In some embodiments, the dose is optimized by changing from a twice nightly administration to a once nightly administration, wherein the single nightly dose of the mixed salt oxybate does not initially exceed the previous first nightly dose by more than about 1.5 g/night per week. In some embodiments, the maximum daily dose of the mixed salt oxybate administered to a sodium oxybate naïve patient is no more than about 6 grams. In some embodiments, the maximum daily dose of the mixed salt oxybate administered to a sodium oxybate naïve patient is no more than about 6 grams is administered once nightly.

In some embodiments, the initial daily dose of the mixed salt oxybate (such as JZP-258) administered to an adult patient with idiopathic hypersomnia is less than or equal to about 3 grams administered once nightly, and is increased by less than or equal to about 1.5 grams/night per week until a dose that is effective and tolerated is achieved, and wherein the maximum dose is no more than about 6 grams administered once nightly. In some embodiments, the initial daily dose of the mixed salt oxybate administered to an adult patient with idiopathic hypersomnia is about 3 grams, and is increased about 1.5 grams/night per week until a dose that is effective and tolerated is achieved. In some embodiments, the initial daily dose of the mixed salt oxybate administered to an adult patient with idiopathic hypersomnia is less than or equal to about 3 grams, and is increased by no more than about 1.5 grams/night per week until a dose that is effective and tolerated is achieved. In some embodiments, the initial daily dose of the mixed salt oxybate to an adult patient with idiopathic hypersomnia is less than or equal to about 3 grams, and is increased less than or equal to about 1.5 grams/night per week until a dose that is effective and tolerated is achieved. In some embodiments, the initial daily dose of the mixed salt oxybate administered to an adult patient with idiopathic hypersomnia is about 3 grams, and is increased about 1.5 grams at weekly intervals until a dose that is effective and tolerated is achieved. In some embodiments, after a dose of the mixed salt oxybate that is effective and tolerated is achieved in an adult patient with idiopathic hypersomnia the administered dose is further adjusted to optimize the patient's treatment. The dose may be optimized by the methods described herein (for example, up-titrating or down-titrating the dose, change the number of daily administrations, the patient's dose up or changing the division of the total nightly dosing). In some embodiments, the dose is optimized by changing from a once nightly administration to a twice nightly administration, wherein the total nightly dose of the mixed salt oxybate does not initially exceed the previous total nightly dose by more than about 1.5 g/night per week. In some embodiments, the dose is optimized by changing from a twice nightly administration to a once nightly administration, wherein the single nightly dose of the mixed salt oxybate does not initially exceed the previous first nightly dose by more than about 1.5 g/night per week. In some embodiments, the maximum daily dose of the mixed salt oxybate administered to an adult patient with idiopathic hypersomnia is no more than about 6 grams. In some embodiments, the maximum daily dose of the mixed salt oxybate administered to an adult patient with idiopathic hypersomnia is no more than about 6 grams is administered once nightly.

In some embodiments, the initial daily dose of the mixed salt oxybate administered to a sodium oxybate naïve patient is about 4.5 grams, and is increased about 1.5 grams per night per week until a dose that is effective and tolerated is achieved. In some embodiments, the initial daily dose of the mixed salt oxybate administered to a sodium oxybate naïve patient is less than or equal to about 4.5 grams, and is increased less than or equal to about 1.5 grams/night per week until a dose that is effective and tolerated is achieved. In some embodiments, the initial daily dose of the mixed salt oxybate administered to a sodium oxybate naïve patient is about 4.5 grams, and is increased no more than about 1.5 grams/night per week until a dose that is effective and tolerated is achieved. In some embodiments, the initial daily dose of the mixed salt oxybate administered to a sodium oxybate naïve patient is about 4.5 grams, and is increased about 1.5 grams at weekly intervals until a dose that is effective and tolerated is achieved. In some embodiments, the initial daily dose of the mixed salt oxybate administered to a sodium oxybate naïve patient is less than or equal to about 4.5 grams divided equally or unequally into 2 doses administered nightly. In some embodiments, after a dose of the mixed salt oxybate that is effective and tolerated is achieved in a sodium oxybate naïve patient the administered dose is further adjusted to optimize the patient's treatment. The dose may be optimized by the methods described herein (for example, up-titrating or down-titrating the dose, change the number of daily administrations, the patient's dose up or changing the division of the total nightly dosing). In some embodiments, the dose is optimized by changing from a once nightly administration to a twice nightly administration, wherein the total nightly dose of the mixed salt oxybate does not initially exceed the previous total nightly dose by more than 1.5 g/night per week. In some embodiments, the dose is optimized by changing from a twice nightly administration to a once nightly administration, wherein the single nightly dose of the mixed salt oxybate does not initially exceed the previous first nightly dose by more than 1.5 g/night per week. In some embodiments, the maximum daily dose of the mixed salt oxybate administered to a sodium oxybate naïve patient is no more than about 9 grams. In some embodiments, the maximum daily dose of the mixed salt oxybate administered to a sodium oxybate naïve patient is no more than 9 grams divided equally or unequally into 2 doses administered nightly.

In some embodiments, the initial daily dose of the mixed salt oxybate (such as JZP-258) administered to an adult patient with idiopathic hypersomnia is less than or equal to about 4.5 grams divided equally or unequally into 2 doses administered nightly, and is increased less than or equal to about 1.5 grams/night per week divided equally or unequally into 2 doses until a dose that is effective and tolerated is achieved, wherein the maximum dose is no more than about 9 grams divided equally or unequally into 2 doses administered nightly. In some embodiments, the nightly dose is divided equally. In some embodiments, the nightly dose is divided unequally. In some embodiments, the nightly dose is divided unequally. In some embodiments, the first dose is administered at bedtime or after initial period of sleep and the second dose is administered about 2.5 hours to about 4 hours later. In some embodiments, the first dose is administered at bedtime and the second dose is administered about 2.5 hours to about 4 hours later. In some embodiments, the initial daily of the mixed salt oxybate dose administered to an adult patient with idiopathic hypersomnia is about 4.5 grams, and is increased about 1.5 grams per night per week until a dose that is effective and tolerated is achieved. In some embodiments, the initial daily dose of the mixed salt oxybate administered to an adult patient with idiopathic hypersomnia is less than or equal to about 4.5 grams, and is increased less than or equal to about 1.5 grams/night per week until a dose that is effective and tolerated is achieved. In some embodiments, the initial daily dose of the mixed salt oxybate administered to an adult patient with idiopathic hypersomnia is about 4.5 grams, and is increased by no more than about 1.5 grams/night per week until a dose that is effective and tolerated is achieved. In some embodiments, the initial daily dose of the mixed salt oxybate administered to an adult patient with idiopathic hypersomnia is about 4.5 grams, and is increased about 1.5 grams at weekly intervals until a dose that is effective and tolerated is achieved. In some embodiments, the initial daily dose of the mixed salt oxybate administered to an adult patient with idiopathic hypersomnia is less than or equal to about 4.5 grams divided equally or unequally into 2 doses administered nightly. In some embodiments, after a dose of the mixed salt oxybate that is effective and tolerated is achieved in an adult patient with idiopathic hypersomnia the administered dose is further adjusted to optimize the patient's treatment. The dose may be optimized by the methods described herein (for example, up-titrating or down-titrating the dose, change the number of daily administrations, the patient's dose up or changing the division of the total nightly dosing). In some embodiments, the dose is optimized by changing from a once nightly administration to a twice nightly administration, wherein the total nightly dose of the mixed salt oxybate does not initially exceed the previous total nightly dose by more than 1.5 g/night per week. In some embodiments, the dose is optimized by changing from a twice nightly administration to a once nightly administration, wherein the single nightly dose of the mixed salt oxybate does not initially exceed the previous first nightly dose by more than 1.5 g/night per week. In some embodiments, the maximum daily dose of the mixed salt oxybate administered to an adult patient with idiopathic hypersomnia is no more than about 9 grams. In some embodiments, the maximum daily dose of the mixed salt oxybate administered to an adult patient with idiopathic hypersomnia is no more than 9 grams divided equally or unequally into 2 doses administered nightly.

In some embodiments, the initial daily dose is 4.5 grams, and is increased 1.5 grams per night once per week until a dose that is effective and tolerated is achieved. In some embodiments, the initial daily dose is 4.5 grams, and is increased 1.5 grams at weekly intervals until a dose that is effective and tolerated is achieved. In some embodiments, after a dose that is effective and tolerated is achieved the administered dose is further adjusted to optimize the patient's treatment. The dose may be optimized by the methods described herein (for example, up-titrating or down-titrating the dose, change the number of daily administrations, the patient's dose up or changing the division of the total nightly dosing).

In some embodiments, the titration comprises administering descending doses of the mixed salt oxybate. In some embodiments, the daily dose is decreased every week until a dose that is effective and tolerated is achieved. In some embodiments, the daily dose is decreased every other week until a dose that is effective and tolerated is achieved. In some embodiments, the daily dose is decreased every third week until a dose that is effective and tolerated is achieved.

In some embodiments, the daily dose is decreased on a weekly basis until a dose that is effective and tolerated is achieved. In some embodiments, the daily dose is decreased once every week until a dose that is effective and tolerated is achieved. In some embodiments, the daily dose is decreased twice every week until a dose that is effective and tolerated is achieved. In some embodiments, the daily dose is decreased three times every week until a dose that is effective and tolerated is achieved. In some embodiments, the daily dose is decreased four times every week until a dose that is effective and tolerated is achieved. In some embodiments, the daily dose is decreased five times every week until a dose that is effective and tolerated is achieved. In some embodiments, the daily dose is decreased six times every week until a dose that is effective and tolerated is achieved.

In some embodiments, the daily dose is decreased every day until a dose that is effective and tolerated is achieved. In some embodiments, the daily dose is decreased every other day until a dose that is effective and tolerated is achieved. In some embodiments, the daily dose is decreased every second or third day until a dose that is effective and tolerated is achieved. In some embodiments, the daily dose is decreased every third day until a dose that is effective and tolerated is achieved. In some embodiments, the daily dose is decreased every second, third, or fourth day until a dose that is effective and tolerated is achieved. In some embodiments, the daily dose is decreased every fourth day until a dose that is effective and tolerated is achieved. In some embodiments, the daily dose is decreased every second, third, fourth, or fifth day until a dose that is effective and tolerated is achieved. In some embodiments, the daily dose is decreased every fifth day until a dose that is effective and tolerated is achieved. In some embodiments, the daily dose is decreased every second, third, fourth, fifth, or sixth day until a dose that is effective and tolerated is achieved. In some embodiments, the daily dose is decreased every sixth day until a dose that is effective and tolerated is achieved. In some embodiments, the daily dose is decreased every second, third, fourth, fifth, sixth, or seventh day until a dose that is effective and tolerated is achieved. In some embodiments, the daily dose is decreased every seventh day until a dose that is effective and tolerated is achieved.

In some embodiments, the titration comprises decreasing the daily dose by less than about 1.5 g of the mixed salt oxybate. In some embodiments, the titration comprises decreasing the daily dose by about 0.25 g, about 0.5 g, about 0.75 g, about 1.0 g, about 1.25 g, about 1.5 g, about 1.75 g, or about 2.0 g of the mixed salt oxybate. In some embodiments, the titration comprises decreasing the daily dose by about 1.0 g-1.5 g of the mixed salt oxybate.

In some embodiments, the daily dose is decreased by about 0.5 g to 1.5 g per week. In some embodiments, the daily dose is decreased by about 0.25 g to 1.5 g per week. In some embodiments, the daily dose is decreased by less than about 1.5 g per week. In some embodiments, the daily dose is decreased by about 0.5 g to 9.0 g per week. In some embodiments, the daily dose is decreased by about 0.25 g to 9.0 g per week.

In some embodiments, the initial daily dose is 4.5 grams, and is decreased 1.5 grams per night once per week until a dose that is effective and tolerated is achieved. In some embodiments, the initial daily dose is 4.5 grams, and is decreased 1.5 grams at weekly intervals until a dose that is effective and tolerated is achieved. In some embodiments, after a dose that is effective and tolerated is achieved the administered dose is further adjusted to optimize the patient's treatment. The dose may be optimized by the methods described herein (for example, up-titrating or down-titrating the dose, change the number of daily administrations, the patient's dose up or changing the division of the total nightly dosing).

In some embodiments of the present disclosure, the methods of the present disclosure provide therapeutically effective blood plasma levels of oxybate for treating idiopathic hypersomnia (i.e., effective blood plasma levels of oxybate are achieved following administration of a mixed salt oxybate, such as JZP-258). Blood plasma levels of oxybate may be expressed using pharmacokinetic parameters that are known to those skilled in the art, such as steady state plasma levels, AUC, $C_{max}$ and $C_{min}$.

In some embodiments, the administration of the mixed salt oxybate provides therapeutically effective blood plasma levels of oxybate as expressed in terms of the effective Cmax. In some embodiments, the administration of the mixed salt oxybate (e.g., JZP-258) provides a Cmax of about 10 µg/mL to about 300 µg/mL, including from about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 110 µg/mL, about 120 µg/mL, about 130 µg/mL, about 140 µg/mL, about 150 µg/mL, about 160 µg/mL, about 170 µg/mL, about 180 µg/mL, about 190 µg/mL, about 200 µg/mL, about 210 µg/mL, about 220 µg/mL, about 230 µg/mL, about 240 µg/mL, about 250 µg/mL, about 260 µg/mL, about 270 µg/mL, about 280 µg/mL, about 290 µg/mL, to about 300 µg/mL, including all values and ranges therebetween. In some embodiments, the mixed salt oxybate (e.g., JZP-258) is administered once per day. In some embodiments, the mixed salt oxybate (e.g., JZP-258) is administered twice per day. In some embodiments, the mixed salt oxybate (e.g., JZP-258) is administered three times per day.

In some embodiments, the mixed salt oxybate (e.g., JZP-258) is administered once per day to a patient in need thereof (e.g., once nightly), and the administration provides a Cmax of about 20 µg/mL to about 130 µg/mL, including about 20 µg/mL, about 25 µg/mL, about 30 µg/mL, about 35 µg/mL, about 40 µg/mL, about 45 µg/mL, about 50 µg/mL, about 55 µg/mL, about 60 µg/mL, about 65 µg/mL, about 70 µg/mL, about 75 µg/mL, about 80 µg/mL, about 85 µg/mL, about 90 µg/mL, about 95 µg/mL, about 100 µg/mL, about 105 µg/mL, about 110 µg/mL, about 115 µg/mL, about 120 µg/mL, about 125 µg/mL, to about 130 µg/mL, including all ranges and values therebetween. In some embodiments, the once daily administration provides in the patient a Cmax of about 40 µg/mL to about 110 µg/mL. In some embodiments, the once daily administration of the mixed salt oxybate (e.g., JZP-258) provides in the patient a median Cmax of about 85 µg/mL.

In some embodiments, the mixed salt oxybate (e.g., JZP-258) is administered two times per day to a patient in need thereof (e.g., twice nightly) and the administration provides a Cmax of about 30 µg/mL to about 220 µg/mL, including about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 110 µg/mL, about 120 µg/mL, about 130 µg/mL, about 140 µg/mL, about 150 µg/mL, about 160 µg/mL, about 170 µg/mL, about 180 µg/mL, about 190 µg/mL, about 200 µg/mL, about 210 µg/mL, to about 220 µg/mL, including all values and ranges therebetween. In some embodiments, the twice daily administration of the mixed salt oxybate provides a Cmax of about 40 µg/mL to about 210 µg/mL, or about 50 µg/mL to about 200 µg/mL. In some embodiments, the twice daily administration of the mixed salt oxybate (e.g., JZP-258) provides a median Cmax of about 126 µg/mL.

In some embodiments, the administration of the mixed salt oxybate (e.g., JZP-258) to a patient in need thereof provides an AUC0-t last of about 50 µg/mL·h to about 1500 µg/mL·h, including about 50 µg/mL·h, about 60 µg/mL·h, about 80 µg/mL·h, about 100 µg/mL·h, about 120 µg/mL·h, about 140 µg/mL·h, about 160 µg/mL·h, about 180 µg/mL·h, about 200 µg/mL·h, about 220 µg/mL·h, about 240 µg/mL·h, about 260 µg/mL·h, about 280 µg/mL·h, about 300 µg/mL·h, about 320 µg/mL·h, about 340 µg/mL·h, about 360 µg/mL·h, about 380 µg/mL·h, about 400 µg/mL·h, about 420 µg/mL·h, about 440 µg/mL·h, about 460 µg/mL·h, about 480 µg/mL·h, about 500 µg/mL·h, about 520 µg/mL·h, about 540 µg/mL·h, about 560 µg/mL·h, about 580 µg/mL·h, about 600 µg/mL·h, about 620 µg/mL·h, about 640 µg/mL·h, about 660 µg/mL·h, about 680 µg/mL·h, about 700 µg/mL·h, about 720 µg/mL·h, about 740 µg/mL·h, about 760 µg/mL·h, about 780 µg/mL·h, about 800 µg/mL·h, about 820 µg/mL·h, about 840 µg/mL·h, about 860 µg/mL·h, about 880 µg/mL·h, about 900 µg/mL·h, about 920 µg/mL·h, about 940 µg/mL·h, about 960 µg/mL·h, about 980 µg/mL·h, about 1000 µg/mL·h, about 1020 µg/mL·h, about 1040 µg/mL·h, about 1060 µg/mL·h, about 1080 µg/mL·h, about 1100 µg/mL·h, about 1120 µg/mL·h, about 1140 µg/mL·h, about 1160 µg/mL·h, about 1180 µg/mL·h, about 1200 µg/mL·h, about 1250 µg/mL·h, about 1300 µg/mL·h, about 1350 µg/mL·h, about 1400 µg/mL·h, about 1450 µg/mL·h, to about 1500 µg/mL·h, including all values and ranges therebetween.

In some embodiments, the mixed salt oxybate (e.g., JZP-258) is administered once per day to a patient in need thereof (e.g., once nightly) and the administration provides an AUC0-t last of about 50 µg/mL·h to about 600 µg/mL·h, including about 50 µg/mL·h, about 60 µg/mL·h, about 70 µg/mL·h, about 80 µg/mL·h, about 90 µg/mL·h, about 100 µg/mL·h, about 110 µg/mL·h, about 120 µg/mL·h, about 130 µg/mL·h, about 140 µg/mL·h, about 150 µg/mL·h, about 160 µg/mL·h, about 170 µg/mL·h, about 180 µg/mL·h, about 190 µg/mL·h, about 200 µg/mL·h, about 210 µg/mL·h, about 220 µg/mL·h, about 230 µg/mL·h, about 240 µg/mL·h, about 250 µg/mL·h, about 260 µg/mL·h, about 270 µg/mL·h, about 280 µg/mL·h, about 290 µg/mL·h, about 300 µg/mL·h, about 310 µg/mL·h, about 320 µg/mL·h, about 330 µg/mL·h, about 340 µg/mL·h, about 350 µg/mL·h, about 360 µg/mL·h, about 370 µg/mL·h, about 380 µg/mL·h, about 390 µg/mL·h, about 400 µg/mL·h, about 410 µg/mL·h, about 420 µg/mL·h, about 430 µg/mL·h, about 440 µg/mL·h, about 450 µg/mL·h, about 460 µg/mL·h, about 470 µg/mL·h, about 480 µg/mL·h, about 490 µg/mL·h, about 500 µg/mL·h, about 510 µg/mL·h, about 520 µg/mL·h, about 530 µg/mL·h, about 540 µg/mL·h, about 550 µg/mL·h, about 560 µg/mL·h, about 570 µg/mL·h, about 580 µg/mL·h, about 590 µg/mL·h to about 600 µg/mL·h, including all values and subranges therebetween. In some embodiments, the administration of the mixed salt oxybate (e.g., JZP-258) to a patient in need thereof provides an AUC0-t last of about 50 µg/mL·h to about 500 µg/mL·h, or about 60 µg/mL·h to about 450 µg/mL·h. In some embodiments, the administration provides a median AUC0-t last of about 229.5 µg/mL·h.

In some embodiments, the mixed salt oxybate (e.g., JZP-258) is administered twice per day to a patient in need thereof (e.g., twice nightly) and the administration provides an AUC0-t last of about 100 µg/mL·h to about 1200 µg/mL·h, including about 100 µg/mL·h, about 120 µg/mL·h, about 140 µg/mL·h, about 160 µg/mL·h, about 180 µg/mL·h, 200 µg/mL·h, about 220 µg/mL·h, about 240 µg/mL·h, about 260 µg/mL·h, about 280 µg/mL·h, about 300 µg/mL·h, about 320 µg/mL·h, about 340 µg/mL·h, about 360 µg/mL·h, about 380 µg/mL·h, about 400 µg/mL·h, about 420 µg/mL·h, about 440 µg/mL·h, about 460 µg/mL·h, about 480 µg/mL·h, about 500 µg/mL·h, about 520 µg/mL·h, about 540 µg/mL·h, about 560 µg/mL·h, about 580 µg/mL·h, about 600 µg/mL·h, about 620 µg/mL·h, about 640 µg/mL·h, about 660 µg/mL·h, about 680 µg/mL·h, about 700 µg/mL·h, about 720 µg/mL·h, about 740 µg/mL·h, about 760 µg/mL·h, about 780 µg/mL·h, about 800 µg/mL·h, about 820 µg/mL·h, about 840 µg/mL·h, about 860 µg/mL·h, about 880 µg/mL·h, about 900 µg/mL·h, about 920 µg/mL·h, about 940 µg/mL·h, about 960 µg/mL·h, about 980 µg/mL·h, about 1000 µg/mL·h, about 1020 µg/mL·h, about 1040 µg/mL·h, about 1060 µg/mL·h, about 1080 µg/mL·h, about 1100 µg/mL·h, about 1120 µg/mL·h, about 1140 µg/mL·h, about 1160 µg/mL·h, about 1180 µg/mL·h, to about 1200 µg/mL·h, or about 150 µg/mL·h to about 1100 µg/mL·h. In some embodiments, the administration provides a median AUC0-t last of about 479.3 µg/mL·h.

In some embodiments, the titration is conducted from about 1 week to about 14 weeks.

In some embodiments, the mixed salt oxybate is administered three times per day. In some embodiments, the mixed salt oxybate is administered three times per day in equal doses. In some embodiments, the mixed salt oxybate is administered three times per day in unequal doses. In some embodiments, the mixed salt oxybate is administered twice per day. In some embodiments, the mixed salt oxybate is administered twice per day in equal doses. In some embodiments, the mixed salt oxybate is administered twice per day in unequal doses. In some embodiments, the mixed salt oxybate is administered once per day, See U.S. Ser. Nos. 16/688,797, 62/769,380 and 62/769,382. In some embodiments, the mixed salt oxybate is administered at bedtime. In some embodiments, the mixed salt oxybate is administered after an initial period of sleep. In some embodiments, the mixed salt oxybate is administered at bedtime and about 2.5 h-4 h after the bedtime administration. In some embodiments, the mixed salt oxybate is administered after an initial period of sleep and about 2.5 h-4 h after the bedtime administration. In some embodiments, the mixed salt oxybate is administered at bedtime or after an initial period of sleep and about 2.5 h-4 h after the bedtime administration. In some embodiments, the mixed salt oxybate is administered after a period of sleep. In some embodiments, the mixed salt oxybate is administered after a period of sleep and about 2.5 h-4 h later.

In some embodiments, the dose of the mixed salt oxybate is described in terms of the amount of the mixed salt oxybate that is administered to the patient. In some embodiments, about 0.25 g-10.0 g, about 1.0 g-9.0 g, about 2.0 g-10.0 g; about 3.0 g-9.5 g; or about 4.5 g-9.0 g of the mixed salt oxybate is administered per day.

In some embodiments, about 0.5 g-9 g of the mixed salt oxybate (such as JZP-258) is administered per day (e.g., as a single dose, or divided into 2 or 3 equal or unequal doses), including about 0.5 g, about 1.0 g, about 1.5 g, about 2.0 g, about 2.5 g, about 3.0 g, about 3.5 g, about 4.0 g, about 4.5 g, about 5.0 g, about 5.5 g, about 6.0 g, about 6.5 g, about 7.0 g, about 7.5 g, about 8.0 g, about 8.5 g, to about 9.0 g, including all values and ranges therebetween (e.g., about 6 g is administered once per day, or about 5 g to about 6 g is administered once per day). In some embodiments, about 2.0 g-9.0 g of the mixed salt oxybate (such as JZP-258) is administered once per day. In some embodiments, about 2.0 g-6.0 g of the mixed salt oxybate (such as JZP-258) is administered once per day. In some embodiments, about 4.5 g-6.0 g of the mixed salt oxybate (such as JZP-258) is administered once per day. In some embodiments, about 4.0 g-9.0 g of the mixed salt oxybate (such as JZP-258) is administered per day, wherein the mixed salt oxybate is administered in two equal or unequal doses. In some embodiments, about 0.5 g of the mixed salt oxybate (such as JZP-258) is administered per day. In some embodiments, about 0.5 g of the mixed salt oxybate (such as JZP-258) is administered once per day. In some embodiments, about 0.25 g of the mixed salt oxybate (such as JZP-258) is administered twice per day. In some embodiments, about 0.17 g of the mixed salt oxybate (such as JZP-258) is administered three times per day. In some embodiments, about 1.0 g of the mixed salt oxybate (such as JZP-258) is administered per day. In some embodiments, about 1.0 g of the mixed salt oxybate (such as JZP-258) is administered once per day. In some embodiments, about 0.5 g of the mixed salt oxybate (such as JZP-258) is administered twice per day. In some embodiments, about 0.33 g of the mixed salt oxybate (such as JZP-258) is administered three times per day. In some embodiments, about 1.5 g of the mixed salt oxybate (such as JZP-258) is administered per day. In some embodiments, about 1.5 g of the mixed salt oxybate (such as JZP-258) is administered once per day. In some embodiments, about 0.75 g of the mixed salt oxybate (such as JZP-258) is administered twice per day. In some embodiments, about 0.50 g of the mixed salt oxybate (such as JZP-258) is administered three times per day. In some embodiments, about 2.0 g of the mixed salt oxybate (such as JZP-258) is administered per day. In some embodiments, about 2.0 g of the mixed salt oxybate (such as JZP-258) is administered once per day. In some embodiments, about 1.0 g of the mixed salt oxybate (such as JZP-258) is administered twice per day. In some embodiments, about 0.66 g of the mixed salt oxybate (such as JZP-258) is administered three times per day. In some embodiments, about 2.5 g of the mixed salt oxybate (such as JZP-258) is administered per day. In some embodiments, about 2.5 g of the mixed salt oxybate (such as JZP-258) is administered once per day. In some embodiments, about 1.25 g of the mixed salt oxybate (such as JZP-258) is administered twice per day. In some embodiments, about 0.83 g of the mixed salt oxybate (such as JZP-258) is administered three times per day. In some embodiments, about 3.0 g of the mixed salt oxybate (such as JZP-258) is administered per day. In some embodiments, about 3.0 g of the mixed salt oxybate (such as JZP-258) is administered once per day. In some embodiments, about 1.5 g of the mixed salt oxybate (such as JZP-258) is administered twice per day. In some embodiments, about 1.0 g of the mixed salt oxybate (such as JZP-258) is administered three times per day. In some embodiments, about 3.5 g of the mixed salt oxybate (such as JZP-258) is administered per day. In some embodiments, about 3.5 g of the mixed salt oxybate (such as JZP-258) is administered once per day. In some embodiments, about 1.75 g of the mixed salt oxybate (such as JZP-258) is administered twice per day. In some embodiments, about 1.16 g of the mixed salt oxybate (such as JZP-258) is administered three times per day. In some embodiments, about 4.0 g of the mixed salt oxybate (such as JZP-258) is administered per day. In some embodiments, about 4.0 g of the mixed salt oxybate (such as JZP-258) is administered once per day. In some embodiments, about 2.0 g of the mixed salt oxybate (such as JZP-258) is administered twice per day. In some embodiments, about 1.32 g of the mixed salt oxybate (such as JZP-258) is administered three times per day. In some embodiments, about 4.5 g of the mixed salt oxybate (such as JZP-258) is administered per day. In some embodiments, about 4.5 g of the mixed salt oxybate (such as JZP-258) is administered once per day. In some embodiments, about 2.25 g of the mixed salt oxybate (such as JZP-258) is administered twice per day. In some embodiments, about 1.5 g of the mixed salt oxybate (such as JZP-258) is administered three times per day. In some embodiments, about 5.0 g of the mixed salt oxybate (such as JZP-258) is administered per day. In some embodiments, about 5.0 g of the mixed salt oxybate (such as JZP-258) is administered once per day. In some embodiments, about 2.5 g of the mixed salt oxybate (such as JZP-258) is administered twice per day. In some embodiments, about 1.7 g of the mixed salt oxybate (such as JZP-258) is administered is three times per day. In some embodiments, about 5.5 g of the mixed salt oxybate (such as JZP-258) is administered per day. In some embodiments, about 5.5 g of the mixed salt oxybate (such as JZP-258) is administered once per day. In some embodiments, about 2.75 g of the mixed salt oxybate (such as JZP-258) is administered twice per day. In some embodiments, about 1.8 g of the mixed salt oxybate (such as JZP-258) is administered three times per day. In some embodiments, about 6 g of the mixed salt oxybate (such as JZP-258) is administered per day. In some embodiments, about 6 g of the mixed salt oxybate (such as JZP-258) is administered once per day. In some embodiments, about 3.0 g of the mixed salt oxybate (such as JZP-258) is administered twice per day. In some embodiments, about 2.0 g of the mixed salt oxybate (such as JZP-258) is administered three times per day. In some embodiments, about 7.5 g of the mixed salt oxybate (such as JZP-258) is administered per day. In some embodiments, about 7.5 g of the mixed salt oxybate (such as JZP-258) is administered once per day. In some embodiments, about 3.75 g of the mixed salt oxybate (such as JZP-258) is administered twice per day. In some embodiments, about 2.5 g of the mixed salt oxybate (such as JZP-258) is administered three times per day. In some embodiments, about 9.0 g of the mixed salt oxybate (such as JZP-258) is administered per day. In some embodiments, about 9.0 g of the mixed salt oxybate (such as JZP-258) is administered once per day. In some embodiments, about 4.5 g of the mixed salt oxybate (such as JZP-258) is administered twice per day. In some embodiments, about 3.0 g of the mixed salt oxybate (such as JZP-258) is administered three times per day.

In some embodiments, the dose of the mixed salt oxybate is described in terms of the amount of GHB that is administered to the patient. In some embodiments, a mixed salt oxybate (such as JZP-258) containing about 0.818 g-7.362 g, about 1.636 g-8.18 g; about 2.454 g-7.771 g; or about 3.681 g-7.362 g of GHB is administered per day.

In some embodiments, a mixed salt oxybate (such as JZP-258) containing about 0.818 g of GHB is administered per day. In some embodiments, a mixed salt oxybate (such as JZP-258) containing about 0.818 g of GHB is administered once per day. In some embodiments, a mixed salt oxybate (such as JZP-258) containing about 0.409 g of GHB is administered twice per day. In some embodiments, a mixed salt oxybate (such as JZP-258) containing about 0.273 g of GHB is administered three times per day.

In some embodiments, a mixed salt oxybate (such as JZP-258) containing about 2.454 g of GHB is administered per day. In some embodiments, a mixed salt oxybate (such as JZP-258) containing about 2.454 g of GHB is administered once per day. In some embodiments, a mixed salt oxybate (such as JZP-258) containing about 1.227 g of GHB is administered twice per day. In some embodiments, a mixed salt oxybate (such as JZP-258) containing about 0.818 g of GHB is administered three times per day.

In some embodiments, a mixed salt oxybate (such as JZP-258) containing about 3.681 g of GHB is administered per day. In some embodiments, a mixed salt oxybate (such as JZP-258) containing about 3.681 g of GHB is administered once per day. In some embodiments, a mixed salt oxybate (such as JZP-258) containing about 1.841 g of GHB is administered twice per day. In some embodiments, a mixed salt oxybate (such as JZP-258) containing about 1.227 g of GHB is administered three times per day.

In some embodiments, a mixed salt oxybate (such as JZP-258) containing about 4.908 g of GHB is administered per day. In some embodiments, a mixed salt oxybate (such as JZP-258) containing about 4.908 g of GHB is administered once per day. In some embodiments, a mixed salt oxybate (such as JZP-258) containing about 2.454 g of GHB is administered twice per day. In some embodiments, a mixed salt oxybate (such as JZP-258) containing about 1.636 g of GHB is administered three times per day.

In some embodiments, a mixed salt oxybate (such as JZP-258) containing about 6.135 g of GHB is administered per day. In some embodiments, a mixed salt oxybate (such as JZP-258) containing about 6.135 g of GHB is administered once per day. In some embodiments, a mixed salt oxybate (such as JZP-258) containing about 3.068 g of GHB is administered twice per day. In some embodiments, a mixed salt oxybate (such as JZP-258) containing about 2.045 g of GHB is administered three times per day.

In some embodiments, a mixed salt oxybate (such as JZP-258) containing about 7.362 g of GHB is administered per day. In some embodiments, a mixed salt oxybate (such as JZP-258) containing about 7.362 g of GHB is administered once per day. In some embodiments, a mixed salt oxybate (such as JZP-258) containing about 3.681 g of GHB is administered twice per day. In some embodiments, a mixed salt oxybate (such as JZP-258) containing about 2.454 g of GHB is administered three times per day.

In some embodiments, the mixed salt oxybate is administered with food. In some embodiments, the mixed salt oxybate composition is administered without food. In some embodiments, the mixed salt oxybate composition is administered with or without regard to food. In some embodiments, the mixed salt oxybate composition is administered without regard to food. In some embodiments, the patient is administered the mixed salt oxybate composition at least 2 h after the patient's last meal. In some embodiments, the patient is administered their first dose of the mixed salt oxybate composition at least 2 h after the patient's last meal. In some embodiments, the patient is administered their first dose of the mixed salt oxybate composition at least 2 h, at least 1.5 h, about 1.0 h, about 0.5 h or about 15 min after the patient's last meal. In some embodiments, the mixed salt oxybate is administered with or without regard to food after the titration period as described herein (i.e., when a stable dose of the mixed salt oxybate composition is achieved).

Although throughout the present disclosure, the amount of oxybate administered in a composition is generally expressed in terms of the amount of GHB administered (see above), the present disclosure contemplates embodiments where the oxybate dosing is expressed in the Equivalent Amount of GBA that is administered.

The Equivalent Amount of GBA in a compositions may be calculated by the following formula:

$$\text{Equivalent Amount of } GBA = \frac{\text{Amount of } GHB \text{ in (g)} \times 104.1 \left(\text{Formula Weight of } GBA, \frac{g}{mol}\right)}{103.1 \left(\text{Formula Weight of } GHB \left(\frac{g}{mol}\right)\right)}$$

In some embodiments, the dose of the mixed salt oxybate is described in terms of the amount of Equivalent Amount of GBA that is administered to the patient. In some embodiments, a mixed salt oxybate (such as JZP-258) containing about 0.826 g-7.434 g, about 1.652 g-8.26 g; about 2.478 g-7.847 g; or about 3.717 g-7.434 g of an Equivalent Amount of GBA is administered per day.

In some embodiments, a mixed salt oxybate (such as JZP-258) containing about 0.826 g of an Equivalent Amount of GBA is administered per day. In some embodiments, a mixed salt oxybate (such as JZP-258) containing about 0.413 g of an Equivalent Amount of GBA is administered twice per day. In some embodiments, a mixed salt oxybate (such as JZP-258) containing about 0.275 g of an Equivalent Amount of GBA is administered three times per day.

In some embodiments, a mixed salt oxybate (such as JZP-258) containing about 2.478 g of an Equivalent Amount of GBA is administered per day. In some embodiments, a mixed salt oxybate (such as JZP-258) containing about 1.239 g of an Equivalent Amount of GBA is administered twice per day. In some embodiments, a mixed salt oxybate (such as JZP-258) containing about 0.826 g of an Equivalent Amount of GBA is administered three times per day.

In some embodiments, a mixed salt oxybate (such as JZP-258) containing about 3.717 g of an Equivalent Amount of GBA is administered per day. In some embodiments, a mixed salt oxybate (such as JZP-258) containing about 1.859 g of an Equivalent Amount of GBA is administered twice per day. In some embodiments, a mixed salt oxybate (such as JZP-258) containing about 1.239 g of an Equivalent Amount of GBA is administered three times per day.

In some embodiments, a mixed salt oxybate (such as JZP-258) containing about 4.956 g of an Equivalent Amount of GBA is administered per day. In some embodiments, a mixed salt oxybate (such as JZP-258) containing about 2.478 g of an Equivalent Amount of GBA is administered twice per day. In some embodiments, a mixed salt oxybate (such as JZP-258) containing about 1.652 g of an Equivalent Amount of GBA is administered three times per day.

In some embodiments, a mixed salt oxybate (such as JZP-258) containing about 6.195 g of an Equivalent Amount of GBA is administered per day. In some embodiments, a mixed salt oxybate (such as JZP-258) containing about 3.098 g of an Equivalent Amount of GBA is administered twice per day. In some embodiments, a mixed salt oxybate (such as JZP-258) containing about 2.065 g of an Equivalent Amount of GBA is administered three times per day.

In some embodiments, a mixed salt oxybate (such as JZP-258) containing about 7.434 g of an Equivalent Amount of GBA is administered per day. In some embodiments, a mixed salt oxybate (such as JZP-258) containing about 3.717 g of an Equivalent Amount of GBA is administered twice per day. In some embodiments, a mixed salt oxybate (such as JZP-258) containing about 2.478 g of an Equivalent Amount of GBA is administered three times per day.

In some embodiments, the methods of the present disclosure comprise administering between 1 and 4.5 grams/day or between 6 and 10 grams/day of GHB. In some embodiments, the administered formulation comprises between 350-750 mg/ml or 450-550 mg/ml of GHB and has a pH between 6-10 or 6.5-8.

In some embodiments, the methods of the present disclosure comprise oral administration of the compositions or formulations comprising a mixed salt oxybate (disclosed herein) in a multiple dosage regimen. See U.S. Pat. No. 8,591,922, which is hereby incorporated by reference in its entirety for all purposes. In some embodiments, the multiple dosage regimen comprises one or more steps, as follows: (i) diluting an aqueous solution comprising about 500 mg/mL of the mixed salt oxybate with an aqueous medium to provide a first dose of about 1-10 grams of the mixture of salts; (ii) orally administering the dose to a patient; (iii) diluting an aqueous solution comprising about 500 mg/mL of the mixed salt oxybate to provide a second dose of about 1-10 grams of the mixed salt oxybate; and (iv) orally administering to the patient the second dose. The dose administered to the patient can be between about 0.25-9.0 grams. (All volumes and numbers are presented as Na GHB equivalents).

The embodiments are described in terms of administering a mixed salt oxybate composition; however, the present disclosure also contemplates the administration of the mixed salt oxybate in the compositions and formulations described herein. In some embodiments, the mixed salt composition is a liquid. In some embodiments, the concentration of the mixed salt in the liquid is from 50 mg/mL-950 mg/mL, about 250 mg/mL-750 mg/mL, about 350 mg/mL-650 mg/mL, or about 450 mg/mL-550 mg/mL. In some embodiments, the concentration of the mixed salt in the liquid is about 0.5 g/mL.

In one aspect, the present disclosure provides methods of treating a patient with IH comprising administering a sustained release oxybate composition to the patient with IH. In some embodiments, the sustained release composition comprises a mixed salt oxybate. In some embodiments, the composition comprises a sustained release composition described in U.S. Ser. No. 16/025,487 or U.S. Ser. No. 16/688,797, the contents of which is hereby incorporated by reference it entirety for all purposes.

The present disclosure provides, among other things, methods for administering a mixed salt oxybate to a patient with IH. Most patients with IH administered according to the methods described herein do not have cardiovascular disease or another condition (for example, high risk of stroke, renal impairment or hypertension) that would indicate them for treatment with a low sodium oxybate composition. However, in some embodiments, the patient administered the mixed salt oxybate is a patient at risk for the undesirable side effects related to high sodium intake. In some embodiments, the patient is in heart failure. In some embodiments, the patient is hypertensive. In some embodiments, the patient has renal impairment. In some embodiments, the patient is at risk for stroke.

In some embodiments, the patient is treated for excessive daytime sleepiness in patients with idiopathic hypersomnia. See U.S. Pat. Nos. 6,472,431; 6,780,889; 7,262,219; 8,263,650; 8,461,203, 8,591,922, 8,901,173, 9,132,107, 9,555,017, 9,795,567, 10,195,168, U.S. Ser. Nos. 16/688,797, 62/769,380 and 62/769,382, and U.S. Patent Publication No. 2018/0263936 for example.

In some embodiments, a pharmacy management system may be required or preferred as part of a drug distribution program. For example, the present invention includes a method for distributing a drug containing GHB or a salt thereof to an approved pharmacy, the method comprising: (1) Identifying an approved pharmacy that has an established management system to dispense information concerning the risks associated with ingesting a MCT inhibitors concomitantly to said drug to patients that are prescribed said drug; (2) Providing said pharmacy with said information related to the risks; and (3) Authorizing distribution of said drug to said pharmacy, wherein said pharmacy dispenses the drug with said information when filling a prescription for said drug. The established management system may include an electronic alert to employees to dispense said information with said drug when prescriptions are filled. Such information may be dispensed in written form, for example in a brochure explaining the risks of concomitant ingestion of GHB and an MCT inhibitor such as diclofenac, valproate, or ibuprofen or combinations thereof. For example, the information dispensed with GHB may advise a patient of the potential for enhanced potency of GHB if the patient also takes valproate. Alternatively, or in addition thereto, the information dispensed with GHB may advise a patient of the potential for decreased potency of GHB if the patient also takes diclofenac. Such information may also be dispensed in verbal form. Distributors may maintain a directory of approved pharmacies, for example in a computer readable storage medium, to further ensure that GHB is dispensed only to patients who are advised of the additive effects.

A pharmacy management system of the present invention can be a REMS system as shown in U.S. Pat. Nos. 7,895,059; 7,797,171; 7,668,730 and 8,731,963. Warnings may be administered through the existing pharmacy management system as described in the patents above.

Methods of Making

The mixed salt oxybate, compositions and formulations may be prepared using methods that are known to those skilled in the art, including the methods described U.S. Pat. Nos. 8,591,922; 8,901,173; 9,132,107; 9,555,017; 10,195,168 and U.S. Publication No. 2018/0263936, which are hereby incorporated by reference.

EXAMPLES

Example 1

This is a double-blind, placebo-controlled, randomized withdrawal, multicenter study of the efficacy and safety of JZP-258 oral solution with an open-label safety extension period.

The study consists of the following periods:
Screening Period for 14 to 30 days, with the option to rescreen once
Open-label Treatment Titration and Optimization Period for 10 to 14 weeks
Stable Dose Period for 2 weeks
Double-blind Randomized Withdrawal Period for 2 weeks
Open-label Safety Extension Period for 24 weeks
Safety Follow-up Period for 2 weeks A subset of up to 30 subjects will participate in a single overnight PK evaluation during either the Open-label Treatment Titration and Optimization Period or the Open-label Safety Extension Period.

Efficacy endpoints will include the following:
Epworth Sleepiness Scale ESS (primary endpoint), as assessed by the change in ESS score from the end of the Stable Dose Period to the end of the Double-blind Randomized Withdrawal Period.
Patient Global Impression of change (PGIc; first key secondary endpoint), assessed by the proportion of subjects reporting worsening of symptoms (minimally worse, much worse, or very much worse) at the end of the Double-blind Randomized Withdrawal Period.
Idiopathic Hypersomnia Severity Scale (IHSS; second key secondary endpoint): change in total score from the end of the Stable Dose Period to the end of the Double-blind Randomized Withdrawal Period.
Clinical Global Impression of Change (CGIC): as assessed by the proportion of participants with worsening of symptoms at end of the Double-blind Randomized Withdrawal Period.

Functional Outcomes of Sleep Questionnaire Short Version (FOSQ-10): as assessed by the change in total score from end of SDP to end of the Double-blind Randomized Withdrawal Period.

Exploratory efficacy endpoints include the following:

Visual analog scale (VAS) for sleep inertia: as assessed by the change in mean daily score from last week of SDP to last week of the Double-blind Randomized Withdrawal Period.

Total sleep time (TST): from daily sleep diary: change in the mean of the daily 24-hour TST from last week of SDP to last week of the Double-blind Randomized Withdrawal Period.

Work Productivity and Activity Impairment Questionnaire: Specific Health Problem (WPAI:SHP): change in percent of work productivity and activity impairment from end of SDP to last week of DBRWP for the following endpoints:

Change in percent work time missed due to IH.

Change in percent impairment while working due to IH.

Change in percent overall work impairment due to IH

Change in percent activity impairment due to IH.

Safety assessments will include AE monitoring, vital signs, physical examinations, 12-lead ECG, clinical laboratory tests, and the Columbia Suicide Severity Rating Scale (C-SSRS).

Screening Period (14 to 30 Days)

All subjects will be evaluated for eligibility during the Screening Period, which will occur over a period of 14 to 30 days.

Open-Label Treatment Titration and Optimization Period (10 to 14 Weeks) ("OTTP")

The aim of JZP-258 dose titration and optimization is to maximize efficacy (improved IH symptoms, e.g., EDS, sleep inertia and sleep duration,) while ensuring adequate nocturnal sleep and minimizing risk associated with safety and tolerability.

Day 1 of the study will occur the day drug is dispensed at the Baseline Visit. During the Open-label Treatment Titration and Optimization Period subjects will either transition from Xyrem to JZP-258, or initiate treatment with JZP-258, based on treatment status at study entry:

Subjects who are on a stable dose of Xyrem at study entry will switch from Xyrem to the same dosing regimen of JZP-258. The dosing regimen of JZP-258 may be adjusted until an optimally effective and tolerable dosing regimen is established.

Subjects who are not on Xyrem at study entry will initiate JZP-258 either as a once or twice nightly dosing regimen at the discretion of the investigator. The dosing regimen of JZP-258 may be adjusted until an optimally effective and tolerable dose regimen is established.

The Medical Monitor should be contacted with any questions related to dosing and titration.

All subjects will undergo at minimum a 10-week Open-label Treatment Titration and Optimization Period even if the optimized dosing regimen is achieved earlier. Every effort should be made to titrate to an optimally effective and tolerable dosing regimen within the first 8 weeks, and maintain an unchanged dose of JZP-258 for at least 2 weeks prior to entering the Stable Dose Period. Any subject for whom an efficacious and tolerable dosing regimen is not established within the first 10 weeks may undergo up to an additional 4 weeks of titration/adjustment with approval from the Medical Monitor. Subjects who are unable to attain an efficacious and tolerable dosing regimen after 14 weeks will be withdrawn from the study.

Subjects who have reached an optimized dosing regimen, and who have completed the Open label Treatment Titration and Optimization Period, will then enter the 2-week Stable Dose Period and remain on that dosing regimen throughout the Stable Dose Period.

Stable Dose Period (2 weeks) ("SDP")

Subjects will remain on the stable JZP-258 dose, unchanged, during this 2-week period. Upon completion of the Stable Dose Period, subjects will be assessed for randomization eligibility.

Double-Blind Randomized Withdrawal Period (2 Weeks) ("DBRW")

Subjects who meet the randomization criteria at the end of the Stable Dose Period will be randomized 1:1 to receive 1 of the following 2 treatments during the 2-week Double-blind Randomized Withdrawal Period.

JZP-258: Active JZP-258 will be continued as a double-blind treatment at the stable dose and regimen for 2 weeks Placebo: Placebo will be initiated as a double-blind treatment at a volume and regimen equivalent to the JZP-258 dose and regimen for 2 weeks Randomization will be stratified by the subject's use of stimulant agent and/or Xyrem at baseline per the following baseline medication groups: 1) subjects on Xyrem only; 2) subjects on Xyrem and an additional stimulant or alerting agent; 3) subjects not currently taking Xyrem but are taking a stimulant or alerting agent; or 4) subjects not currently taking Xyrem or a stimulant or alerting agent.

Based on enrollment, an optional interim analysis (IA) may be conducted when approximately 60% of the 112 planned randomized subjects have completed or are early terminated from the Double-blind Randomized Withdrawal Period. If the predefined efficacy stopping rule is met, per Data Monitoring Committee (DMC) communication, enrollment and randomization to placebo treatment may stop. All subjects who have not already been randomized would then receive open-label JZP-258 during the Double-blind Randomized Withdrawal Period. All subjects who have already entered the Double-blind Randomized Withdrawal Period will complete that period as planned.

Open-Label Safety Extension Period (24 Weeks) ("OLE")

Subjects who complete the Double-blind Randomized Withdrawal Period will enter a 24-week Open-label Safety Extension Period. Subjects will start the Open-label Safety Extension Period at a dose no higher than the dose they received at the end of the Stable Dose Period. A lower starting dose will be allowed at the discretion of the Investigator. If further titration is required, it will proceed at a rate of ≤1.5 g per night per week during this period, not to exceed a maximum total dose of 9 g/night. In the event that randomization to placebo is stopped after the IA, subjects will continue to take an effective and tolerable dose during the Open-label Safety Extension Period.

Safety Follow-Up Period (2 Weeks)

A Safety Follow-up visit will occur 2 weeks after the Open-label Safety Extension Period (completion of study).

Pharmacokinetic Study (1 Night in Open-Label Treatment Titration and Optimization Period or Open-Label Safety Extension Period)

A subset of up to 30 subjects will have the option to participate in a single overnight PK evaluation during either the Open-label Treatment Titration and Optimization Period or the Open-label Safety Extension Period. The PK evaluation night may occur on any night during 1 of the 2 periods, but preferably during 1 of the scheduled in-clinic visits. Subjects who are dosing JZP-258 on a once or twice nightly dosing regimen may be eligible to participate.

Subjects who choose to participate will take their currently assigned dose(s) at similar conditions to those normally followed at home. Subjects will take the first nightly dose at their normal bedtime. If a subject eats during the PK study, the timings for meal, snack, and doses must be recorded in the source document and the electronic case report form (eCRF).

Treatment Initiation and Titration

During the Open-label Treatment Titration and Optimization Period subjects will either transition from Xyrem to JZP-258, or initiate treatment with JZP-258, based on treatment status at study entry:

1. Subjects who are on a stable dose of Xyrem at study entry will switch from Xyrem to the same dosing regimen of JZP-258. The dosing regimen of JZP-258 then may be adjusted until an optimally effective and tolerable dosing regimen is established.

Subjects who are not on Xyrem at study entry will initiate JZP-258 either as a once nightly or twice nightly dosing regimen at the discretion of the investigator. The dosing regimen of JZP-258 may be adjusted until an optimally effective and tolerable dosing regimen is established.

The aim of JZP-258 dose titration and optimization is to maximize efficacy (reduction in IH symptoms, e.g., EDS, sleep inertia, and long sleep duration) while ensuring adequate nocturnal sleep and minimizing risk associated with safety and tolerability. The Medical Monitor should be contacted with any questions related to dosing and titration.

Subjects Starting Once Nightly Dosing Regimen

Subjects who report difficulty awakening as a result of significant sleep inertia or long sleep time (>11 hours/24 hours) may be considered for a once nightly dosing regimen at the discretion of the investigator. For subjects who initiate dosing JZP-258 as a once nightly dosing regimen, the starting dose should not exceed 3 g, the maximal single dose should not exceed 6 g, and the maximum nightly dose should not exceed 9 g. Titration should proceed at a rate of ≤1.5 g/night per week with incremental increases every few days as tolerated. The dose should be taken at bedtime. If a subject develops treatment associated sleep inadequacy on a single nightly dose, the dose may be taken after an initial period of sleep.

Subjects who initiate JZP-258 as a once nightly dosing regimen may switch to a twice nightly dosing regimen to optimize efficacy and tolerability, or to ensure adequate sleep duration. When switching to the twice nightly dosing regimen, the total nightly dose should be the same or no more than 1.5 g higher than the current dose. The first dose will be administered at bedtime or after an initial period of sleep and the second dose should be administered 2.5 to 4 hours later. Titration should proceed at a rate of ≤1.5 g/night per week, as required for optimal efficacy and tolerability; the increase in dose can be made incrementally as tolerated. The total nightly dose should not exceed 9 g/night. The maximal single dose should not exceed 6 g/night. The dose may be reduced at any time, as needed, for tolerability.

Subjects Starting Twice Nightly Dosing Regimen

Subjects who report disrupted nighttime sleep or difficulty maintaining sleep may be considered for a twice nightly dosing regimen at the discretion of the investigator.

For subjects who initiate JZP-258 as a twice nightly dosing regimen, the starting dose should not exceed 4.5 g/night divided into 2 doses (2.25 g each). The first dose will be administered at bedtime or after an initial period of sleep; the second dose should be administered 2.5 to 4 hours later. Titration should proceed at a rate of ≤1.5 g/night per week, as required for optimal efficacy and tolerability; the increase in dose can be made incrementally as tolerated. The maximal single dose should not exceed 6 g, and the total nightly dose should not exceed 9 g. The dose may be reduced at any time, as needed, for tolerability. If the subject does not achieve adequate sleep duration, the first dose may be taken after an initial period of sleep.

Subjects who initiate JZP-258 as a twice nightly dosing regimen may switch to once nightly if they are unable to wake up to take the second dose, or have difficulty awakening from sleep in the morning. The same first dose taken in the twice nightly dose regimen may be the starting dose when switching to once nightly dosing regimen. Titration should then proceed at a rate of ≤1.5 g/night per week. The maximal once nightly dose may not exceed 6 g.

While most subjects should be able to achieve an efficacious and tolerable dose while maintaining adequate sleep duration with a twice-nightly dosing regimen, in some instances there may be subjects who still are not maintaining adequate sleep duration. In these instances, subjects may divide their nightly dose into 3 administrations to ensure adequate sleep duration. In these cases, the same dosing intervals (2.5 to 4 hours), titration schedule (<1.5 g/night per week) and total nightly dose (9 g) remain applicable (See Table 1).

TABLE 1

JZP-258 Dosing Recommendations

| Dosing Regimen | Starting Nightly Dose [d] | Titration Increments [a] | Maximum Nightly Dose [b] |
|---|---|---|---|
| Once Nightly | ≤3 g | ≤1.5 g/night per week | 6 g |
| Twice Nightly | ≤4.5 g (divided) | ≤1.5 g/night per week | 9 g |
| Thrice Nightly [c] (titration only, not a starting dose) | Not applicable | ≤1.5 g/night per week | 9 g |

NOTE:
the aim of JZP-258 dose titration and optimization is to maximize efficacy (reduced IH symptoms, e.g., EDS, sleep inertia, and sleep duration) while ensuring adequate nocturnal sleep and minimizing risks associated with safety and tolerability.
[a] The weekly increase in dose of ≤1.5 g night may be made incrementally every few days as tolerated.
[b] The maximum single dose should not exceed 6 g and the maximum nightly dose should not exceed 9 g at twice or thrice nightly dosing
[c] Participants could adjust dosing to thrice nightly after initiating at twice nightly (no timing was specified in the protocol) if needed to optimize efficacy, tolerability, or sleep duration. EDS = excessive daytime sleepiness; IH = idiopathic hypersomnia.
[d] For participants who are not taking sodium oxybate at study entry Subjects will be instructed to take each dose while in bed and remain in bed after each dose. Subjects will also be instructed to complete a daily dosing diary. For all dosing regimens, investigators should caution subjects about operating hazardous machinery, including automobiles or airplanes until subjects are reasonably certain that the study drug does not affect them adversely (e.g., impair judgment, thinking or motor skill). The study allowed for dosing without regard to food.

Results

A total of 154 patients with idiopathic hypersomnia were enrolled in the study, and 115 patients were randomized (56 patients in the JZP-258 treatment group, 59 patients in the placebo treatment group). The demographics and baseline characteristics of patients in the study are depicted in Table 2. At baseline, 1.3% of patients were taking Xyrem only, 2.6% of patients were taking Xyrem and an additional stimulant or alerting agent, 53% patients were not currently taking Xyrem but were taking a stimulant or alerting agent and 43% were treatment naïve. CNS stimulants were allowed at entry, and approximately 57% of patients continued taking a stable dose of stimulant throughout the stable-dose and double-blind periods. The baseline disease characteristics of the patients in the study are depicted in Table 3. Characteristics were well balanced between randomized treatment groups and consistent with the Safety Analysis Set.

TABLE 2

Demographics and Baseline Characteristics

| | Safety Analysis Set N = 154 |
|---|---|
| Age (years) | |
| Mean (SD) | 40.3 (13.73) |
| Median (min, max) | 39.0 (19, 75) |
| Gender, n (%) | |
| Male | 49 (31.8) |
| Female | 105 (68.2) |
| Region, n (%) | |
| North America | 104 (67.5) |
| Europe | 50 (32.5) |
| Baseline Medication Group at study entry, n (%) | |
| Xyrem | 2 (1.3) |
| Xyrem + Stimulant or Alerting Agent | 4 (2.6) |
| Stimulant or Alerting Agent Only | 82 (53.2) |
| Naïve | 66 (42.9) |

TABLE 3

Baseline Disease Characteristics

| | Safety Analysis Set N = 154 |
|---|---|
| Baseline ESS | |
| Mean (SD) | 16.1 (3.59) |
| Median (min, max) | 16.5 (0, 23) |
| Baseline IHSS | |
| Mean (SD) | 32.1 (7.97) |
| Median (min, max) | 33 (5, 48) |
| Baseline CGIs | |
| Normal, not at all ill | 0 |
| Borderline ill | 1 (0.6) |
| Mildly ill | 4 (2.6) |
| Moderately ill | 55 (35.7) |
| Markedly ill | 63 (40.9) |
| Severely ill | 30 (19.5) |
| Among the most Extremely ill | 1 (0.6) |

The safety profile of JZP-258 was consistent with that of oxybate.

The pharmacokinetic parameters in patients from the Stable Dose Group administered JZP-258 once nightly or twice nightly are shown in Table 4, below.

TABLE 4

PK parameters of JZP-258 in the Stable Dose Group

| Stable Dose Group | Median Dose g/night (min, max) | Median Cmax µg/mL (min, max) | Median $AUC_{0-t\ last}$ µg/mL · h (min, max) |
|---|---|---|---|
| Once nightly | 4.0 (3, 6) | 85.9 (39.7, 110) | 229.5 (79.5, 421.8) |
| Twice nightly | 7.5 (5.3, 9) | 126 (57.1, 189) | 479.3 (190.2, 1033) |

Add the end of the DBRWP, 23% of the patients took once nightly doses ranging from 3 g to 6 g, and 77% of patients took twice-nightly dosing ranging from 4.5 g up 9 g total nightly dose. For the multidosing regimen, doses were divided equally or unequally, the first dose administered at bedtime and subsequent dose(s) administered 2.5 to 4 h apart.

The primary endpoint of Epworth Sleepiness Scale (ESS) score was assessed by the change in the ESS score from the end of the Stable Dose Period to the end of the Double-blind Randomized Withdrawal Period in JZP-258 and placebo treatment groups and is presented in Table 5. The Mean ESS across the study by randomized treatment in the mITT population is depicted in FIG. 1.

With JZP-258 treatment, patients showed substantial improvements in ESS score during the open-label titration period prior to randomization (FIG. 1).

During the randomized withdrawal portion of the trial, patients administered JZP-258 showed clinically meaningful maintenance of efficacy for the primary endpoint ESS score. There was a statistically significant worsening in patients randomized to placebo compared with patients randomized to JZP-258 for ESS (p-value<0.0001) across all dosing regimens.

During the Open-Label Safety Extension Period, maintenance of efficacy was observed in patients who had been randomized to JZP-258 and continued JZP-258 treatment during the Open-Label Safety Extension Period (FIG. 1). In addition, as shown in FIG. 1, when placebo-treated patients from the randomized withdrawal portion of the study were switched to JZP-258-treatment for the Open-Label Safety Extension Period, a significant and sustained improvement in mean ESS was observed.

TABLE 5

Change in ESS (mITT population)

| Analysis of Primary Efficacy Endpoint | JZP-258 N = 56 | Placebo N = 59 |
|---|---|---|
| End of Stable-Dose Period (Baseline) | | |
| Mean (SD) | 6.3 (4.33) | 5.8 (3.66) |
| Median (Q1, Q3) | 6.5 (2.0, 9.5) | 5.0 (3.0, 8.0) |
| Min, Max | 0, 15 | 0, 17 |
| End of Double blind Randomized withdrawal Period | | |
| Mean (SD) | 7.0 (5.03) | 13.3 (4.06) |
| Median (Q1, Q3) | 7.0 (3.0, 10.0) | 14.0 (11.0, 16.0) |
| Min, Max | 0, 21 | 3, 21 |
| Change from SDP to DBRWP | | |
| Mean (SD) | 0.7 (3.22) | 7.4 (5.16) |
| Median (Q1, Q3) | 0.0 (−0.5, 1.0) | 8.0 (3.0, 11.0) |

TABLE 5-continued

Change in ESS (mITT population)

| Analysis of Primary Efficacy Endpoint | JZP-258 N = 56 | Placebo N = 59 |
|---|---|---|
| Min, Max | −6, 10 | −4, 18 |
| LS Mean Difference (95% CI)* | −6.51 (−7.99, −5.03) | |
| p-value | <0.0001 | |

*Based on an ANCOVA model including End SDP ESS, baseline medication group, and treatment as covariates; the corresponding p-value for the treatment covariate is reported. LS mean difference estimates JZP-258 − Placebo The PGIc secondary efficacy endpoint was assessed by the proportion of subjects reporting worsening of symptoms (minimally worse, much worse, or very much worse) at the end of the Double-blind Randomized Withdrawal Period.

Figure 2:
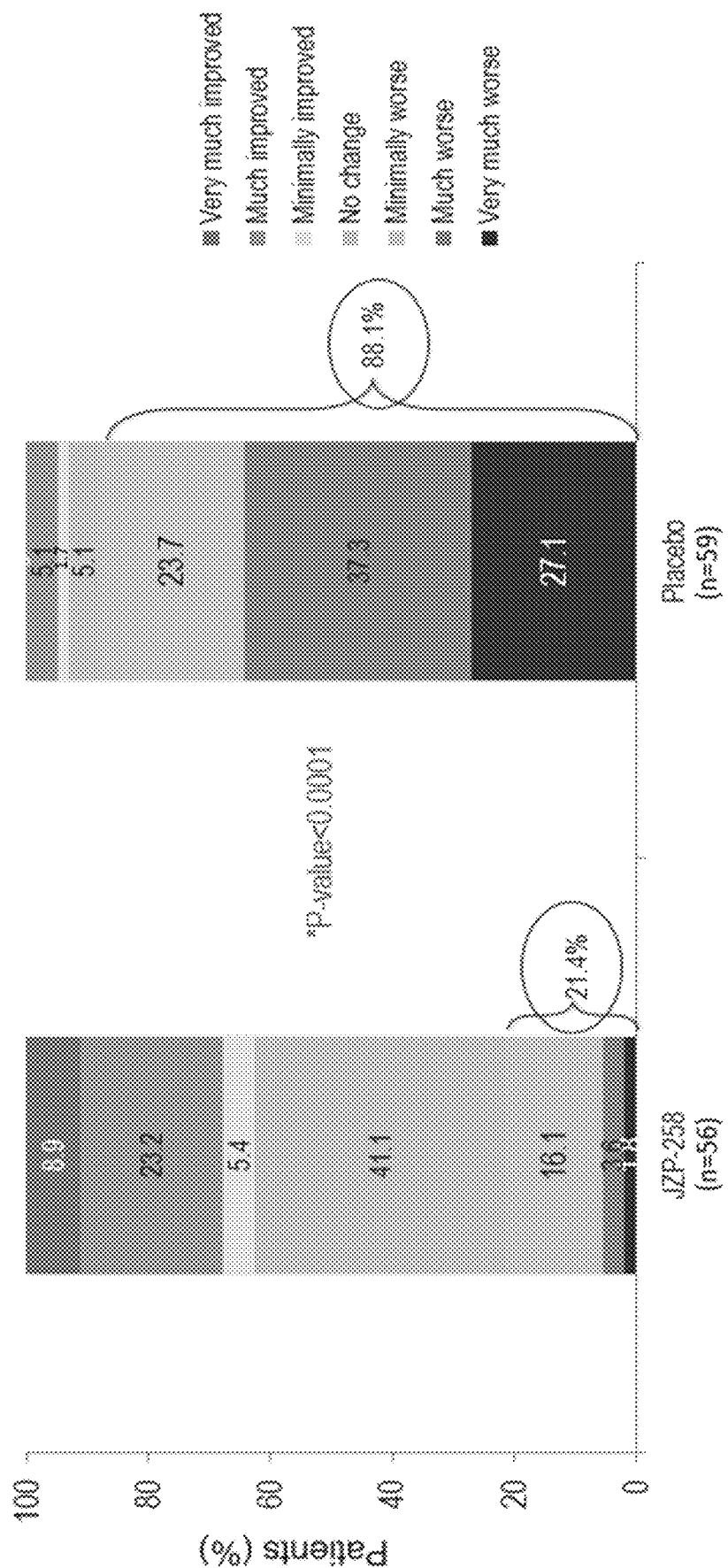
FIG. 2 shows the Patient Global Impression of change (PGIc) for patients treated with JZP-258 and patients treated with placebo at the end of the Double-blind Randomized Withdrawal Period in the study described in Example 1 (p-value<0.0001). *The p-value for comparing the proportion worsened on the PGIc between treatments is from a Cochran-Mantel-Haenszel (CMH) test stratified by baseline medication group.

During the randomized withdrawal portion of the trial, patients administered JZP-258 showed clinically meaningful maintenance of efficacy in the key PGIc secondary endpoint. As shown in FIG. 2 and Table 6 there was a significant worsening of idiopathic hypersomnia overall in patients randomized to placebo compared with patients randomized to JZP-258. At the end of the Double-blind Randomized Withdrawal Period 88.1% of the patients randomized to placebo reported worsening symptoms, whereas only 21.4% of the patients randomized to JZP-258 reported worsening symptoms (p value <0.0001).

TABLE 6

PGIc at the End of the DBRWP*

| Analysis of Key Secondary Efficacy Endpoint PGIc* Idiopathic hypersomnia Overall | Placebo (N = 59) | XYWAV (N = 56) |
|---|---|---|
| Number of Patients with at least 1 survey, n | 59 | 56 |
| Minimally, Much or Very Much worse, n (%) | 52 (88.1) | 12 (21.4) |
| p-value | <0.0001 | n/a |

PGIc is a 7-point patient-reported scale by which patients rated their symptom change at the end of the double-blind randomized-withdrawal period. Responses range from "very much better" to "very much worse."
*At the end of the DB RWP/early termination visit, Patients rated the change in their condition since the end of the Open-Label Stable-Dose Period.

The key IHSS secondary efficacy endpoint was assessed by the change in total score from the end of the Stable Dose Period to the end of the Double-blind Randomized Withdrawal Period in JZP-258 and placebo treatment groups in the modified intent-to-treat (mITT) population and is presented in Table 7. The Mean IHSS across the study by randomized treatment in the mITT population is depicted in FIG. 3.

Figure 3:
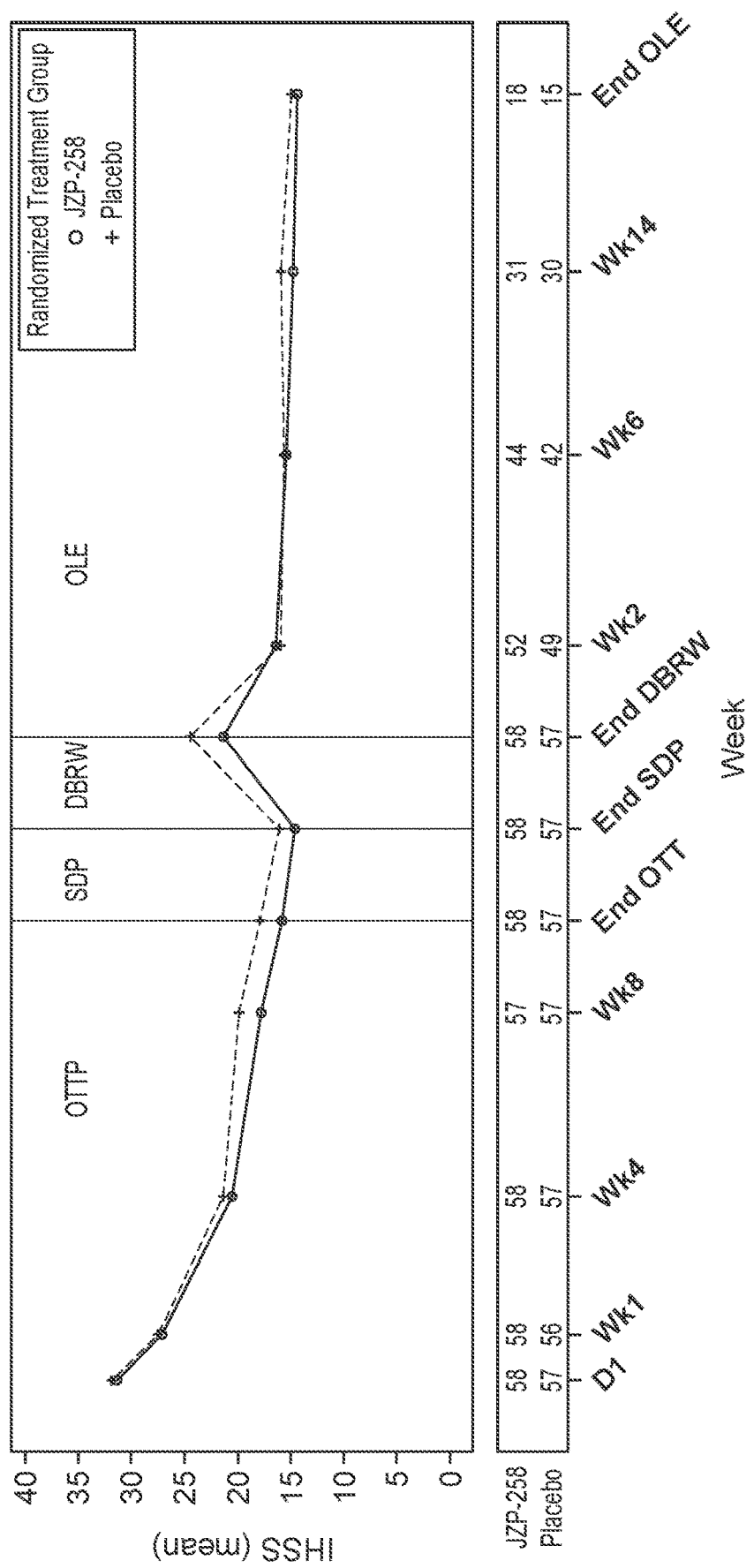
FIG. 3 shows the mean Idiopathic Hypersomnia Severity Scale (IHSS) score during the study described in Example 1 for patients treated with JZP-258 and patients treated with placebo.

With JZP-258 treatment, patients showed substantial improvements in mean IHSS during the open-label titration period prior to randomization (FIG. 3).

During the randomized withdrawal portion of the trial, patients administered JZP-258 showed clinically meaningful maintenance of efficacy for the key secondary endpoint of Idiopathic Hypersomnia Severity Scale (IHSS). There was a significant worsening in patients randomized to placebo compared with patients randomized to JZP-258 for IHSS (p-value<0.0001).

TABLE 7

Change in IHSS (mITT population)

| Analysis of Key Secondary Efficacy Endpoint | JZP-258 N = 56 | Placebo N = 59 |
|---|---|---|
| End of Stable-Dose Period (Baseline) | | |
| Mean (SD) | 15.5 (9.20) | 15.2 (7.78) |
| Median (Q1, Q3) | 14.0 (7.0, 22.0) | 14.0 (10.0, 21.0) |
| Min, Max | 1, 39 | 2, 37 |
| End of Double blind Randomized withdrawal Period | | |
| Mean (SD) | 16.9 (8.09) | 28.5 (8.96) |
| Median (Q1, Q3) | 16.0 (11.0, 23.0) | 29.0 (23.0, 34.0) |
| Min, Max | 1, 34 | 8, 49 |
| Change from SDP to DBRWP | | |
| Mean (SD) | 1.5 (5.82) | 13.3 (9.29) |
| Median (Q1, Q3) | 0 (−2.0, 2.5) | 14.0 (4.0, 19.0) |
| Min, Max | −8, 24 | −2, 38 |
| Estimated Median Difference (95% CI)* | −12.00 (−15.0, −8.0) | |
| p-value** | <0.0001 | |

*Hodges-Lehman estimate for JZP-258 − Placebo
**Rank based ANCOVA model including End SDP IHSS, baseline medication group, and treatment as covariates; the corresponding p-value for the treatment covariate is reported.

Visual Analog Scale (VAS) for sleep inertia was a secondary endpoint evaluated in this study and measured the change in the mean daily VAS score from the last week of the Stable Dose Period to the last week of the DBRWP. Sleep inertia improved with JZP-258 treatment. Patients randomized to placebo following the SDP experienced a significant increase (worsening) in mean daily VAS scores (22.5), vs. those randomized to JZP-258 (2.3, p<0.0001).

The effect of XYWAV on other secondary and exploratory endpoints, including Clinical Global Impression of change (CGIc), The Functional Outcomes of Sleep Questionnaire (FOSQ), Visual analog scale (VAS) for sleep inertia, Total Sleep Time (TST), and Work Productivity and Activity Impairment Questionnaire: Specific Health Problem (WPAI: SHP), further supports the efficacy of JZP-258 compared to placebo.

Figure 4:
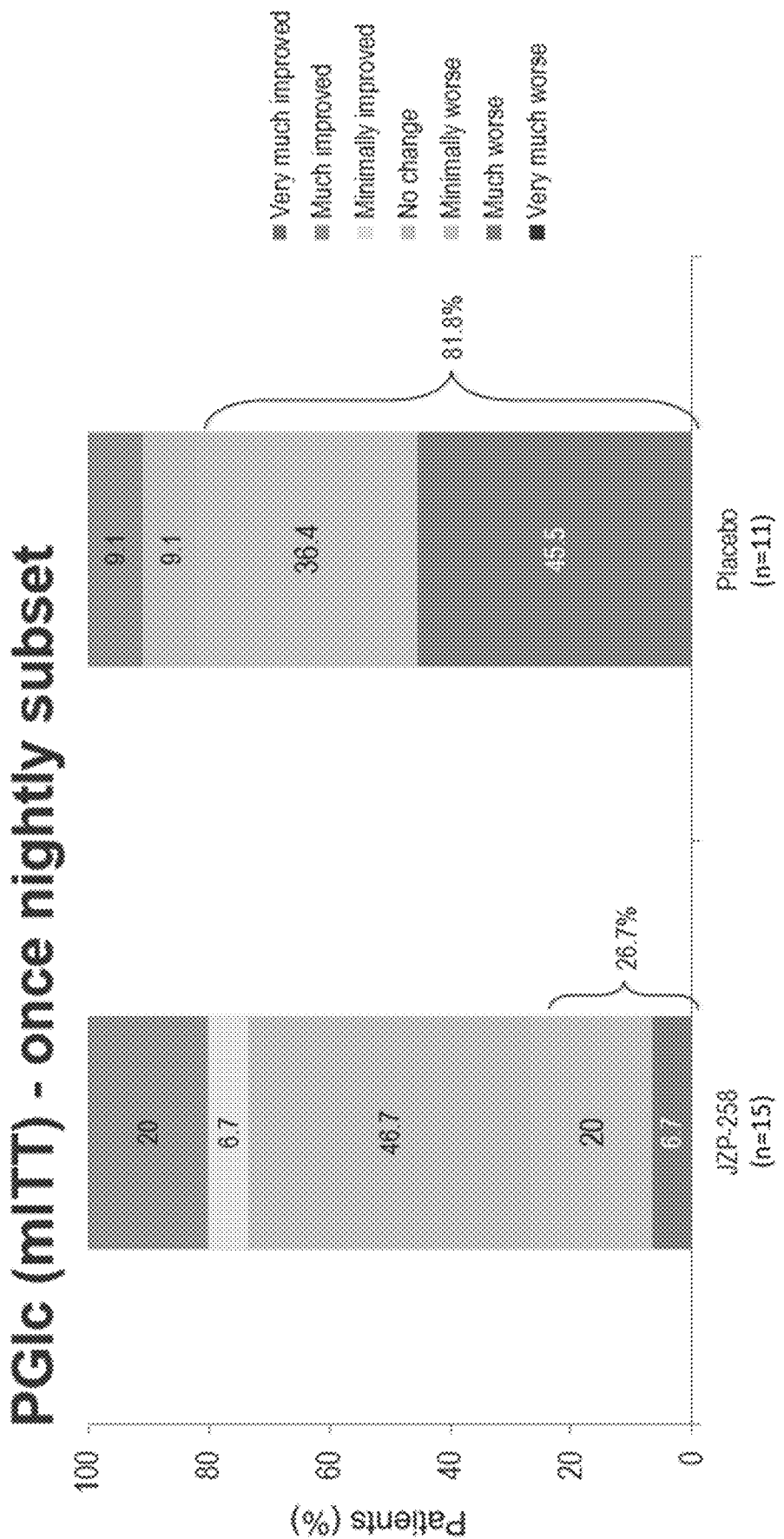
FIG. 4 shows the PGIc in the once nightly subset (patients treated once nightly with JZP-258 (n=15) and patients treated once nightly with placebo (n=11)) at the end of the Double-blind Randomized Withdrawal Period in the modified intent-to-treat (mITT) population from the study described in Example 1.
Figure 5:
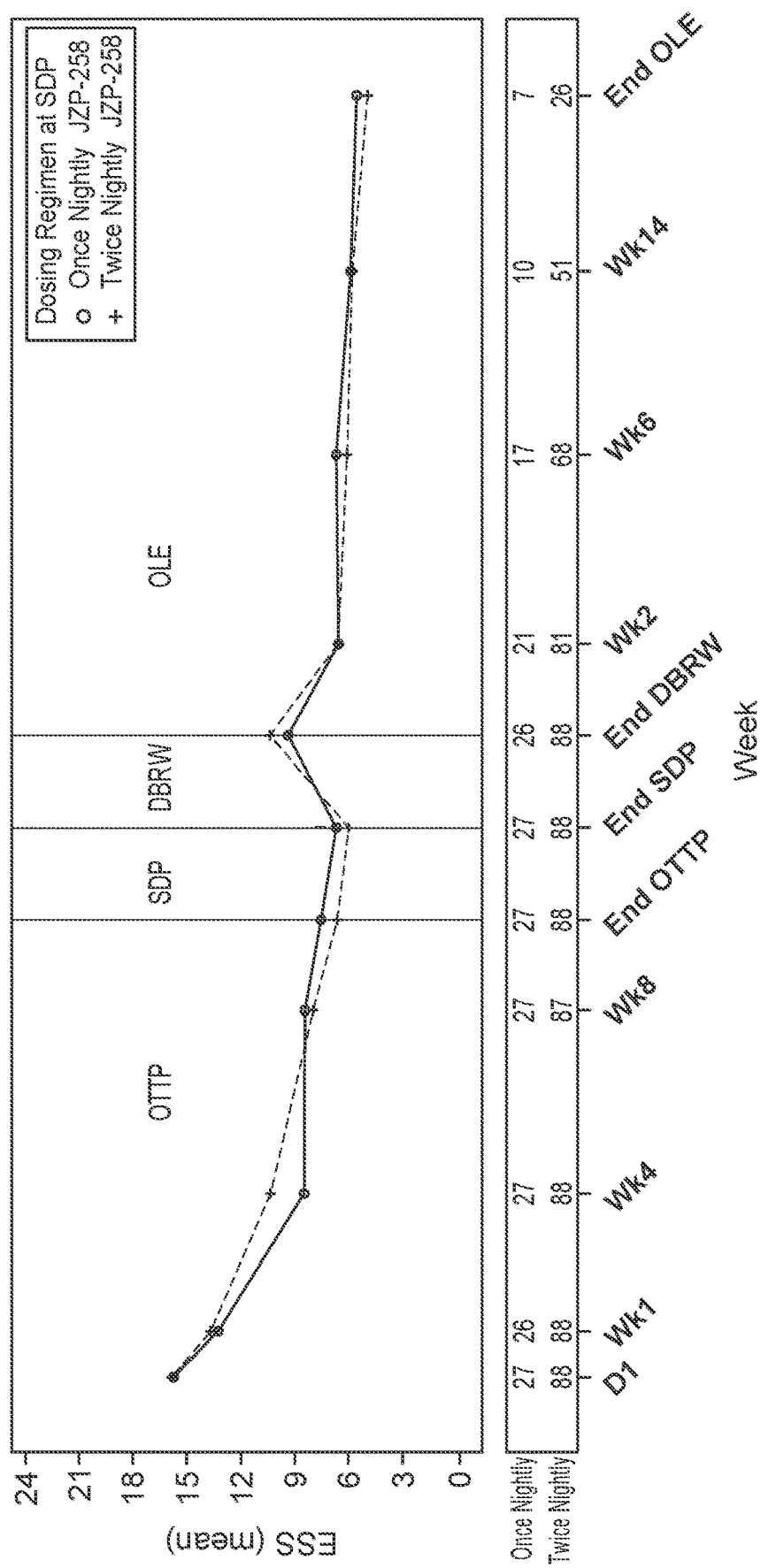
FIG. 5 shows the change in mean ESS score during the study described in Example 1 for patients treated once nightly with JZP-258 and patients treated twice nightly with JZP-258 (mITT population) during the Stable Dose Phase.

In this study JZP-258 treatment was initiated as either a once or twice nightly dosing regimen, followed by titration to an optimally effective and tolerable dose within the regimen, to the other regimen, or to thrice nightly administration. At the time of the Stable Dose Period ~75% of participants were on a twice nightly dosing regimen of JZP-258, and 25% were on a once nightly dosing regimen. The change in ESS score by Stable Dose Regimen in the mITT population in shown in Table 8. The PGIc in the once nightly subset of the patients in the mITT population is shown in FIG. 4 (81.8% [placebo] vs 26.7% [JZP-258]). The IHSS scores also worsened in participants randomized to placebo vs those continuing JZP-258 in the once-nightly group (estimated median difference [95% CI]−9.00 [−16.0, −3.0]). The study showed that change in ESS over the DBRWP was similar to that of patients taking the twice nightly regimen. The disease burden at baseline was similar for patients talking once nightly and twice nightly regimens. The change in ESS over the OLOTTP and SDP was similar for patients taking once nightly and twice nightly regimens (FIG. 5). In addition, 33 patients in the study were exposed to single doses of >4.5 g. The Median (min, max) exposure duration to doses >4.5 g was 73 days (1, 276).

TABLE 8

Subgroup Analysis of Change in ESS
by Stable Dose Regimen (mITT)

|  | Once nightly N = 26 | | Twice nightly N = 88 | |
| --- | --- | --- | --- | --- |
|  | JZP-258 | Placebo | JZP-258 | Placebo |
| n | 15 | 11 | 41 | 47 |
| Mean (SD) | 0.9 (2.22) | 5.6 (3.07) | 0.6 (3.54) | 7.7 (5.45) |
| Median | 1.0 | 5.0 | 0.0 | 8.0 |
| Q1, Q3 | 0.0, 3.0 | 3.0, 9.0 | −1.0, 1.0 | 4.0, 11.0 |
| Min., Max. | −4, 4 | 1, 10 | −6, 10 | −4, 18 |

CONCLUSIONS

The results from this study demonstrate the efficacy of JZP-258 for the treatment of IH. All clinical endpoints were met. Patients entering the study had excessive daytime sleepiness typical of the idiopathic hypersomnia population. With JZP-258 treatment, patients showed substantial improvements during the open-label titration period prior to randomization. During the randomized withdrawal portion of the trial, patients randomized to JZP-258 showed clinically meaningful maintenance of efficacy for the primary endpoint of Epworth Sleepiness Scale (ESS) score and the key secondary endpoints of the change in Patient Global Impression of Change (PGIc) scores and Idiopathic Hypersomnia Severity Scale (IHSS). There was a significant worsening in patients administered placebo compared with JZP-258 for ESS (p-value<0.0001), PGIc (p-value<0.0001) and IHSS (p-value<0.0001). No new safety signals for JZP-258 were observed in patients with IH and the overall safety profile of JZP-258 was consistent with that reported for sodium oxybate (Xyrem).

What is claimed:

1. A method of treating idiopathic hypersomnia in a patient in need thereof, the method comprising:
   a twice daily dosing regimen, comprising (a) administering to an adult patient with idiopathic hypersomnia an initial daily dose of less than or equal to about 4.5 grams of a mixed salt oxybate divided equally or unequally into 2 doses; and (b) titrating the daily dose to provide a therapeutically effective amount of the mixed salt oxybate, wherein the maximum daily dose is about 9 grams divided equally or unequally into 2 doses; or
   a once daily dosing regimen, comprising (a) administering to an adult patient with idiopathic hypersomnia an initial daily dose of less than or equal to about 3 grams of the mixed salt oxybate; and (b) titrating the daily dose to provide a therapeutically effective amount of the mixed salt oxybate, wherein the maximum daily dose is about 6 grams;
   wherein the mixed salt oxybate comprises about 5%-40% sodium oxybate, about 10%-40% potassium oxybate, about 5%-30% magnesium oxybate, and about 20%-80% of calcium oxybate (% mol. eq.).

2. The method of claim 1, wherein the mixed salt oxybate comprises about 8% sodium oxybate, about 23% potassium oxybate, about 21% magnesium oxybate and about 48% calcium oxybate (% mol. eq.).

3. The method of claim 1, wherein the initial daily dose is from about 0.5 g to about 4.5 g of the mixed salt oxybate.

4. The method of claim 1, wherein the initial daily dose is about 4.5 g of the mixed salt oxybate.

5. The method of claim 1, wherein the titration step (b) comprises administering ascending doses of the mixed salt oxybate.

6. The method of claim 5, wherein the dose is increased by about 0.5 g to 1.5 g per night per week.

7. The method of claim 1, wherein the titration step (b) is from about 1 week to about 10 weeks.

8. The method of claim 1, wherein about 4.5 g of the mixed salt oxybate is administered per day.

9. The method of claim 1, wherein about 6 g of the mixed salt oxybate is administered per day.

10. The method of claim 9, wherein about 3 g of the mixed salt oxybate is administered twice per day.

11. The method of claim 1, wherein about 7.5 g of the mixed salt oxybate is administered per day.

12. The method of claim 11, wherein about 3.75 g of the mixed salt oxybate is administered twice per day.

13. The method of claim 1, wherein about 9 g of the mixed salt oxybate is administered per day.

14. The method of claim 13, wherein about 4.5 g of the mixed salt oxybate is administered twice per day.

15. The method of claim 1, wherein the mixed salt oxybate is administered at bedtime and about 2 h-4 h after the bedtime administration.

16. The method of claim 1, wherein about 4.5 g-6.0 g of the mixed salt oxybate is administered once per day.

17. The method of claim 1, wherein the patient is administered the mixed salt oxybate at least 2 h after the patient's last meal.

18. The method of claim 1, wherein about 3 g to about 6 g is administered per day.

19. The method of claim 1, wherein the patient is an adult patient.

20. A method of treating idiopathic hypersomnia in a patient in need thereof, the method comprising:
   a twice daily dosing regimen, comprising (a) administering to an adult patient with idiopathic hypersomnia an initial daily dose of less than or equal to about 4.5 grams of a mixed salt oxybate divided equally or unequally into 2 doses; and (b) titrating the daily dose to provide a therapeutically effective amount of the mixed salt oxybate, wherein the maximum daily dose is about 9 grams divided equally or unequally into 2 doses;
   wherein the mixed salt oxybate comprises about 5%-40% sodium oxybate, about 10%-40% potassium oxybate, about 5%-30% magnesium oxybate, and about 20%-80% of calcium oxybate (% mol. eq.).

21. The method of claim 20, wherein the titration step (b) comprises administering ascending doses of no more than about 1.5 grams/night per week of the mixed salt oxybate.

22. A method of treating idiopathic hypersomnia in a patient in need thereof, the method comprising:
   a once daily dosing regimen, comprising (a) administering to an adult patient with idiopathic hypersomnia an initial daily dose of less than or equal to about 3 grams of a mixed salt oxybate; and (b) titrating the daily dose to provide a therapeutically effective amount of the mixed salt oxybate, wherein the maximum daily dose is about 6 grams;
   wherein the mixed salt oxybate comprises about 5%-40% sodium oxybate, about 10%-40% potassium oxybate, about 5%-30% magnesium oxybate, and about 20%-80% of calcium oxybate (% mol. eq.).

23. The method of claim 22, wherein the titration step (b) comprises administering ascending doses of no more than about 1.5 grams/night per week of the mixed salt oxybate.

* * * * *